US007744867B2

(12) United States Patent
Yi

(10) Patent No.: US 7,744,867 B2
(45) Date of Patent: *Jun. 29, 2010

(54) PTPASE INHIBITORS AND METHOD OF USING SAME

(75) Inventor: Taolin Yi, Solon, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/159,473

(22) Filed: May 31, 2002

(65) Prior Publication Data

US 2003/0092670 A1 May 15, 2003

Related U.S. Application Data

(60) Provisional application No. 60/294,842, filed on May 31, 2001.

(51) Int. Cl.
*A61K 38/19* (2006.01)
*A61K 45/00* (2006.01)
*A01N 59/16* (2006.01)
*A01N 55/02* (2006.01)

(52) U.S. Cl. ............... 424/85.7; 424/85.1; 424/85.4; 424/651; 514/503

(58) Field of Classification Search ............. 424/651, 424/85.4, 85.5; 530/351
See application file for complete search history.

(56) References Cited

U.S. PATENT DOCUMENTS

| | | | |
|---|---|---|---|
| 5,334,374 A | 8/1994 | Hartley et al. | |
| 5,759,837 A | 6/1998 | Kuhajda et al. | |
| 5,859,065 A | 1/1999 | Brandes | |
| 6,020,179 A | 2/2000 | Goli | |
| 6,143,765 A | 11/2000 | Tang et al. | |
| 6,197,306 B1 | 3/2001 | Murali | |
| 6,258,582 B1 | 7/2001 | Acton | |
| 6,388,076 B1 | 5/2002 | Mjalli et al. | |
| 6,410,586 B1 | 6/2002 | Moller et al. | |
| 6,569,853 B1 | 5/2003 | Borisy et al. | |
| 6,693,125 B2 | 2/2004 | Borisy et al. | |

FOREIGN PATENT DOCUMENTS

| WO | WO 00/21506 A2 | 4/2000 |
|---|---|---|
| WO | WO 00/21506 A3 | 4/2000 |

OTHER PUBLICATIONS

Li et al., Infection and Immunity, 1997, vol. 65(8), pp. 3225-3230.*
Gangneux et al., Antimicrobial Agents and Chemotherapy, 1999, vol. 43 (1), pp. 172-174.*
Almeida et al., J. Infectious Diseases, 1999, vol. 180, pp. 1735-1737.*
Badaro et al., Eur. J. Clin. Microbiol. Infec. Dis., 1994, vol. 13 (supp. 2), pp. S23-S28.*
Roberts et al., Am. J. Trop. Med. Hyg., 1996, vol. 55(4), pp. 444-446.*
Wick, et a., 2006, Curr. Pharm. Design, vol. 12, pp. 341-349.*
Herwaldt et al., Am. J. Trop. Med. Hyg., 1992, vol. 46, pp. 296-306, Abstract.*
Li et al., infect. Immun., 1997, 65(8):3225-3230.*
Garin et al., Pathol. Biol. (Paris), 1997, 45(1):48-51.*
Adachi, M., E.H. Fishcher, J. Ihle, K. Imai, F. Jirik, B. Neel, T. Pawson, S. Shen, M. Thomas, A. Ullrich, and Z. Zhao, Mammaliam SH2-containing protein tyrosin phosphatases. Cell 85:15, 1996.
Alexander, J., K.C. Carter, N. Al-Fasi, A. Satoskar and F. Brombacher, Endogenous IL-4 is necessary for effective drug therapy against visceral leishmaniasis. Eur J Immunol, 2000, 30: 2935-43.
Aoki, N. and T. Matsuda. A cytosolic protein-tyrosine phosphatase PTP1B specifically dephosphorylates and deactivates prolactin-activated STAT5a and STAT5b. J Biol Chem, 2000, 275: 29718-26.
Ayub, M. and M.J. Levell. Inhibition of testicular 17 alpha-hydrosylase and 17,20-lyase but not 3 beta-hydroxysteroid dehydrogenase-isomerase or 17 beta-hydroxysteroid oxidoreductase by ketocanazole and other imidazole drugs. J Steroid Biochem, 1987, 28: 521-3.
Bennett, J. M., Catovsky, D., Daniel, M.T., Flandrin, G., Galton, D.A. Gralnick, H.R. And Sultan, C. Criteria for the diagnosis of acute leukemia of megakaryocyte lineage (M7). a report of the French-American-British Cooperative Group. Ann Intern Med., 103: 460-2, 1985.
Bennett, J.M., Catovsky, D., Daniel, M.T., Flandrin, G., Galton, D.A. Gralnick, H.R. and Sultan, C. Proposal for the recognition of minimally differentiated acute myeloid leukaemia (AML-MO) Br J Haematol, 78: 325-9, 1991.
Bergamaschi, G., Carlo-Stella, C., Cazzola, M., De Fazio, F., Pedrazzoli, P., Peverali, F.A. and Della Valle, G. Tumor necrosis factor alpha down-regulates c-myc mRNA expression and induces in vitro monocytic differentiation in fresh blast cells from patients with acute myeloblastic leukemia. Leukemia, 4: 426-30, 1990.

(Continued)

*Primary Examiner*—Elizabeth C. Kemmerer
*Assistant Examiner*—Xiaozhen Xie
(74) *Attorney, Agent, or Firm*—Tarolli, Sundheim, Covell & Tummino LLP

(57) ABSTRACT

The various embodiments of the present invention are directed to pentavalent antimonials, purified pentavalent antimonials, and pentavalent antimonials that are comprised of an antimonial portion and an organic moiety portion. Alternatively the present invention is directed to agents and methods of screening agents which mimic the activity of pentavalent antimonials, particularly sodium stibogluconate and glucatime. An appropriate organic moiety may be selected based upon a desired interaction (e.g. steric action) with active site of a cellular component (e.g. a PTPase). In a preferred embodiment of the present invention the active site includes a cysteine residue which may be impacted by the compositions of the present invention.

18 Claims, 24 Drawing Sheets

OTHER PUBLICATIONS

Buchdunger, E., et al., Inhibition of the Abl Protein-Tyrosine Kinase In Vitro an In Vivo by a 2-phenylaminopyrimidine derivative, Cancer Res, 1996, 56: 100-04.

Berman, J. and T.J. O'Leary. Gastroinestinal stromal tumor workshop. Hum Pathol, 2001, 32: 578-82.

Berman, J.D. and M. Grogl. Leishmania mexicana: chemistry and biochemistry of sodium stibogluconate (Pentostam). Exp Parasitol, 1988, 67: 96-103.

Berman, J.D., G. Holz Jr. and D.H. Beach. Efffects of ketoconazole on growth and sterol biosynthesis of Leishmania mexicana promastigotes in culture. Mol Biochem Parasitol, 1984, 12: 1-13.

Berman J.D. and Wyler, D.J. and in vitro model for investigation of chemotherapeutic agents inleishmaniasis. J. Infect. Dis., 142: 83-86, 1988.

Berman, J.D. Chemotherapy for leishmaniasis: biochemical mechanisms, clinical efficacy, and future strategies. Rev Infect Dis, 10: 560-86, 1988.

Bittorf, T., Seiler, J., Zhang, Z., Jaster, R. and Brock, J. SHP1protein tyrosine phosphatase negatively modulates erythroid differentiation and suppression of apoptosis in J2E erythroleukemic cells. Biol Chem, 380: 1201-9, 1999.

Blanchette, J., Racette, N., Faure, R., Siminovitch, K.A. and Olivier, M. Leishmania-induced increases in activation of macrophage SHP-1 tyrosine phosphatase are associated with impaired IFN-gamma-triggered JAK2 activation. EUR J Immunol, 29: 3747-44, 1999.

Bloomfield, C.D. and Brunning, R.D. The revised French-American-British classificatio of acute myeloid leukemia: is new better? Ann Intern Med, 103: 614-6, 1985.

Blume-Jensen, P. and Hunter, T. Oncogenic kinase signaling. Nature, 411: 355-365, 2001.

Bok, R.A. and E.J. Small. The treatment of advanced prostate cancer with ketoconazole: safety issues. Drug Saf, 1999, 20: 451-8.

Borden E.C. Reducing primary melanoma mortality. Curr Oncol Rep, 2000, 2: 289-91.

Borden, E.C., Lindner, D., Dreicer, R., Hussein, M. and Peereboom, D. Second-generation interferons for cancer: clinical targets. Semin Cancer Biol, 10: 125-44, 2000.

Bradbury, J., Metastasis in colorectal cancer associated with phosphatase expression. Lancet, 358: 1245, 2001.

Breitman, T.R., Selonick, S.E. and Collins, S.J. Induction of differentiation of the human promyelocytic leukemia cell line (HL-60) by retinoic acid. Proc. Nati Acad Sci USA, 77: 2936-40, 1980.

Buick, R.N., R. Pullano, and J.M. Trent, Comparative properties of five human ovarian adenocarcinoma cell lines. Cancer Res., 45: 3668-76, 1985.

Burke, T., Jr., and Z.Y. Zhang, Protein-tyrosine phosphatases: structure, mechanism, and inhibitor discovery. Biopolymers 47: 225, 1998.

Burshtyn D.N., Scharenberg, A.M., Wagtmann, N., Rajagopalan, S., Berrada, K., Yi, T., Kinet, J.P. and Lone, E. O. Recruitment of tyrosine phosphatase HCP by the killer cell inhibitor receptor. Immunity, 4: 77-85, 1996.

Burshtyn, D.N., Yang, W., Yi, T. and Long, E.O. A novel phosphotyrosine motif with a critical amino acid at position -2 for the SH2 domain-mediated activation of the tyrosine phosphatase SHP- 1. J Biol Chem, 272: 13066-72, 1997.

Cailleau, R., Young, R., Olive, M. and Reeves, W., Jr. Breast tumor cell lines from pleural effusions. J Natl Cancer Inst, 53: 661-74, 1974.

Castrucci, M.R., P. Bilsel, and Y. Kawaoka, Attenuation of influenza A virus by insertion of a foreign epitope into the neuraminidase. J. Virol, 66: 4647-53, 1992.

Carini, C., Hudspith, B.N. and Brostoff, J. Effect of prostaglandins and cyclic nucleotides on growth and immunoglobulin secretion of two IgE myeloma cell lines. Br J Cancer, 43: 257-60, 1981.

Carter, J.D., B.G. Neel and U. Lorenz. The tyrosine phosphatase SHP-1 influences thymocyte selection by setting TCR signaling thresholds. Int Immunol 11: 1999-2013.

Cates, C.A. et al., Cancer Lett, 110: 49-55, 1992.

Chakravortty, D., Kato, Y., Sugiyama, T., Koide, N., Mu, M. M., Yoshida, T. and Yokochi, T. The inhibitory action of sodium arsenite on lipopolysaccharide-induced nitric oxide production in RAW 267.4 macrophage cells: a role of Raf-1 in lipopolysaccharide signaling. J munol, 166: 2011-7, 2001.

Chawla-Sarkar, M., Leaman, D.W., Jacobs, B.S., Tuthill, R.J., Charrerjee-Kishore, M., Stark, G.R., Borden, E.C., Resistance to interferons in melanoma cells does not correlate with the expression or activation of signal transducer activator of transcription 1 (stat 1). J. Interferon Cytokine Res. 22: 603-13, 2002.

Chen, H., Chang, S., Trub, T. and Neel, B.G. Regulation of colony-stimulating factor 1 receptor signaling by the SH2 domain-containing tyrosine phosphatase SHPTP1. Mol. Cell. Biol., 16: 3685-3697, 1996.

Chen, Y-T., Holcomb, C., Moore, H-P: H. Expression and localizaiton of two low molecular weight GTP-binding proteins, Rab8 and Rab10, by epitope tag. Proc. Nat. Acad. Sci USA 90: 6508-6512, 1993.

Chen, G.Q. et al., In Vitro Studies on Cellular and Molecular Mechanisms of Arsenic Trioxide (As203) in the Treatment of Acute Promyelocytic Leukemia: As203 induces NB4 Cell Apoptosis with Downregulation of BC1-2 Expression and Modulation of PML-RAR alpha/PML proteins; Blood 1996, 88: 1052-1061.

Chou, T.C. and Talalay, P. Quantitative analysis of dose-effect relationships: the combined effects of multiple drugs or enzyme inhibitors. Adv Enzyme Regul, 22: 27-55, 1984.

Church, D., Zhang, Y., Rago, R. and Wilding, G. Efficacy of suramin against human prostate carcinoma DU145 xenografts in nude mice. Cancer Chemother Pharmacol, 43: 198-204, 1999.

Collins, S.J., Ruscetti, F.W., Gallagher, R.E. and Gallo, R.C. Normal functional characteristics of cultured human promyelocytic leukemia cells (HL-60) after induction of differentiaition by dimethylsulfoxide. J. Exp Med, 149: 969-74, 1979.

Cyster, J.G. and Goodnow, C.C. Protein tyrosine phosphatase 1C negatively regulates antigen receptor signaling in B lymphocytes and determines thresholds for negative selection. Immunity, 2: 13-24, 1995.

Damen, J.E. Cutler, R.L., Jiao, H., Yi, T. and Krystal, G. Phosphorylation of tyrosine 503 in the erythropoietin receptor (EpR) is essential for binding the P85 subunit of phosphatidylinositol (PI) 3-kinase and for EpR-associated PI 3-kinase activity. J Biol Chem, 270: 23402-23408, 1995.

Darnell, J., Jr., Studies of IFN-induced transcriptional activation uncover the Jak-Stat pathway. J. Interferon cytokine Res., 18: 549-54, 1998.

David, M., Chen, H.E., Goelz, S., Larner, A.C. and Neel, B.G. Differential regulation of the alpha/beta interferon-stimulated Jak/Stat pathway by the SH2 domain-containing tyrosine phosphatase SHPTP1. Mol Cell Biol, 15: 7050-7058, 1995.

Diamond, R.H. et al., Mol Cell Biol, 14: 3752-62, 1994.

De, B.P. et al., Specific Interaction in Vitro and in Vivo of glyceraldehyde-e-phosphate Dehydrogenase and LA Protein with Cis-acting RNAs of Human Parainfluenze Virus Type 3, J Biol Chem, 271: 24738-35, 1996.

de Bruijn P. Kehrer Df, Verweij J. Sparreboom A. Liquid chromatographic determination of ketoconazole, a potent inhibitor of CYP3A4-mediated metabolism. J Chromatogr B biomed Sci Appl. Apr. 5, 2001; 753(2):395-400.

de Veer, M.J., M. Holko, M. Frevel, E. Walker, S. Der, J.m. Paranjape, R.H. silverman and B.R. Williams Functional classification of interferon-stimulated genes identified using microarrays. J Leukoc Biol, 2001, 69: 912-20.

Denu, J.M. and dixon, J.E. Protein tyrosine phosphatases: mechanisms of catalysis and regulation. Curr Opin Chem Biol, 2: 633-41, 1998.

Drewinko, B., M.M. Romsdahl, L.Y. Yang, M.J. Ahearn, and J.M. Trujillo, Establishment of a human carcinoembryonic antigen-producing colon adenocarcinoma cell line. Cancer Res. 36: 467-75, 1976.

Druker, B.J., Sawyers, C.L., Kantarjian, H., Resta, D. J., Reese, S.f., Ford, J.M., Capdeville, R. and Talpaz, M. Activity of a specific inhibitor of the BCR-ABL tyrosine kinase in the blast crisis of chronic myeloid leukemia and acute lymphoblastic leukemia with the Philadelphia chromosome. N Engl J Med, 344: 1038-42, 2001.

Druker, B.J., Talpaz, M., Resta, D.J., Peng, B., Nuchdunger, E., Ford, J.M., Lydon, N.B., Kantarjian, H., Capdeville, R., Ohno-Jones, S. and Sawyers, C.L. Efficacy and safety of a specific inhibitor of the BCR-ABL tyrosine kinase in chronic myeloid leukemia. N Engl J Med, 344:1032-7, 2001.

Ellery, J.M., S.J. Kempshall, and P.J. Nicholis. 2000. Activation of the interleukin 2 receptor: a possible role for tyrosine phosphatases. Cell Signal 12:367.

Elson, A., Leder, P. Identification of a cytoplasmic, phorbol ester-inducible isoform of protein tyrosine phosphatase epsilon. Proc. Natl. Acad. Sci. USA 92: 12235-39, 1995.

Espinoza-Delgado, I., M.C. Bosco, T. Musso, G.L. Gusella, D.L. Longo, and L. Varesio. 1995. Interleukin-2 and human monocyte activation. J Leukoc Biol 57:13.

Fauman, E.B. and M.A. Saper, Structure and function of the protein tyrosine phosphatases. Trends Biochem Sci, 1996, 21: 413-7.

Fenaux, P., Chastang, C., Chevret, S., Sanz, M., Dombret, H., Archimbaud, E., Fey, M., Rayon, C., Huguet, F., Sotto, J.J., Gardin, c., Makhoul, P.C., Travade, P., Solary, E., Fegueux, N., Bordessoule, D., Miguel, J.S., Link, H., Desablens, B., Stamatoullas, A., Deconinck, E., Maloisel, F., Castaigne, S. Preudhomme, C. and Degos, L. A randomized comparison of all transretinoic acid (ATRA) followed by chemotherapy and ATRA plus chemotherapy and the role of maintenance therapy in newly diagnosed acute promyelocytic leukemia. The European APL Group. Blood, 94: 1192-200, 199.

Forget, G., K.A. Siminovitch, S. Brochu, S. Rivest, D. Radzioch, and M. Olivier. 2001. Role of host phospholtyrosine phosphatase SHP-1 in the development of murine leishmaniasis. Eur J. Immunol 31:3185.

Forsberg, K., Valyi-Nagy, I., Heldin, C.H., Herlyn, M. and Westermark, B. Platelet-derived growth factor (PDGF) in oncogenesis: development of a vascular connective tissue stroma in xenotransplanted human melanoma producing PDGF-BB. Proc Natl Acad Sci USA, 90:393-7, 1993.

Frank, D.A. and Sartorelli, A.c. Alterations in tyrosine phosphorylation during the granulocytic muturation of HL-60 leukemia cells. Cancer Res, 48: 52-8, 1988.

Frearson, J.A., Yi, T. and Alexander, D.R. A tyrosine-phosphorylated 110-120-kDa protein associates with the C-terminal SH2 domain of phosphotyrosine phosphatase-ID in T cell receptor-stimulated T cells. Eur. J. Immunol., 26: 1539-1543, 1996.

Gallagher, R., collins, S., Trujillo, J., Ruscetti, F. Gallo, R., Characterization of the continuous, differentiating myeloid cell line (HL-60) for a patient with acute promyelocytic leukemia. Blood, 54: 713-33, 1979.

Gianni', M., Kalac, Y., Ponzanelli, I., Rambaldi, A., Terao, M. and Garattini, E. Tyrosine kinase inhibitor STI571 potentiates the pharmacologic activity of retinoic acid in acute promyelocytic leukemia cells: effects on the degradation of RARalpha and PML-RARalpha.Blood, 97: 3234-43, 2001.

Gianni, M., Terao, M., Zanotta, S., Barbui, T., Rambaldi, A. and Garattini, E. Retinoic acid and granulocyte colony-stimulating factor synergistically induce leukocyte alkaline phosphatase in acute promyelocytic leukemia cells. Blood, 83: 1909-21, 1994.

Gianni, M., Zanotta, S., Terao, M., Rambaldi, A. and Garattini, E. Interferons induce normal and aberrant retinoic-acid receptors type alpha in acute promyelocytic leukemia cells: potentiation of the induciton of retinoid-dependent differentiation markers. Int J Cancer, 68: 75-83, 1996.

Giard, D.J., S.a. Aaronson, g.J. Todaro, P. Arnstein, J.H. Kersey, H. dosik, and W.P. Parks, In vitro cultivation of human tumors establishment of cell lines derived from a series of solid tumors. J. Natl. Cancer Inst., 51: 1417-23, 1973.

Gillis, S., and J. Watson, 1980. Biochemical and biological characterization of lymphocyte regulatory molecules. V. Identification of an interleukin 2-producing human leukemia T cell line. J Exp Med 152: 1709.

Goldman, J.M. and Melo, J.V. Targeting the BCR-ABL tyrosine kinase in chronic myeloid leukemia. N Engl J Med, 344: 1084-6, 2001.

Goodwin, J.G. and Page, J.E. A study of the excretion of organic antibonials using a polarographic procedure. Biochem. J., 37: 198-209, 1943.

Goodwin, L.G. Pentostam (sodium stilbugluconate); a 50-year personal reminiscence. Trans R Soc Trop Med Hyg. 89: 339-41, 1995.

Gore, S.D., Weng, L.J., Jones, R.J., cowan, K., Zilcha, M., Piantadosi, S. and Burke, P.J. Impact of in vivo administration of interleukin 3 on proliferation, differentiation, and chemosensitivity of acute myeloid leukemia. Clin Cancer Res, 1: 295-303, 1995.

Gorre, M.E., M. Mohammed, K. Ellwood, N. Hsu, R. Paquette, P.N. Rao and C.L. Sawyers. Clinical Resistance to STI-571 Cancer Therapy Caused by BCR-ABL Gene Mutation or Amplification. Science, 2001, 293: 876-80.

Green, M.C., and L.D. Schultz. 1975. Motheaten, an immunodeficient mutant of the mouse. I. Genetics and pathology. J. Hered 66: 250.

Greenlee, R.T., M.B. Hill-Harmon, T. Murray, and M. Thun. 2001. Cancer statistics, 2001. Ca Cancer J. Clin 51:15.

Guan, K-L, Dixon, J.E. Evidence for Protein-tyrosine-phosphatase Catalysis Proceeding via a Cystein-Phosphate Intermediate. J. Biol. Chem. 266: 17026-30, 1991.

Haque, S.J., V. Flati, A. Deb and B.R. Williams. Roles of protein-tyrosine phosphatases in Stat 1 alpha-mediated cell signaling. J Biol Chem, 1995, 270: 25709-14.

Haque, S.J., P. Harbor, M. Tabrizi, T. Yi and B.R. Williams. Protein-tyrosine phosphatase Shp-1 is a negative regulator of IL-4- and IL-13-dependent signal transduction. J Biol Chem, 1998, 273: 3893-6.

He, L.Z., Merghoub, T. and Pandolfi, P.O. In vivo analysis of the molecular pathogenesis of acute promyelocytic leukemia in the mouse and its therapeutic implications. Oncogene, 18: 5278-92, 1999.

Heffetz, D., Bushkin, I., Dror, R. and Zick, Y. The insulinomimetic agents H2O2 and vanadate stimulate protein tyrosine phosphorylation in intact cells. J Biol Chem, 265: 2896-902, 1990.

Helson, L., S.K. Das, and S.I. Hajdu, Human neuroblastoma in nude mice. Cancer Res., 35: 2594-9, 1975.

Herwaldt, B.L. and Berman, J.D. Recommendations for treating leishmaniasis with sodium stilbgluconate (Pentostam) and review of pertinent clinical studies. Am J Trop Med Hyg, 46: 296-306, 1992.

Herwaldt, B.L., Kaye, E. T., Lepore, T.J., Berman, J.D. and Baden, H.P. *Sodium stibogluconate* (Pentostam) overdose during treatment of American cutaneous leishmaniasis. J Infect dis, 165: 968-71, 1992.

Hirai, H., Shimazaki, C., Yamagata, N., Goto, H., Inaba, T., Kikuta, T., Sumikuma, T., Sudo, Y., Ashihara, E., Fujita, N., Hibi, S., Imashuku, S., Ito, E. and Nakagawa, M. Effects of thrombopoietin (c-mpl ligand) on growth of blast cells from patients with transient abnormal myelopoiesis and acute myeloblastic leukemia. Eur J Haematol, 59: 38-46, 1997.

Hooft van Huijsduijnen, R. Protein tyrosine phosphatases: counting the trees in the forest. Gene, 225: 1-8, 1998

Hsu, H.C., Tsai, W.H., Hsu, M.L., Ho, C.H. and Wang, S.Y. Effects of colony-stimulating factors on the all-trans retinoic acid-induced differentiation of acute promyelocytic leukemic cells. Chung Hua I Hsueh Tsa Chih, 57: 93-9, 1996.

Hunter, T. The role of tyrosine phosphorylation in cell growth and disease. Harvey Lect. 94: 81-119, 1998.

Huyer, G., S. Liu, J. Kelley, J. Moffat, P. Payette, B. Kennedy, G. Tsaprailis, M.J. Gresser and C. Ramachandran. Mechanism of inhibition of protein-tyrosine phosphatases by vanadate and pervanadate . J Biol Chem, 1997, 272: 843-51.

Idres, N., Benoit, G., Flexor, M.A., Lanotee, M. and Chabot, G.G. Granulocytic differentiation of human NB4 promyelocytic leukemia cells induced by all-trans retinoic acid metabolites. Cancer Res, 61: 700-5, 2001.

Ihle, J.N., Thierfelder, W., Teglund, S., Stravapodis, D., Wang, D., Feng, J. and Parganas, E. Signaling by the cytokine receptor superfamily. ann NY Acad Sci, 865: 1-9, 1998.

Ire-Sasaki, J., Sasaki, T., Matsumoto, W., Opavsky, A., Cheng, M., Welstead, G., Griffiths, E., Krawczyk, C., Richardson, C.D., Aitken, K., Iscove, N., Koretzky, g., Johnson, P., Liu, P., Rothstein, D.M. and Penninger, J. CD45 is a JAK phosphatase and negatively regulates cytokine receptor signaling. Nature, 409: 349-54, 2001.

James, S.Y., Williams, M.A., Kelsey, S.M., Newland, A.C. and Colston, K.W. Interaction of vitamin D derivatives and granulocyte-macrophage colony-stimulating factor in leukaemic cell differentiation. Lukemia, 11: 1017-25, 1997.

Jennings, C.D., Foon, K.A. Recent Advances in Flow Cytometry: Application to the Diagnosis of Hematologic Malignancy. Blood 90: 2863-2892, 1997.

Jiao, H., Berrada, K., Yang, W., Tabrizi, M., Platanias, L.C. and Yi, T. Direct association and dephosphorylation of Jak2 kinase by SH2 domain-containing protein tyrosine phosphatase SHP-1. Mol. Cell. Biol., 16: 6985-6992, 1996.

Jiao, H., Yang, W., Berrada, K., Tibrizi, M., Shultz, L. and Yi, T. Macrophages from motheaten viable motheaten mutant mice show increased proliferative response to GM-CSF: detection of potential HCP substrates in GM-CSF signal transduction. Exp. Hematol., 25: 592-600, 1997.

Johnson, K.G., LeRoy, F.G., Borysiewicz, L.K. and Matthews, R.J. TCR signaling thresholds regulating T cell development and activation are dependent upon SHP-1. J. Immunol. 162: 3802-13, 1999.

Joliat, M.J., P.A. Lang, B.L. Lyons, L. Burenski, M:A. Lynes, T. Yi, J.P. Sundberg, and L.D. Shultz 2002. Absence of CD5 dramatically reduces progression of pulmonary inflammatory lesions in SHP-1 protein-tyrosine phosphatase-deficient viable motheaten mice. J Autoimmun 18:105.

Kemp, M., Kurtzhals, J.A., Kharazmi, A. and Theander, T.G. Interferon-gamma and interleukin-4 in human *Leishmania donovani* infections. Immunol Cell Biol, 71: 583-7, 1993.

Klimp, A.H., E.G. de Vries, G.L. Scherphof, and T. Daemen. 2002. A potential role of macrophage activation in the treatment of cancer. Crit Rev. Oncol Hematol 44: 143.

Klingmuller, U., Lorenz, U., Cantley, L.C., Neel, B.G. and Lodish, H.F. Specific recruitment of SH-PTP1 to the erythropoietin receptor causes inactivation of JAK2 and termination of proliferative signals. Cell, 80: 729-738, 1995.

Kogan, S.C. and Bishop, J.M. Acut promyelocytic leukemia: from treatment ot genetics and back. Oncogene, 18; 5261-7, 1999.

Kong, W., G.P. Swain, S. Li, and R.H. Diamond (2001) PRL-1 PTPase Expression is Developmentally Regulated With Tissue-Specific Patterns in Epithelial Tissues *Am J Physiol Gastrointest Liver Physiol*, 279, G613-21.

Lanotte, M., Martin-Thouvenin, V., Najman, S., Balerini, P., Valensi, F. and Berger, R. NB4, A maturation inducible cell line with t(15;17) marker isolated from a human acute promyelocytic leukemia (M3). Blood, 77: 1080-6, 1991.

Leibovitz, A., Stinson, J.C., McCombs, W.R., McCoy, C.E., Mazur, K.C., mabry, N.D., Classification of human colorectal adenocarcinoma cell lines. Cancer Res. 36: 4562, 1976.

Linder, D.J., Borden, E.C. and Kalvakolanu, D.V. Synergistic antitumor effects of a combination of interferons and retinoic acid on human tumor cells in vitro and in vivo. Clin Cancer Res, 3: 931-7, 1997.

Lorenz, U., K.S. Ravichandran, D. Pei, C.T. Walsh, S.J. Burakoff and B.G. Neel. Lck-dependent tyrosyl phosphorylation of the phosphotyrosine phosphatase SH-PTP1 in murine T cells. Mol Cell Biol, 1994, 14: 1824-34.

Lowenberg, B., Downing, J.R. and Burnett, A. Acute myeloid leukemia. N Engl J Med, 341: 1051-62, 1999.

Lu, C., Rak, J.W., Kobayashi, H. and Kerbel, R.S. Increased resistance to oncostatin M-induced growth inhibition of human melanoma cell lines derived from advanced-stage lesions. Cancer Res, 53: 2708-11, 1993.

Mahmoud, A.A. and Warren, K.S. Algorithms in the diagnosis and management of exotic disease. XXIV. Leishmaniases. J Infect Dis, 136: 160-3, 1977.

Margolin, K.A. 2000. Interleukin-2 in the treatment of renal cancer. Semin Oncol 27:194.

Martiny, A., Vannier-Santos, M.A., Borges, V.M., Meyer-Fernandes J.R., Assreuy, J., Cumha e Silva, N.L. and de Souza, W. Leishmania-induced tyrosine phosphorylation in the host macrophage and its implication to infection. Eur J Cell Biol, 71:206-15, 1996.

Masztalerz, A., N. Van Rooijen, W. Den Otter, and L.A. Everse. 2003. Mechanisms of macrophage cytotoxicity in IL-2 and IL-12 mediated tumor regression. Cancer Immunol Immunother 52:235.

Matin, S.F., Rackley, R.R., Sadhukhan, P.C., Kim, M.S., Novick, A.C., Bandyopadhyay, S.K. Impaired alpha-Interferon Signaling in Transitional Cell Carcinoma: Lack of p48 Expression in 5637 Cells. Cancer Res. 61: 2261-66, 2001.

Matte, C., Marquis, J.F., Blanchette, J., Gros, P., Faure, R., Posner, B.I. and Olivier, M. Peroxovanadium-mediated protection against murine leishmaniasis: role of the modulation of nitric oxide. Eur J Immunol, 30:2555-64, 2000.

Matter, W.F., et al., Biochem Biophys Res Commun, 283: 1062-8, 2001.

Mattison, C.P., S.S. Spencer, K.A. Kresge, J. Lee and I.M. Ota. Differential regulation of the cell wall integrity mitogen-activated protein kinase pathway in budding yeast by the protein tyrosine phosphatases Ptp2 and Ptp3. Mol Cell Biol., 1999, 19: 7651-60.

Mauro, M.J. and Druker, B.J. Chronic myelogenous leukemia. Curr Opin Oncol, 13: 3-7, 2001.

Melnick, A. and Licht, J.D. Deconstructing a disease: RARalpha, its fusion partners, and their roles in the pathogenesis of acute promyelocytic leukemia. Blood, 93: 3167-215, 1999.

Metcalf, D. Cellular hematopoiesis in the twentieth century. Semin Hematol, 36: 5-12, 1999.

Meurs, E. and Hovanessian, A.G. Alpha-interferon inhibits the expression of heavy chain mu messenger RNA in Daudi cells. Embo J, 7: 1689-96, 1988.

Mickey, D.D., Stone, K.R., Wunderli, H., Mickey G.H., Vollmer, R.T. and Palson, D.F. heterotransplantation of a human prostatic adenocarcinoma cell line in nude mice. Cancer Res., 37: 4049-58, 1977.

Miletti, K.E. and M.J. Leibowitz, Pentamidine inhibition of group I intron splicing in Candida albicans correlates with growth inhibition. Antimicrob Agents Chemother, 2000, 44: 958-66.

Miyagishi, M., Taira, K. U6 promoter-driven siRNAs with four uriding 3' overhangs efficiently suppress targeted gene expression in mammalian cells. Nature Biotech. 19: 497-500, 2002.

Montagna, M., O. Serova, B.S. Sylla, J. Feuteun, and G.M. Lenoir, A 100-kb physical and transcriptional map around the EDH17B2 gene: identification of three novel genes and a pseudogene of a human homologue of the rate PRL-1 tyrosine phosphatase. Hum. Genet., 96, 532-8, 1995.

Mossman, T., Rapid colorimetric assay for cellular growth and survival: application to proliferation and cytoxicity assays. J. Immunol. Methods, 65: 55-63, 1983.

Motzer, R.J., and P. Russo, 2000. Systemic Therapy for renal cell carcinoma. J Urol 163:408.

Mulders, P., R. Figlin, J.B. deKernion, R. Wiltrout, M. Linehan, D. Parkinson, W. deWolf, and A. Belldegrun. 1997 Renal cell carcinoma: recent progress and future directions. Cancer Res 57: 5189.

Murphy, G.P., and W.J. Hrushesky. 1973. Amurine renal cell carcinoma. J Natl Cancer Inst 50; 1013.

Murray, H. W., et al., Immunochemotherapy for Intracellular *Leishmania donovani* Infection: Gamma Interferon Plus Pentavalent Antimony. J. Infect. Dis., 157: 973-8, 1988.

Murray, H.W., M.J. Oca, A.M. Granger, and R.D. Schrieber, 1989. Requirement for T cells and effect of lymphokines in successful chemotherapy for an intracellular infection. Experimental visceral leighmaniasis. J. Clin Invest 83: 1253.

Murray, H.W. et al., 2000. Interleukin-12 Regulates the Response to Chemotherapy in Experimental Visceral Leishmaniasis; J. Infect Dis. 182: 182: 1497.

Murray, H.W. and S. Delph-Etienne. Roles of endogenous gamma interferon and macrophage microbicidal mechanisms in host response to chemotherapy in experimental visceral leishmaniasis. Infect Immun, 2000, 68: 288-93.

Naftalovich, S., E. Yefenof and Y. Eilam, Antitumor effects of ketoconazole and trifluoperazine in murine T-cell lymphomas. Cancer Chemother Pharmacol, 1991, 28: 384-90.

Nandan, D. and Reiner, N.E. Attenuation of gamma interferon-induced tyrosine phosphorylation in mononuclear phagocytes infected with leishmania donovani: selective inhibition of signaling through Janus kinases and Stat1. Infect Immun, 63: 4495-500, 1995.

Nandan, D., Knutson, K.L., Lo, R. and Reiner, N.E. Exploitation of hose cell signaling machiner: activation of macrophage phosphotyrosine phosphates as a novel mechanism of molecular microbial pathogenesis. J Leukoc Biol, 67: 464-70, 2000.

Nandan, D., Lo, R. and Reiner, N.E. Activation of phosphotyrosine phosphatase activity attenuates mitogen-activated protein kinase signlaing and inhibits c-FOS and nitric oxide synthase expression in macrophages infected with *Leishmania donovani*. Infect Immun, 67: 4055-63, 1999.

Nanden, D., T. Yi, M. Lopez, C. Lai, and N.E. Reiner, 2002. *Leishmania* EF-1alpha activates the Src homology 2 domain containing tyrosine phosphatase SHP-1 leading to macrophage deactivation. J. Biol. Chem 277: 50190.

O'Dwyer, M.E. and Druker, B.J. Status of bcr-abl tyrosine kinase inhibitors in chronic myelogenous leukemia. Curr Opin Oncol, 12: 594-7, 2000.

Olivier, M. Romero-Gallo, B. J., Matte, C., Blanchette, J., Posner, B.I., Tremblay, M.J. and Faure, R. Modulation of Interferon-gamma-induced macrophage activation by phosphotyrosine phosphatases inhibition. Effect on murine Leishmaniasis progression. J biol Chem, 273, 13944-9, 1998.

Pallen, C.J., the receptor-like protein tyrosine phosphatase alpha: a role in cell proliferation and oncogenesis. Semin. Cell Biol., 4: 403-8, 1993.

Parmiani, G., Rivoltini, L., Andreola, G. and Carrabba, M. Cytokines in cancer therapy. Immunol Lett, 74: 41-4, 2000.

Pathak, M.P. and T. Yi, Sodium Stibogluconate is a Potent Inhibitor of Protein Tyrosine Phosphatases and Augments Cytokine Response in Hemopoietic Cell Lines; The Journal of Immunology, 2001, 167: 3391-3397.

Pathak, Mk, X. Hu and T.Yi, Effects of Sodium Stibogluconate on Differentiation and Proliferation of Human Myeloid Leukemia Cell Lines In Vitro, Leukemia (2002) 16, 2285-2291.

Perez, J.M., M.C. Navarro-Ranninger, J.M. Requena, A. Jimenez-Ruiz, E. Parrondo, D. Craciunescu, M.C. Lopez and C. Alonso. DNA binding properties and antileukemic (L1210) activity of a Pt-pentamidine complex. Chem Biol Interact, 1991, 77: 341-55.

Perez, J.M., J.M. Requena, d. Craciunescu, J.C. Doadrio and c. Alonso. Binding of Pt-pentamidine to nucleosomal DNA. Studies of the antiproliferative activity of the drug against human cancer cells. Chem Biol Interact, 1993, 89: 61-72.

Peters, C.S., Liang, X., Li, S., Kannan, Sl, Peng, Y., Taub, R., Diamond, R.H. ATF-7, a Novel bZIP Protein, Interacts with the PRL-1 Protein-tyrosine Phoshatase, J. Biol. chem. 275: 13718-26, 2001.

Platanias, L.C., P. Domanski, O.W. Nadeau, T. Yi, S. Uddin, E. Fish, B.G. Neel and O.R. Colamonici. Identification of a domain in the beta subunit of the type I inerferon (IFN) receptor that exhibits a negative regulatory effect in the growth inhibitory action of type I IFNs. J Biol Chem, 1993, 273: 5577-81.

Platanias, L.C., Fish, E.N., Signaling pathways activated by interferons. Exp. Hematol., 27: 1583, 1999.

Puri, R.K. and Seigel, J.P. Interleukin-4 and cancer therapy. Cancer Invest. 11: 473-479, 1993.

Qin, Z., J. Schwartzkopff, F. Pradera, T. Kammertoens, b. Seliger, H. Pircher, and T. Blakenstein. 2003 A critical requirement of interferon gamma-medicated agiostasis for tumor rejection by CD8+T cells. Cancer Res. 63: 4095.

Raelson, J.V., Nervi, C., Rosenauer, A., Benedetti, L., Monczak, Y., Pearson, M., Pelicci, P.G. and Miller, W., Jr. The PML/RAR alpha oncoprotein is a direct molecular target of retinoic acid in acute promyelocytic leukemia cells. Blood, 88: 2826-32, 1996.

Rees, P.H., M.I. Keating P. A. Kager and W.T. Hockmeyer, Renal clearance of pentavalent antimony (sodium stibogluconate). Lancet, 1980, 2: 226-9.

Rice, G.P., Oger, J., Duquette, P., Fransic, G.S., Belanger, M., Laplante, S., Grenier, J.F., Treatment with interferon beta-1b improves quality of life in multiple sclerosis. Can. J. Neurol. Sci., 26: 276, 1999.

Roberts, W.L., J. Hariprashad, P.M. Rainey and H.W. Murray. Pentavalent antimony-mannan conjugate therapy of experimental visceral leishmaniasis. Am. J. Trop. Med. Hyg., 55: 444-6, 1996.

Roberts, W.L. and P.M. Rainey. Antileishmanial activity of sodium stibogluconate fractions. Antimicrob Agents Chemother, 1993, 37: 1842-6.

Rochiltz, D.F., L.E. Damon, M.B. Russi, A. Geddes and E.C. Cadman. Cytotoxicity of ketoconazole in malignant cell lines. Cancer Chemother Pharmacol, 1988, 21: 219-22.

Rosenberg, S.A. 2000. Interleukin-2 and the development of immunotherapy for the treatment of patients with cancer. Cancer J Sci Am 2000;S2.

Rosenberg, S.A. Progress in human tumor immunology and immunotherapy. Nature, 411: 380-384, 2001.

Safai, B., Sarngadharan, M.G., Groopman, J.E., Arnett, K., Propovic, M., Sliski, A., Schupbach, J. and Gallo, R.C. Seroepidemiological studies of human T-lymphotropic retrovirus type III in acquired imunodeficiency syndrome. Lancet, 1:1438-40, 1984.

Saha, S., Bardelli, A., Buckhaults, P., Velculescu, V.E., Rago, C., St. Croix, B., Romans, K.E., Choti, M.A., Lengauer, C., Kinzler, K.W., Vogelstein, B. Science, 294: 1343-6, 2001.

Salem, M., Delwel, R., Mahmoud, L.A., Clark, S., Elbasousy, E.M. and Lowenberg, B. Maturation of human acute myeloid leukaemia in vitro: the response to five recombinant haematopoietic factors in a serum-free system. Br J Haematol, 71: 363-70, 1989.

Samlowski, W.E., R. Petersen, S. Cuzzocrea, H. Macarthur, D. Burton, J.R. McGregor, and D. Salvermini, 2003. A nonpeptidyl mimic of superoxide dismutase, M40403, inhibits dose-limiting hypotension associated with interleukin-2 and increases its antitumor effects. Nat Med 9:750

Schlesinger, M., Rabinowitz, R., Kertes, T., Ravid, Z. and Goldblum, N. Antibodies to human T lymphocytes in xenoantisera elicited with a new immature T-cell line (Peer). Thymus, 2: 235-43, 1981.

Shultz, L.D., D.R. Coman, V.L. Bailey, W.G. Bearner, and C.L. Sidman. 1984. "Viable motheaten," a new allele at the motheaten locust. I. Pathology. Am J Pathol, 116:179.

Schultz, L.D., P.A. Schwietzer, T.V. Rajan, T.Yi, J.N. Ihle, R.J. Matthews, M.L. Thomas, and D.R. Beier, 1993. Mutations at the murine motheaten locust are within the hematopoietic cell protein-tyrosine phosphatase (Hcph) gene. Cell 73: 1445.

Sonouchi, K., T.A. Hamilton, C.S. Tannenbaum, R.r. Tubbs, R. Bukowski, and J.H. Finke. 1994. Chemokine gene expression in the murine renal cell carcinoma, RENCA, following treatment in vivo with interferon-alpha and interleukin-2. Am J Pathol 144:747.

Squires, K.E., Schreiber, R.D., McElrath, M.J., Rubin, B.Y., Anderson, S.L., Murray, H.W., Experimental visceral leishmaniasis: role of endogenous IFN-gamma in hose defense and tissue granulomatous response. J. Immunol., 143: 4244, 1989.

Stanhope-Baker, P. and Williams, B.R. Identification of connective tissue growth factor as a targe of WT1 transcriptional regulation. J Biol Chem, 275: 38139-50, 2000.

Stark, G.R. Genetic analysis of interfereon and other mammalian signaling pathways. Harvey Lect. 93: 1-16, 1997.

Steck, E.A. The leishmaniases. Prog Drug Res, 1974, 18: 289-351.

Sundar, S., P.R. Sinha, N.K. Agrawal, R. Srivastava, P.N. Rainey, J.D. Berman, H.W. Murray and V.P. Singh. A cluster of cases of sever cardiotoxicity among kala-azar patients treated with a high-osmolarity lot of sodium antimony gluconate. Am J Trop Med Hyg, 1998, 59: 139-43.

Sundstrom, C. and Nilsson, K. Establishment and characterization of a human histiocytic lymphoma cell line (U-937). Int J Cancer, 17: 565-77, 1976.

Tabiti, K., D.R. Smith, H.S. Goh and C.J. Pallen. Increased mRNA expression of the receptor-like protein tyrosine phosphatase alpha in late stage colon carcinomas. Cancer Lett, 1995, 93: 239-48.

Tallman, M.S. Anderson, J.W. Schiffer, C.A., Applebaum, F.R., Feusner, J.H., Ogden, A., Shepherd, L., Rowe, J.M., Francois, C., Larson, R.S. and Wiemik, P.H. Clinical description of 44 patients with acute promyelocytic leukemia who developed the retinoic acid syndrome. Blood, 95: 90-5, 2000.

Tanuma, N., K. Nakamura, H. Shima and K. Kikuchi. Protein-tyrosine phosphatase PTPepsilon C inhibits Jak-STAT signaling and differentiation induced by interleukin-6 and leukemia inhibitory factor in MI leukemia cells. J Biol Chem, 2000, 275: 28216-21.

Taolin, Yi, M.K. Pathak, D.J. Lindner, M.E. Ketterer, C. Farver and E.C. Borden. Anticancer Activity of Sodium Stibogluconate in Synergy with IFNs; The Journal of Immunology, 2002, 169: 5978-5985.

Thomassen, M.J., Yi, T., Raychaudhuri, B., Malur, A. and Kavuru, M.S. Pulmonary alveolar proteinosis is a disease of decreased availability of GM-CSF rather than an intrinsic cellular defect. Clin Immunol, 95: 85-92, 2000.

Tohda, S., Yang, G.s., Ashman, L.K., McCulloch, E.A. and Minden, M.D. Relationship between c-Kit expression and proliferation in acute myeloblastic leukemia cell lines. J Cell Physiol, 154: 410-8, 1993.

Tonks, N.K. and B.G. Neel. Combinatorial control of the specificity of protein tyrosine phosphatases. Curr. Opin Cell Biol, 2001, 13: 182-95.

Trowbridge, I.S. and M.L. Thomas, CD45: an emerging role as a protein tyrosine phosphatase required for lymphocyte activation and development. Ann. Rev. Immunol., 12:85-116, 1994.

Tsui, H.W., Simiinovitch, K. A., de Souze, L. and Tsui, F.W. Motheaten and viable motheaten mice have mutations in the haematopoietic cell phosphatase gene. Nature Genetics, 4: 124-9, 1993.

Uddin, S., Grumbach, I.M., Yi, T., Colamnoici, O.R. and Plantanias, L.C. Interferon alpha activates the tyrosine kinase Lyn in haemopoietic cells. Br J Haematol, 101: 446-9, 1998.

van Haelst-Pisani, et al., Cancer, 70:2310-2, 1992.

van Moorselaar, R.J., P. van Stratum, G. Borm, F.M. Debruyne and J.A. Schalken. Differential antiproliferative activities of alpha- and gamma-interferon and tumor necrosis factor alone or in combinations against two prostate cancer xenografts transplanted in nude mice. Prostate, 1991, 18:331-44.

Wang, C., Curtis, J.E., Minden, M.D. and McCulloch, E.A. Expression of a retinoic acid receptor gene in myeloid leukemia cells. Leukemia, 3: 264-9, 1989.

Wickrema, A., F. chen, F. Namin, T. Yi, S. Ahmad, s. Uddin, Y.H. Chen, L. Feldman, W. Stock, R. Hoffman and L. C. Platanias, Defective expression of the SHP-1 phosphatase in polycythernia vera. Exp Hematol, 1999, 27: 1124-32.

Wu, D.W., Stark, K.C., Dunnington, D., Dillon, S.B., Yi, T., Jones, C. and Pelus, L.M. SH2-Containing protein tyrosine phosphatase-1 (SHP-1) association with Jak2 in UT-7/Epo cells. Blood Cells Mol Dis, 26: 15-24, 2000.

Yang, W., Tabrizi, M., Berrada, K. and Yi, T. SHP-1 C-terminus interacts with novel substrates p32/p30 during Epo and IL-3 mitogenic response. Blood, 91: 3746-3755, 1998.

Yetter, A., Uddin, S., Krolewski, J.J., Jiao, H., Yi, T. and Platanias, L.C. Association of the interferon-dependent tyrosine kinase Tyk-2 with the hematopoietic cell phosphatase. J Biol Chem, 270: 18179-18182, 1995.

Yi, T. and Ihle, J.N. Association of hematopoietic cell phosphatase with c-Kit after stimulation with c-Kit ligand. Molecular & Cellular Biology, 13: 3350-8, 1993.

Yi, T., Cleveland, J.L., Ihle, J.N., Identification of novel protein tyrosine phosphatases of hematopoietic cells by polymerase chain reaction amplification. Blood, 78: 2222-28, 1991.

Yi, T.L., Cleveland, J.L. and Ihle, J.N. Protein tyrosine phosphatase containing SH2 domains: characterization, preferential expression in hematopoietic cells and localization to human chromosome 12p12-p13. Molecular & Cellular Biology, 12: 836-46, 1992.

Yi, T., Gilbert, D.J., Jenkins, N.A., Copeland, N.G. and Ihle, J.N. Assignment of a novel protein tyrosine phosphatase gene (Heph) to mouse chromosome 6. Genomics, 14: 795-5, 1992.

Yi, T., Mui, A.L., Krystal, G. and Ihle, J.N. Hematopoietic cell phosphatase associates with the interleukin-3 (IL-3) receptor beta chain and down-regulates IL-3-induced tyrosine phosphorylation and mitogenesis. Molecular & Cellular Biology, 13: 7577-86, 1993.

Yi, T., Zhang, J., Miura, O. and Ihle, J.N. Hematopoietic cell phosphatase associates with erythropoietin (Epo) receptor after Epo-induced receptor tyrosine phosphorylation: identification of potential binding sites. Blood, 85: 87-95, 1995.

Yi, T., M.K. Pathak, d.J. Lindner, and E.C. Borden. 200. PtPase Inhibitor Sodium Stibogluconate Inhibits the Growth of Human cancer Cell Lines in Vitro and In Vivo and Synergizes with IFNa/b. Blood, 98(11) 301a, 2001.

Yi, T., M.K. Pathak, d.J. Lindner, M.E. Ketterer, C. Farver, and E.C. Borden. 2002. Anticancer activity of sodium stibogluconate in synergy with IFNs. J Immunol 169: 5978.

Yi, T., M. Pathak, D. Lindner, M. Zhou, K. fan. SHP-1 Protein tyrosine phosphatase as a target molecule in anti-tumor immune therapies: SHP-1 Inhibitor SSG interacts with IL-2 to increase anti-murine renal tumor immunity.

Yoshida, J., N. Shibuya, T. Kobayashi, and N. Kageyama. Sensitivity to 1-(4-amino-2-methyl-5-pyrimidinyl)methyl-3-(2-chloroethyl)-3-nitrosourea hydrochloride (ACNU) of glioma cells in vivo and in vitro. Cancer, 50: 410-418, 1982.

You, M., D.H. Yi and g.s. Geng. Shp-2 tyrosine phosphatase functions as a negative regulator of the interferon-stimulated Jak/STAT pathway. Mol Cell Biol, 1999, 19: 2416-24.

Zanke, B., Squire, J., Griesser, H., Henry, M., Suzuki, H., Patterson, B., Minden, M. and Mak, T.W. A hematopoietic protein tyrosine phosphatase (HePTP) gene that is amplified and overexpressed in myeloid malignancies maps to chromosome 1q32.1. Leukemia, 8: 236-44, 1994.

Zeng, Q., W. Hong, and Y.H. Tan. Mouse PRL-2 and PRL-3, two potentially prenylated protein tyrosine phosphatases homologous to PRL-1. Biochem. Biophys. Res. Commun., 244: 421-7, 1998.

Zeng, Q., Si, X., Horstmann, H., Xu, Y., Hong, W., Pallen, C.J. Prenylation-dependent Association of Protein-tyrosine Phosphatases PRL-1, -2, and -3 with the Plasma Membrane and the Early Endosome. J. Biol. Chem. 275: 21444-52, 2000.

Zhang, J., Somani, A.K. an dSiminovitch, K.A. Roles of the SHP-1 tyrosine phosphatase in the negative regulation of cell signaling. Semin Immunol, 12: 361-78, 1999.

Zhang, Q., P.N. Raghunath, E. Vonderheid, N. Odum and M.A. Wasik. Lack of phosphotyrosine phosphatase SHP-1 expression in malignant T-cell lymphoma cells results from methylation of the SHP-1 promoter. Am J Pathol., 2000, 157: 1137-46.

Zhang, Y.L., Keng, Y.F., Zhao, Y., Wu, L. and Zhang, Z.Y. Suramin is an active site-directed, reversible, and tight-binding inhibitor of protein-tyrosine phosphateses. J Biol Chem, 273: 12281-7, 1998.

Zhao, Z., Shen, S.H. and Fischer, E.H. Phorbol ester-induced expression, phosphorylation, and translocation of protein-tyrosine-phosphatase in 1C in HL-60 cells. Proc Natl Acad Sci USA, 91: 5007-11, 1994.

\* cited by examiner

PTPASE INHIBITORS AND METHOD OF USING SAME

CROSS REFERENCE TO RELATED APPLICATIONS

This application claims the benefit of U.S. Provisional Application No. 60/294,842 filed May 31, 2001.

SUMMARY OF THE INVENTION

As used herein, the following abbreviations have the following meanings:

"AML" is used herein to mean acute myeloid leukemia;
"ATRA" is used herein to mean all-trans-retinoic acid;
"GM-CSF" is used herein to mean granulocyte/macrophage colony stimulating factor;
"IFNα" is used herein to mean interferon α;
"IFNβ" is used herein to mean interferon β;
"IL-3" is used herein to mean interleukin-3;
"Jak2" is used herein to mean janus family kinase 2;
"PSbT" is used herein to mean potassium antimonyl tartrate;
"PRL" as used herein to mean Phosphatase of Regenerating Liver
"PTPase" is used herein to mean protein tyrosine phosphatase;
"PTK" is used herein to mean protein tyrosine kinase;
"SH2" is used herein to mean Src-homology 2 domain;
"SHP-1" is used herein to mean Src-homology protein tyrosine phosphatase;
"Stat1" is used herein to mean signal transducer and activator of transcription 1;
"Stat5" is used herein to mean signal transducer and activator of transcription 5; and
"sodium stibogluconate" is used herein to mean sodium stibogluconate.

Intercellular protein tyrosine phosphorylation is regulated by extracellular stimuli, such as cytokines, to control cell growth, differentiation and functional activities. This signaling mechanism depends on the interplay of protein tyrosine kinases, which initiate signaling cascades through phosphorylating tyrosine residues in protein substrates, and by protein tyrosine phosphatases that terminate signaling via substrate dephosphorylation. Chemical compounds that modulate the activity of protein tyrosine kinases or phosphatases can induce cellular changes through affecting the balance of intracellular protein tyrosine phosphorylation and redirecting signaling.

Protein tyrosine phophorylation is a pivotal signaling mechanism regulated by the balanced activities of protein tyrosine kinases (PTKs) and protein tyrosine phosphatases (PTPases). The potential of these therapeutics are well demonstrated by the successful treatment of human chronic myelogenous leukemia (CML) and gastrointestinal stromal tumors with PTK inhibitor STI-571.

So far, few clinically usable inhibitors of PTPases have been reported despite extensive efforts in the last decade to identify them. Although a number of chemicals that broadly inhibit PTPases are known (e.g. sodium orthovanadate, pervanadate, and iodoacetic acid), their value as therapeutic agents has been limited due to their non-selective action resulting in toxicity in vivo.

SUMMARY OF THE INVENTION

An embodiment of the present invention provides a therapeutic composition containing a pentavalent antimonial. The pentavalent antimonial preferably includes a pentavalent antimonial component and an organic moeity, preferably an organic moeity that is complimentary to a predetermined cellular target(s) such as a PTPase. Examples of pentavalent antimonials that may be useful in the present invention include antimony dextran glucoside, antimony mannan, ethyl stibanime, ureastibamine, sodium stibogluconate, and glucantime, and biological equivalents of said compounds.

Another aspect of the present invention is a purified fraction of a pentavelent antimony compound, the purified fraction being useful for therapeutic application. An example of this is a purified form of sodium stibogluconate. In a preferred embodiment the pentavalent antimonials that can be used in accordance with the present invention may be any such compounds which inhibit PTPase. The types of diseases that can be treated with the present invention include, but are not limited to, the following: diseases associated with PTPase activity, immune deficiency, cancer, infections (such as viral infections), hepatitis B, and hepatitis C. The types of cancers that the present embodiment can be used to treat include those such as lymphoma, multiple myeloma, leukemia, melanoma, prostate cancer, breast cancer, renal cancer, and bladder cancer.

Another embodiment of the present invention provides for a composition which is comprised of a pentavalent antimonial and a cytokine. The cytokine may be any suitable cytokine, including interferon α, interferon β, interferon γ, or granulocyte/macrophage colony stimulating factor. The pentavalent antimonial can be any of the aforementioned pentavalent antimonials and is preferably sodium stibogluconate, glucantime, or biological equivalents thereof. The composition of this embodiment contains an effective amount of pentavalent antimonial that can be used in treating infectious diseases. The types of diseases that can be treated with the present invention include, but are not limited to, the following: diseases associated with PTPase activity, immune deficiency, cancer, infections (such as viral infections), hepatitis B, and hepatitis C. The types of cancers that the present embodiment can be used to treat include those such as lymphoma, multiple myeloma, leukemia, melanoma, prostate cancer, breast cancer, renal cancer, and bladder cancer.

Another embodiment of the present invention provides for a method of treating a subject in need thereof by administering a pentavalent antimonial, particularly those mentioned above. This embodiment of the present invention can be used to treat a patient who suffers from a disease state, such as cancer, infection (such as a viral infection), immune deficiency, hepatitis B, hepatitis C, or a disease associated with PTPase activity. This embodiment also optionally provides for the administering of a cytokine in connection with the pentavalent antimonial, such as interferon α, interferon β, interferon γ, or granulocyte/macrophage colony stimulating factor.

Another aspect of the present invention is a method of screening or identifying compounds which are functional equivalents of sodium stibogluconate or glucatime. Although these may be pentavalent antimonials as described herein, other compounds demonstrating characteristics similar to sodium stibogluconate and glucatime may satisfy this aspect of the invention.

Sodium stibogluconate is described herein as an agent inhibitor of PTPase. Sodium stibogluconate is described in U.S. Pat. No. 4,594,241 to Rao et al. in an anti-leishmanial pharmaceutical formulations. U.S. Pat. No. 4,594,241 is incorporated herein by reference to the extent it supports the present application.

DETAILED DESCRIPTION

Figure 1:
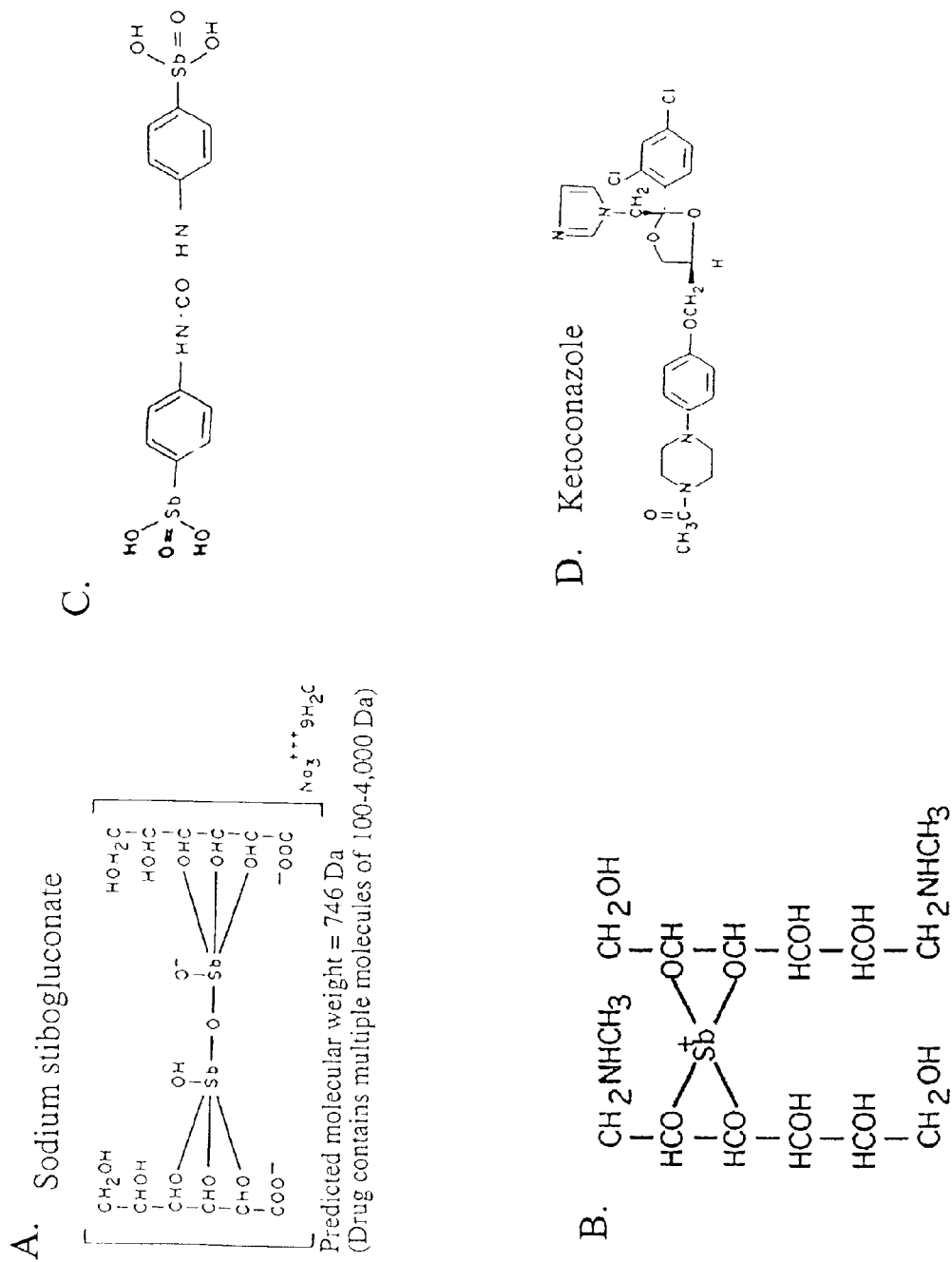
FIG. 1 illustrates the hypothetic structure of A. Sodium stibogluconate; B. Glucantime; C. Ureastibamine; and D. Ketoconazole.

As described above, one aspect of the present invention is directed to therapeutic applications of antimony, particularly, antimony conjugated to various organic moeities. Accordingly, therapeutic pentavalent antimonials are described herein. More particularly, pentavalent antimonials that have a high degree of activity and/or specificity for PTPase are described. Although a finite number of pentavalent antimonials are described herein the present invention is not to be so limited. Additionally, although it is theorized that the compounds of the present invention bind to an active site of a PTPase, they may simply tangentially interact with the activity of PTPase vis-à-vis modification or inhibition of other celluar targets upstream or downstream from a particular PTPase. While not wishing to be bound by theory it is believed that covalent modification of a sulfhydryl group of a catalytic site cysteine conserved in all PTPases. Accordingly, another aspect of the present invention is the treatment of a disease which includes an cysteine residue in an active site. The organic moeity, generally a carbohydrate, preferably provides a configuration complementary to the catalytic site or pocket of a PTPase for optimal antimony/sulfhydryl interaction.

Disclosed herein are compositions and methods useful in modulating the activity of protein tyrosine phosphorylation. Protein tyrosine kinases initiate signaling cascades through phosphorylating tyrosine residues in protein substrates, and by protein tyrosine phosphatases that terminate signaling via substrate dephosphorylation. Chemical compounds that modulate the activity of protein tyrosine kinases or phosphatases can induce cellular changes by affecting the balance of intracellular protein tyrosine phosphorylation and redirecting signaling.

Another aspect of the present invention is a purified fraction of a pentavalent antimonial, and in particular a purified pentavalent antimonial, preferably sodium stibogluconate and its use as a therapeutic agent, particularly as an inhibitor of PTPase.

Accordingly, an embodiment of the present invention provides for a method for the prophylactic and therapeutic treatment of diseases associated with protein tyrosine activity or abnormal activity thereof By "prophylactic", it is meant the protection, in whole or in part, against a particular disease or a plurality of diseases. By "therapeutic", it is meant the amelioration of the disease itself, and the protection, in whole or in part, against further disease. The method comprises the administration of an inhibitor of protein tyrosine phosphatase in an amount sufficient to treat a subject either prophylactically or therapeutically. Sodium stibogluconate as used herein includes all biochemical equivalents (i.e. salts, precursors, and its basic form).

The active agents described herein, as well as their biological equivalents or pharmaceutically acceptable salt of the foregoing can be administered in accordance with the present inventive method by any suitable route. One of ordinary skill in the art will appreciate that the prodrug used must be one that can be converted to an active agent in or around the site to be treated. Suitable routes of administration may include systemic, such as orally or by injection, topical, intraocular, periocular, subconjunctival, subretinal, suprachoroidal and retrobulbar. The manner in which the agent is administered is dependent, in part, upon whether the treatment is prophylactic or therapeutic.

The composition(s) of the present invention is preferably administered as soon as possible after it has been determined that an animal, such as a mammal, specifically a human, is at risk for a disease. Preferably the disease which is screened or in need of treatment is associated with protein tyrosine phosphatase activity. Treatment will depend, in part, upon the particular therapeutic composition used, the amount of the therapeutic composition administered, the route of administration, and the cause and extent, if any, of the disease.

One skilled in the art will appreciate that suitable methods of administering the therapeutic composition useful in the present inventive method, are available. Although more than one route can be used to administer a particular therapeutic composition, a particular route can provide a more immediate and more effective reaction than another route. Accordingly, the described routes of administration are merely exemplary and are in no way limiting.

The dose administered to an animal, particularly a human (humans have over 100 PTPases), in accordance with the present invention should be sufficient to effect the desired response in the animal over a reasonable time frame. One skilled in the art will recognize that dosage will depend upon a variety of factors, including the strength of the particular therapeutic composition employed, the age, species, condition or disease state, and body weight of the animal. The size of the dose also will be determined by the route, timing, and frequency of administration as well as the existence, nature, and extent of any adverse side effects that might accompany the administration of a particular therapeutic composition, as well as the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached.

Compositions for use in the present inventive method preferably comprise a pharmaceutically acceptable carrier and an amount of the therapeutic composition sufficient to treat the particular disease prophylactically or therapeutically. The carrier can be any of those conventionally used and is limited only by chemico-physical considerations, such as solubility and lack of reactivity with the compound, and by the route of administration. It will be appreciated by one of ordinary skill in the art that, in addition to the following described pharmaceutical compositions, the therapeutic composition can be formulated as polymeric compositions, inclusion complexes, such as cyclodextrin inclusion complexes, liposomes, microspheres, microcapsules, and the like (see, e.g., U.S. Pat. Nos. 4,997,652, 5,185,152 and 5,718,922). The therapeutic composition can be formulated as a pharmaceutically acceptable acid addition salt. Examples of pharmaceutically acceptable acid addition salts for use in the pharmaceutical composition include those derived from mineral acids, such as hydrochloric, hydrobromic, phosphoric, metaphosphoric, nitric, and sulfuric acids, and organic acids, such as tartaric, acetic, citric, malic, lactic, fumaric, benzoic, glycolic, gluconic, succinic, and arylsulphonic, for example p-toluenesulphonic, acids.

It is preferred that the pharmaceutically acceptable carrier be one which is chemically inert to the therapeutic composition and one which has no detrimental side effects or toxicity under the conditions of use. The choice of excipient will be determined in part by the particular therapeutic composition, as well as by the particular method used to administer the composition. Accordingly, there is a wide variety of suitable formulations of the pharmaceutical composition of the present invention.

Injectable formulations are among those that are preferred in accordance with the present inventive method. The requirements for effective pharmaceutical carriers for injectable compositions are well-known to those of ordinary skill in the art (see Pharmaceutics and Pharmacy Practice, J. B. Lippincott Co., Philadelphia, Pa., Banker and Chalmers, eds., pages 238-250 (1982), and ASHP Handbook on Injectable Drugs, Toissel, 4th ed., pages 622-630 (1986)) which is incorporated herein by reference thereto. It is preferred that such injectable compositions be administered intramuscularly, intravenously, or intraperitoneally.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The present inventive method also can involve the co-administration of other pharmaceutically active compounds. By "co-administration" is meant administration before, concurrently with, e.g., in combination with the therapeutic composition in the same formulation or in separate formulations, or after administration of a therapeutic composition as described above.

The following examples, materials, methods, discussion, and detailed description are meant to further illustrate the present invention but, of course, should not be construed as in any way limiting its scope.

Sodium stibogluconate is a complex of pentavalent antimonial with an organic moeity, in one embodiment, a carbohydrate is the organic moeity. Sodium stibogluconate is well tolerated with few side effects at its therapeutic dosage for Leishmaniasis. The recommended dosage of sodium stibogluconate for Leishmaniasis is 20 mg Sb/kg body weight per day i.m. daily for 10-14 days. The course can be repeated after a rest period of 14 days. When given at such dose and duration, the drug has efficacy that ranged from 70-100%. The upper limit of the drug that can be safely tolerated has not been defined. However, single dose up to 143 mg Sb/kg have been used without serious toxicity. The tolerance of the drug may be in part due to its rapid renal clearance with more than 80% excreted in the first 6 hours and blood levels of the drug fell to around 1% peak value in 16 hours. No obvious accumulation of the drug in the human body was detected, consistent with its safe usage for prolonged treatment in some cases of drug-resistant Leishmaniasis.

The precise chemical structure and composition of sodium stibogluconate remain undefined. Sodium stibogluconate is prepared by the reaction of pentavalent antimony with gluconic acid. Some lots of sodium stibogluconate associated with poor clinical outcomes have been found to have higher osmolalities that suggest a diminished degree of sodium stibogluconate polymerization. Sodium stibogluconate was found to be a complex mixture with apparent molecular masses of 100-4,000 Da and could be separated into 12 fractions by anion-exchange chromatography. The hypothetic structure of sodium stibogluconate is shown in FIG. 1A with a predicted molecular weight of 746 Da. Based on the ability of antimony in sodium stibogluconate to form stable complex with proteins, it would appear that the pentavalent antimony interacts with key sulfhydryl groups of polypeptides and that this may be a mechanism of action of the drug. While not wishing to be bound by theory, it is hypothesized that sodium stibogluconate may inhibit PTPases via covalent modification of the sulfhydryl group in the cysteine residue conserved in PTPases while its carbohydrate moiety providing certain molecular configuration that brings the antimony into proximity of the cysteine residue at the catalytic pocket of PTPases.

The finding of sodium stibogluconate as a PTPase inhibitor with anti-cancer activity suggests that several drugs, related to sodium stibogluconate biologically and/or chemically, may have similar activities against PTPases and thus similar potential as novel anti-cancer therapeutics. Chemically-related drugs include glucantime (see FIG. 1B), antimony dextran glucoside, antimony mannan, ethyl stibanine and urea stibamine (see FIG. 1C). All of these pentavalent antimonials have anti-leishmania activity but are less used clinically since sodium stibogluconate has more satisfactory stability, better profile of tolerance and efficacy. Because different organic moieties in each of the drugs make them structurally different from that of sodium stibogluconate, these drugs may selectively target different groups of PTPases and consequently have activity against different types of cancer cells. Glucantime is produced by Specia (France), and is commercially available therefrom.

Several drugs containing no pentavalent antimony are also used in the treatment of leishmaniasis, including ketoconazole (See FIG. 1D). The mechanism of their anti-leishmania activity is not fully understood. There are no reports of their activity against PTPases. We have provided evidence that ketoconazole is a PTPase inhibitors and that it targets PTPases differently than those inhibited by sodium stibogluconate. Thus Ketoconazole may selectively inhibit different groups of PTPases and consequently may have activity against different types of cancer cells.

A very good review of agents effective in the treatment of leishmaniasis is found in Steck, E.A. The leishmaniases, Prog Drug Res, 18: 289251 (1974), which is incorporated herein by reference thereto in its entirety. Particular reference is directed to pages 306--315 which describe antimonates. Because different organic moieties in each of the drugs make them structurally different from that of sodium stibogluconate, these drugs may selectively target different groups of PTPases and consequently may have activity against different types of cancer cells. Although potassium antimony tartrate (PSbT) has no detectable activity against PTPases, the marked activity of the trivalent antimony in growth inhibition of Baf3 cell line suggests this type of chemical compounds may also have anti-cancer activity via a mechanism independent of PTPases. Pentavalent antimony compounds appear to be particularly well-suited for purposes of the present invention.

Figure 2:
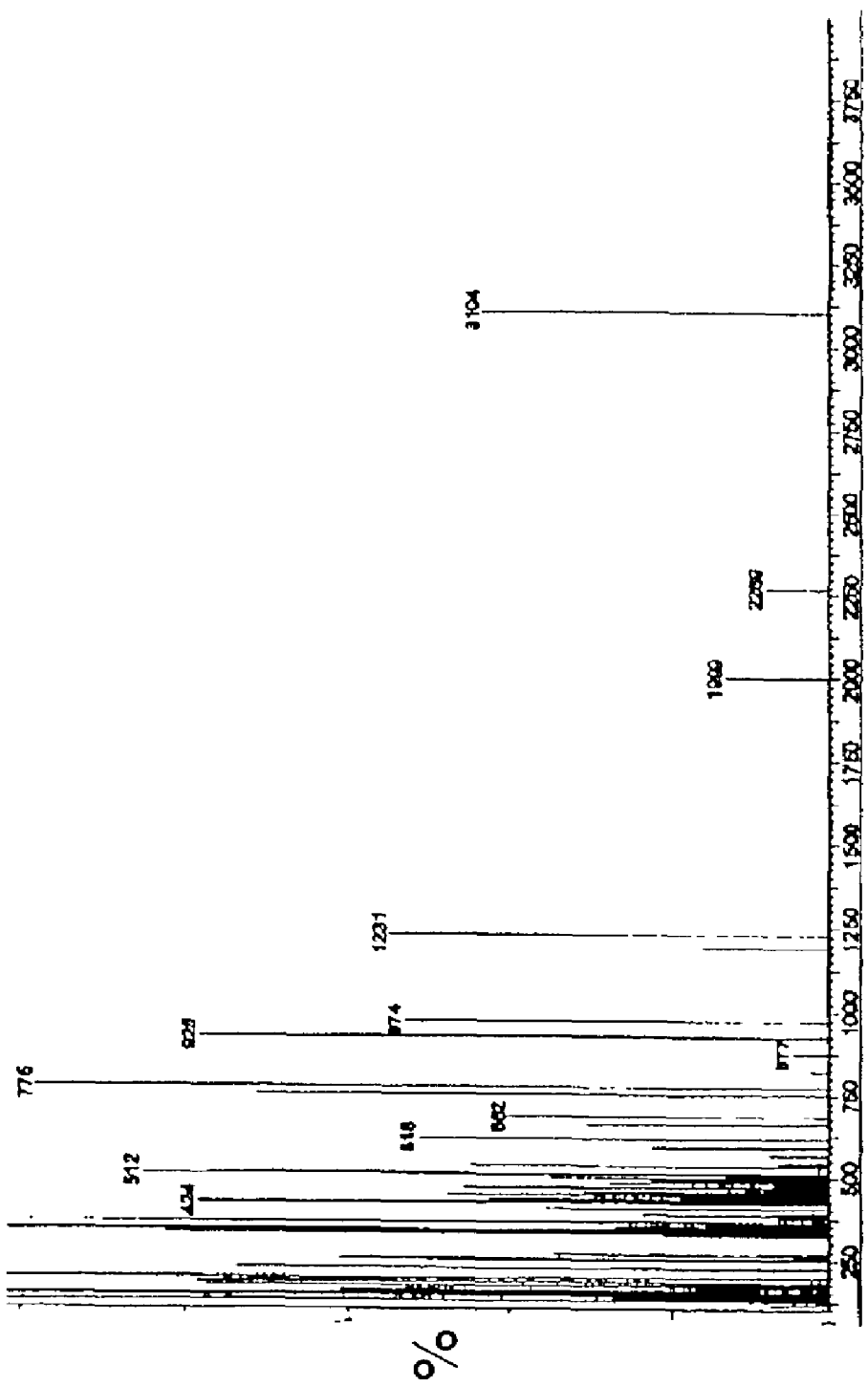
FIG. 2 is a mass spectrometric analysis of commercially avaliable sodium stibogluconate.

To assess the number of molecular species and their relative amounts and molecular weights in sodium stibogluconate, sodium stibogluconate was characterized by mass spectrometry. This is illustrated in FIG. 2. Significantly, the results revealed the presence of only a few major species of higher molecular weights (>700 Da) that are well separated and relatively easy to isolate by chromatography. Since degradation of polymers of sodium stibogluconate associates with lower activity and increased toxicity, the more active portion of sodium stibogluconate may be among the higher molecular weight species. The anti-cancer activity of sodium stibogluconate likely associates with a distinct sodium stibogluconate fraction more potent and less toxic than the parental drug, which is a mixture of molecules resulted from differential polymerization with poor activity and increased toxicity associated with degradation of the polymers. To determine the activities of different sodium stibogluconate fractions, they were separated by chromatography. Sodium stibogluconate is a mixture of pentavalent antimony complexed to carbohydrate specifically carbohydrates from gluconic acid, with the number and composition of chemical species in the formulation undefined. It was shown by chromatography that sodium stibogluconate is mixture of molecules of about 100 to about 4,000 Da and could be separated into 12 fractions by anion-exchange chromatography. Preliminary studies by mass spectrometry confirmed its mixed nature and demonstrated for the first time the distribution of major molecular species at about 100 to about 3104 Da range in the drug. Compounds with different molecular weights that resulted from different polymerization in the sodium stibogluconate mixture may have distinct biological activities and toxicity. To verify the activity, sodium stibogluconate fractions were purified based on their different molecular weights by chromatography and their anti-cancer activities assessed by determining their activities against PTPases in comparison to the parental sodium stibogluconate. To assess their toxicity, the LD50 of the fractions and parental sodium stibogluconate can be determined in mice.

Figure 2A:
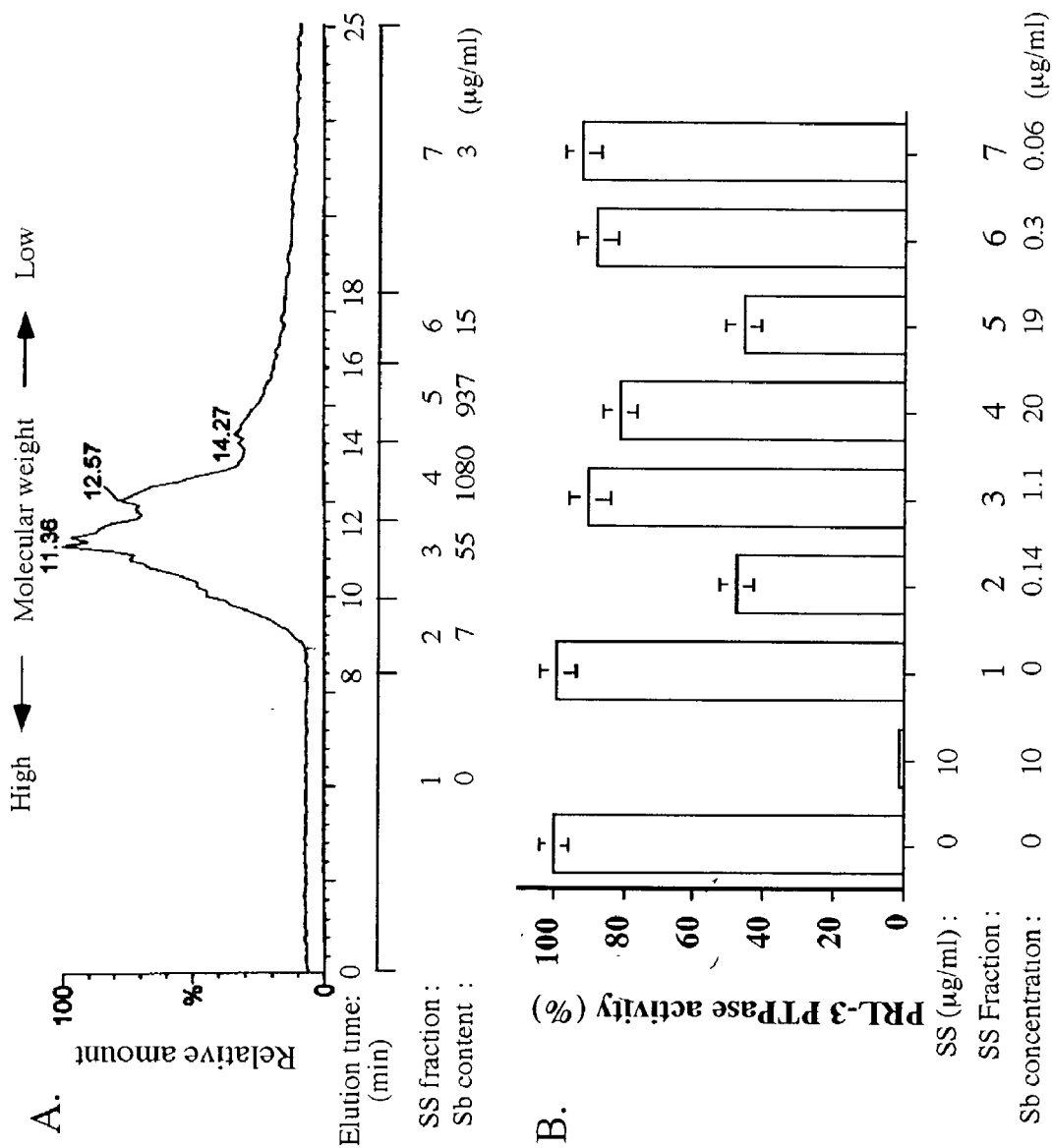
FIG. 2A illustrates PTPase inhibitory activity associates with selective higher molecular compounds in sodium stibogluconate. A. sodium stibogluconate was separated by molecular sieve chromatography and collected as fractions during elution with antimony (Sb) contents of individual fractions quantified by inductively coupled plasma mass spectrometry (ICPMS). Values of Sb contents have about 10% maximum relative error based on systematic error and random error in analysis of standards. B. Relative PTPase activities of recombinant SHP-1 in the presence of sodium stibogluconate fractions and parental sodium stibogluconate as measured by in vitro PTPase assays. Antimony (Sb) concentrations in the PTPase reactions were calculated based on the antimony contents of sodium stibogluconate and sodium stibogluconate fractions determined by ICPMS.

As shown in FIG. 2A, molecular size exclusion chromatography has been used successfully to characterize sodium stibogluconate with different molecular weights ranging from 100 to 4000 Da. Molecular exclusion HPLC techniques were used to isolate and purify sodium stibogluconate fractions. Sodium stibogluconate in its clinical format from Xinhua Pharmaceutics as used in preliminary studies has been obtained in quantity (approximately 1000 ml of sodium stibogluconate at 100 mg Sb/ml) for the proposed studies. Compounds in the sodium stibogluconate mixture were eluted in a time dependent manner.

Given the distribution of the major species of molecules in sodium stibogluconate as illustrated by mass spectrometry (FIG. 2), the eluted fractions were initially collected as seven pools from high molecular weight to lower molecular weight. Most of the fractions were eluted between 8-25 minutes as revealed by mass spectroscopy. The activities of the fractions were tested against PTPases in vitro, particularly PRL-3PTPase, to identify the pool with activity or highest activity. The pools without activity or with lower activity can be used in their mixed form to determine their toxicity (LD50) as described below. Consistent with a lack of compounds in fraction 1 (eluate of 0-8 minutes), no antimony was detected in the fraction by inductively coupled plasma mass spectrometry (FIG. 2A). Fractions 2-7 showed various amounts of antimony content with the highest levels detected in fractions 4 and 5 that accounted for 96% of total antimony in the eluates (FIG. 2A). Importantly in FIG. 2A, the higher molecular weight polymers (e.g., greater than 700 Da and more particularly greater than 3000 Da are more potent than the parental sodium stibogluconate in inhibiting PTPasees. This appears to be confirmed by the activity of Fraction 2 and its corresponding inhibition on PRL-3 PTPase activity. This is also shown in B of FIG. 2A. The activities of the sodium stibogluconate pools, fractions and sodium stibogluconate against PTPases SHP-1 were tested individually by in vitro PTPase assays as described subsequently.

Inhibitory activities of the fractions and parental sodium stibogluconate mixture against recombinant SHP-1 PTPase was assessed by in vitro PTPase assays. Consistent with our previous observation, sodium stibogluconate at Sb concentration of 10 μg/ml inactivated SHP-1 (B of FIG. 2A). As expected since it contained no detectable compounds or antimony (A of FIG. 2A), fraction 1 showed no activity against SHP-1. Fractions 6 and 7 also failed to inhibit the PTPase although they had low levels of antimony. Interestingly, fraction 2 with an antimony level similar to those in fraction 6 and 7 was active against SHP-1. In contract, fraction 3 and 4 showed only minor effects on SHP-1 PTPase activity despite the fact that their antimony levels were approximately 10-200 fold higher than that of fraction 2. Fraction 5 also showed a significant activity against SHP-1 with its antimony level almost 100 fold over that of fraction 2. These results demonstrated that inhibitory activity against recombinant SHP-1 associated with selective compounds in the sodium stibogluconate mixture in a manner not solely defined by antimony content. Since the most effective SHP-1 inhibitor(s) resided in fraction 2 that was eluted first in molecular sieve chromatography and thus of higher molecular weights but accounted for less than 10% of total compounds in sodium stibogluconate, it suggest that a small fraction of higher molecular weight components is mainly responsible for the PTPase inhibitory activity of sodium stibogluconate and might be purified as more potent and less toxic PTPase-targeted therapeutic.

Figure 3:
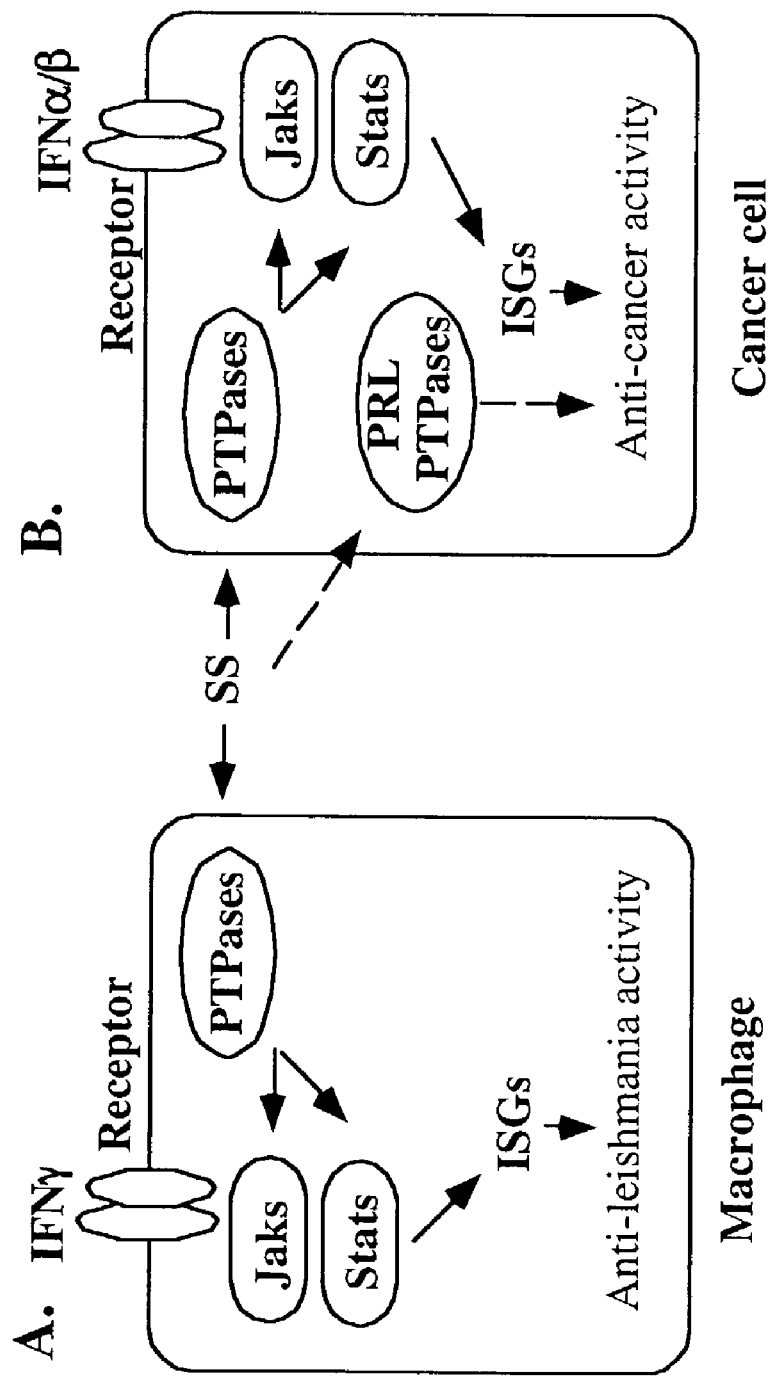
FIG. 3 illustrates a hypothetic mechanism of sodium stibogluconate as an anti-leishmania drug and an anti-cancer therapeutic: A. sodium stibogluconate inhibits PTPases down-regulating Jak/Stat to augment IFNα. PTPase inhibitory activity associates with selective higher molecular compounds in sodium stibogluconate. B. Sodium stibogluconate inhibits the PTPases to augment signaling of IFNα and their anti-cancer activity. sodium stibogluconate may also target other PTPases to mediate its anti-cancer activity as a single agent.

As shown in FIG. 3, signaling of IFNα is mediated by the Jak/Stat pathway. The cytokine activates Jak1 and Tyk2 kinases to phosphorylate Stat 1 and Stat2, which form ISGF3 with p48 to regulate the expression of ISGs that mediate the biological activities, including anti-cancer activity, of the cytokine. Tyrosine phosphorylation of the kinases and Stats correlates with their activities while their dephosphorylation by PTPases results in down-regulation of IFNα signaling. Since sodium stibogluconate is a PTPase inhibitor, its activity to augment the anti-cancer effect of IFNα is likely mediated sequentially by inactivating PTPases to 1) increase and/or prolong tyrosine phosphorylation of one or more of the signaling proteins; 2) increase and/or prolong ISGF3 activity; or 3) increase the expression of selective or all ISGs.

It is likely that sodium stibogluconate inactivates PTPases through covalent modification of the sulhydryl group in a cysteine residue conserved in all PTPases based on several lines of supporting evidence. This is demonstrated in FIG. 3A wherein sodium stibogluconate forms a stable complex and irreversibly inhibits PTPase PRL2 (it has also been shown for SHP-1). It was proposed, based on covalent bond formation between the pentavalent antimony in sodium stibogluconate with cellular proteins, that interactions of pentavalent antimony with key sulfhydryl groups of polypeptides may be a major mechanism of action. Importantly, the cysteine residue conserved in all PTPases plays a critical role in dephosphorylation and is the target of PTPase inhibitor pervanadate, which oxidizes the sulfhydryl group (—SH) of the residue to sulfonic acid (—$SO_3H$) thus blocking the formation of the phosphocysteine intermediate required for the dephosphorylation process. Therefore, sodium stibogluconate may inhibit PTPases via covalent modification of the sulfhydryl group in the cysteine residue with its carbohydrate moiety providing certain molecular configuration that brings the antimony into proximity of the cysteine residue at the catalytic pocket of PTPases. As the configuration of the catalytic pocket differs among PTPases, such a mode of action will also provide an explanation of the differential sensitivities of PTPases to the inhibitor. Consistent with this hypothesis, and as discussed below, glucatime (pentavalent antimony conjugated to carbohydrates from methylglucamine) was found to have PTPase inhibitory activity that acted against a different spectrum of PTPases compared to sodium stibogluconate (our unpublished data). Sodium stibogluconate therefore represents a new class of PTPase inhibitors that could be further developed as novel therapeutics and experimental tools.

Figure 3A:
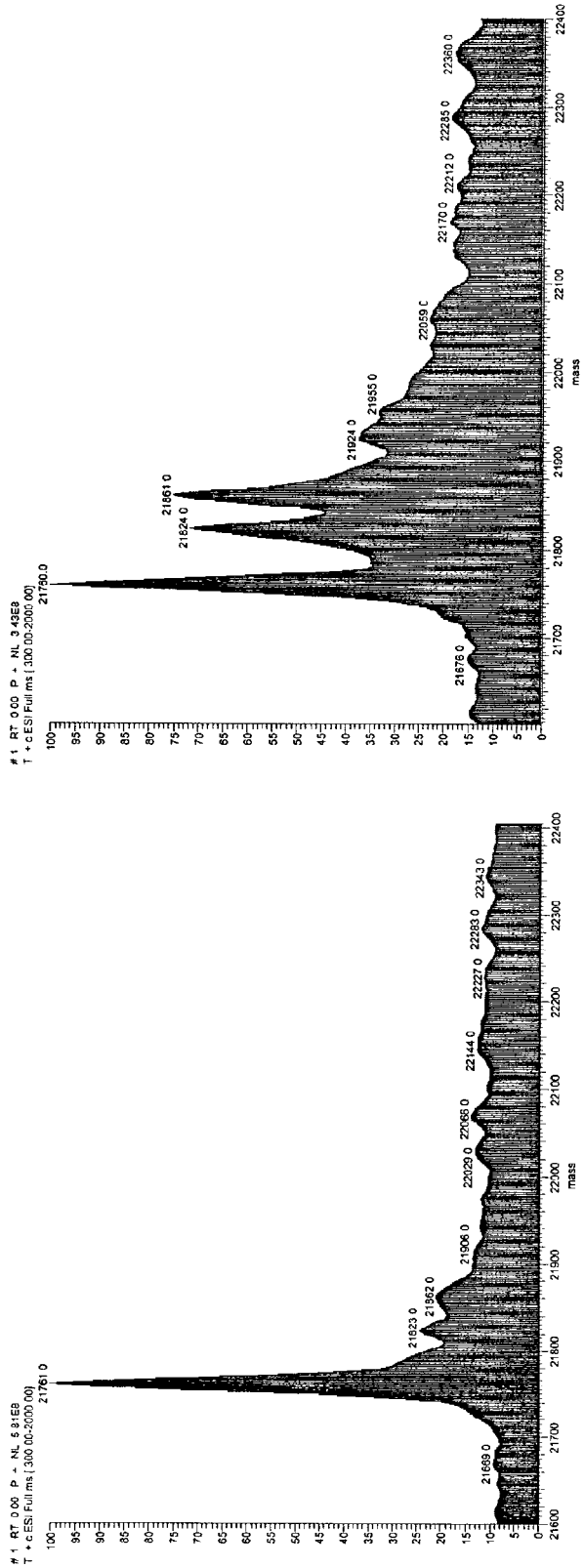
FIG. 3A illustrates the covalent modification of Recombinant PRL-2 by sodium stibogluconate.

While not wishing to be bound by theory, it appears sodium stibogluconate-induces covalent modification of SHP-1 in vitro by mass spectrometry. Again this principle is illustrated in FIG. 3A. Mass spectrometry has also been used to detect a similar modification of PTPases by pervanadate. SHP-1 is chosen as it is sensitive to and forms stable complex with the drug in vitro. It is also one of the potential sodium stibogluconate targets in vivo given its role in down regulating IFN-induced signaling in hematopoietic cells although its absence in WM9 cells indicated other PTPases for mediating sodium stibogluconate action against WM9 tumors. The catalytic domain of SHP-1 needed for the study has been purified and used in preliminary studies.

SHP-1 is protein tyrosine phosphatase that plays a pivotal role in down regulating signaling in hematopoietic cells. Deficiency of the phosphatase due to mutations in the SHP-1 gene associates with heightened signaling in hematopoietic cells and leads to hyperresponsiveness of hematopoietic cells to a variety of extracellular stimuli, including cytokines, hematopoeitic growth factors and antigens. Thus drugs targeting the enzyme may effectively modulate activation, proliferation and immune responses of hematopoietic cells for therapeutic purposes.

Protein tyrosine phosphatase assay kits and GST fusion protein of protein tyrosine phosphatase 1B (PTP1B) were purchased from Upstate Biotechnology Inc. (UBI, Lake Placid, N.Y.). Suramin and potassium antimonyl tartrate (PSbT) was purchased from Sigma (St. Louis, Mo.). Sodium stibogluconate (its Sb content is 100 mg/ml) was a gift from Dr. Xiaosu Hu (Sichuan Medical College, China). GST fusion proteins of SHP-1 and SHP-2 have been described previously and were prepared following established protocols. The GST fusion protein of SHP-1cata was purified from DH5a bacteria transformed with a pGEX construct containing the coding region of the PTPase catalytic domain (amino acid 202 to 554) of murine SHP-1, derived by PCR from the murine SHP-1 cDNA. The GST fusion protein of MKP1 was purified from DH5a bacteria transformed with a pGEX construct containing the coding region of MKP1 cDNA derived by RT-PCR using the following primers (MKP1/5, 5'ctggatc-ctgcgggggctgctgcaggagcgc; MKP1/3, 5'aagtcgacgcagcttggg-gaggtggtgat).

Murine IL-3, recombinant human GM-CSF and recombinant human IFNα have been described previously. Antibodies against phosphotyrosine (anti-ptyr, 4G10, UBI), β-actin (Amersham, Arlington Heights, Ill.), phosphotyrosine Stat5 (New England BioLab Inc, Beverly, Mass.) and Jak2 (Affinity BioReagents, Inc., Golden, Colo.) were purchased from commercial sources.

In vitro PTPase activities were measured using the commercial protein tyrosine phosphatase assay kit (UBI) following established procedure. This assay measures the in vitro dephosphorylation of a synthetic phosphotyrosine peptide (R-R-L-I-E-D-A-E-pY-A-A-R-G). Briefly, 0.01 μg of GST/PTPase fusion protein was incubated in 50 μl of Tris buffer (10 mM Tris, pH 7.4) containing different concentrations of inhibitors or chemicals (0 to 1,000 μg/ml) at 22° C. for 10 minutes, followed by addition of 0.2 mM of the phosphotyrosine peptide and incubation at 22° C. for 18 hours. 100 μl of Malachite Green solution was added and incubated for 5 minutes, and the absorbance at 660 nm was measured after 5 minutes.

To assess the reversibility of inhibition of SHP-1 by PTPase inhibitors, GST/SHP-1 fusion protein bound on glutathione beads were pre-incubated in cold Tris buffer or Tris buffer containing the PTPase inhibitors at 4° C. for 30 minutes. The beads were then washed 3 times in Tris buffer or without washing prior to in vitro PTPase assays.

The murine hematopoietic cell line Baf3 was maintained in RPMI 1640 medium supplemented with 10% fetal calf serum (FCS) and murine IL-3 (20 units/ml) as described previously. Human myeloid cell line TF-1 was maintained in RPMI 1640 supplemented with 10% FCS and 40 ng/ml of recombinant human GM-CSF as described previously. For cell proliferation assays, cells were washed in 10% FCS medium twice, resuspended in 10% FCS medium, incubated at 37° C. for 16 hours and then cultured at 37° C. in 10% FCS medium containing various amounts of cytokines, sodium stibogluconate, or PSbT for 3-6 days as indicated. The cell numbers in proliferation assays were determined by an MTT assay or by microscopic cell counting as indicated.

For induction of cellular protein phosphorylation by sodium stibogluconate or pervanadate, Baf3 cells were incubated in 0.1% FCS RPMI 1640 medium at 37° C. for 16 hours. The cells were then washed twice in RPMI 1640 medium and incubated with sodium stibogluconate or pervananadate (0.1 mM) for various times prior to termination by lysing cells in cold lysis buffer (50 mM Tris, pH 7.4; 150 mM NaCl; 0.2 mM Na3VO4; 20 mm NaF; 1% NP40; 2 mM PMSF; 20 μg/ml of aprotinin and 1 mM of sodium molybdic acid). To determine the effect of sodium stibogluconate or potassium antimonyl tartrate on IL-3-induced Jak/Stat phosphorylation, Baf3 cells were deprived of the growth factor for 16 hours in 0.1% FCS RPMI 1640 medium and then incubated with or without sodium stibogluconate or potassium antimonyl tartrate for 10 minutes. IL-3 was next added to the cell suspension and incubated for various times. The cells were then harvested and lysed in cold lysis buffer at 4° C. for 45 minutes. Total cell lysates (TCL) were separated in SDS-PAGE gels, blotted onto nitrocellulose membrane (Schleicher & Schuell), probed with specific antibodies and detected using an enhanced chemiluminescence kit (ECL, Amersham).

Figure 4:
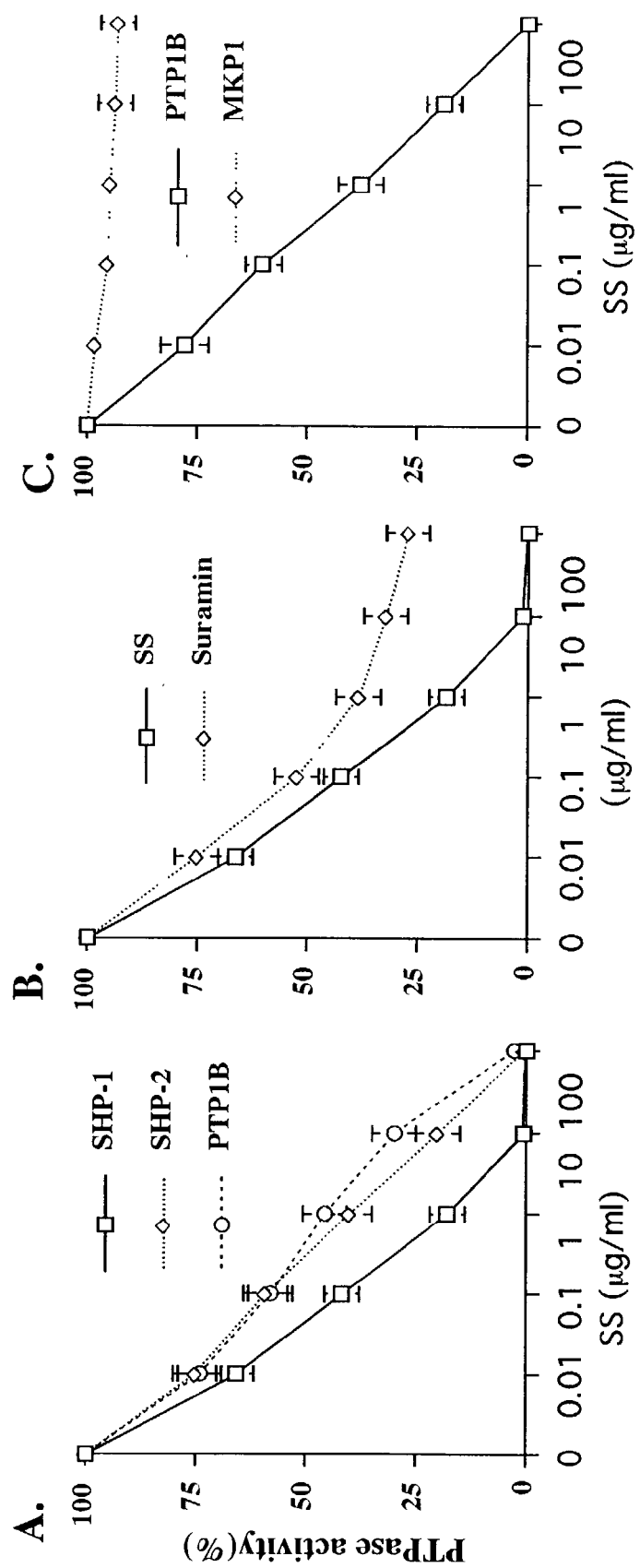
FIG. 4 illustrates that sodium stibogluconate inhibits PTPases in vitro. A. Relative PTPase activities of GST fusion proteins of SHP-1, SHP-2 and PTP1B in the presence of various amounts of sodium stibogluconate; B. Relative PTPase activities of GST/SHP-1 fusion protein in the presence of various amounts of sodium stibogluconate or suramin; C. Relative PTPase activities of GST fusion proteins of PTP1B and MKP1 in the presence of various amounts of sodium stibogluconate.

Through screening various chemical compounds by in vitro PTPase assays, sodium stibogluconate was identified as an inhibitor of PTPases. As shown in FIG. 4A, the dephosphorylation of a synthetic phosphotyrosine peptide by the GST/SHP-1 fusion protein was almost completely blocked (99%) by sodium stibogluconate at 10 μg/ml. Sodium stibogluconate also inhibited SHP-2 and PTP1B. However, approximately 10 fold higher concentrations of the drug (100 μg/ml) were required to achieve a similar degree (about 99%) of inhibition of the two PTPases (FIG. 4A). Inhibition of SHP-1 by the known PTPase inhibitor suramin was less effective under comparable conditions (FIG. 4B). The drug showed no obvious inhibitory activity against MKP1, a dual-specificity protein tyrosine phosphatase (FIG. 4C). Under the experimental conditions, the GST fusion proteins of SHP-1, SHP-2, PTP1B and MKP1 showed similar PTPase activities against the peptide substrate (OD 660 nm absorbance approximately 0.6 above background (0.03)) in the absence of inhibitors.

Figure 5:
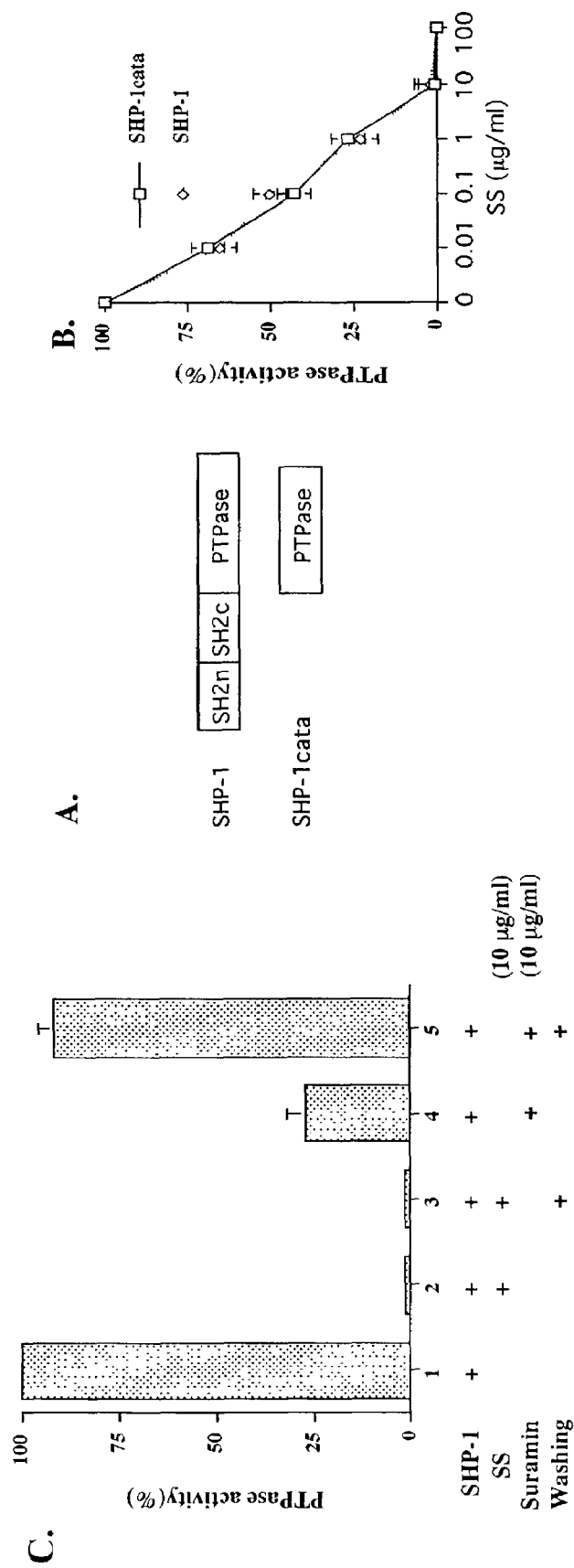
FIG. 5 illustrates that sodium stibogluconate forms stable complexes with SHP-1 in vitro: A. Protein domain structure of GST fusion proteins of SHP-1 and SHP-1 catalytic domain (SHP-1cata) which contains amino acid 202 to 554 of the wild type SHP-1 protein. B. Relative PTPase activities of GST fusion proteins of SHP-1 and SHP-1cata in the presence of various amounts of sodium stibogluconate. Relative PTPase activities of GST fusion protein of SHP-1 preincubated with sodium stibogluconate or suramin and then washed (+) or without washing (−) as indicated. Sodium stibogluconate targets the catalytic domain of SHP-1.

Substrate dephosphorylation is mediated by the PTPase catalytic domain, the activity of which is often regulated by flanking N-terminal and C-terminal regions. To define whether sodium stibogluconate inhibits PTPases through targeting the PTPase catalytic domain or via the flanking regulatory regions, we compared the effect of sodium stibogluconate on the GST/SHP-1 fusion protein and the GST/SHP-1cata fusion protein which contains the PTPase catalytic domain but has the SH2 domains and the C-terminal region deleted (FIG. 5A). Sodium stibogluconate showed similar activities in inhibiting the two proteins in their dephosphorylation of the phosphotyrosine peptide substrate in vitro (FIG. 5B), demonstrating that inhibition of SHP-1 PTPase activity by sodium stibogluconate does not require the SHP-1 SH2 domains and the C-terminal region. These results provide strong evidence that sodium stibogluconate directly targets the SHP-1 PTPase catalytic domain.

A functional role of SHP-1 in dephosphorylating the Jak family kinases during cytokine signaling has been documented. To determine whether sodium stibogluconate inhibits SHP-1 in vivo, the effect of the drug on IL-3-induced Jak2 tyrosine phosphorylation in Baf3 cells was examined. Baf3 cells deprived of IL-3 were incubated with or without the drug for 10 minutes and then stimulated with IL-3 for various times. IL-3 induced tyrosine phosphorylation of Jak2 and Stat5 in Baf3 cells in the presence or absence of the drug. However, the phosphotyrosine levels of Jak2 and Stat5 in the presence of the drug were about twice of those in cells without drug treatment as determined by densitometry analysis.

In cells unstimulated by IL-3, tyrosine phosphorylation of the two proteins was undetectable in the presence or absence of the drug. Prolonged incubation with the drug alone at 37° C. for 16 hours also failed to induce Jak2/Stat5 tyrosine phosphorylation.

SHP-1 is known to down-regulate cytokine signaling as demonstrated by the hyperresponsiveness of SHP-1-deficient cells to various cytokines, including IL-3. The inhibitory activity of sodium stibogluconate against SHP-1 predicted that the drug would augment IL-3-induced proliferation of Baf3 cells. Indeed, IL-3-induced Baf3 proliferation was increased in the presence of sodium stibogluconate at 0.3 to 200 µg/ml with the maximal effect concentration about 40 µg/ml. This modest increase was consistently detected in two separate experiments. At a higher concentration (1,000 µg/ml), the drug suppressed IL-3-induced Baf3 growth. This growth promoting activity of the drug was apparent at suboptimal (3.3 or 10 units/ml), but not optimal (30 unit/ml), amounts of IL-3. In the absence of IL-3, sodium stibogluconate failed to support cell proliferation or maintain cell viability in day 3 culture.

Sodium stibogluconate augments the opposite effects of GM-CSF and IFNα on the proliferation of TF-1 cells. The Jak/Stat signaling pathways transduce signals initiated by cytokines that often have opposite effects on cell growth. The human myeloid leukemia cell line TF-1 responds to both GM-CSF, which promotes proliferation, and IFNα, which inhibits cell growth. To determine whether the effect of the PTPase inhibitor is unique for the IL-3-initiated signaling events or affects other cytokines, we examined the growth responses of TF1 cells to GM-CSF and IFNα in the presence or absence of sodium stibogluconate.

Proliferation of TF-1 cells was induced by suboptimal concentrations of GM-CSF (5-40 ng/ml) in a dose-dependent manner. This proliferation of TF-1 cells was augmented in the presence of sodium stibogluconate at 50 µg/ml. No viable cells were detected in the cultures lacking GM-CSF in the presence or absence of the drug. These results demonstrated that sodium stibogluconate augmented the growth promoting activity of GM-CSF in TF-1 cells but could not substitute the growth factor for maintaining cell viability or promoting growth under the experimental conditions.

In the presence of IFNα, GM-CSF-induced proliferation of TF-1 cells was suppressed. Further reduction of GM-CSF-induced cell growth was detected in cultures containing both IFNα and sodium stibogluconate (50 µg/ml), indicating that the growth inhibition activity of IFNα was enhanced in the presence of the drug. Since the enhanced growth inhibition of IFNα by the drug occurred in the presence of GM-CSF, it indicated the dominance of the synergy between IFNα and the drug over the activity of the drug in augmenting GM-CSF mitogenic signaling under the experimental conditions.

The activity of sodium stibogluconate in augmenting GM-CSF-induced TF-1 proliferation was dose-dependent, with the optimal activity at 50 µg/ml. On the other hand, more dramatic growth inhibition in the presence of IFNα occurred at higher concentrations of the drug. Since the drug at low doses (12.550 µg/ml) showed no negative effect on GM-CSF-induced cell growth, its effect at such doses in augmenting IFN-induced growth inhibition was likely resulted from specific enhancement of IFN signaling. On the other hand, non-specific toxicity of drug at higher doses in combination with IFNα might have contributed to the more dramatic growth inhibition.

Sodium stibogluconate inactivates intracellular PRLs in NIH3T3 transfectants. The effects of sodium stibogluconate on intracellular PRL phosphatases were next investigated to determine whether sodium stibogluconate is an inhibitor of PRLs in vivo.

Figure 6A:
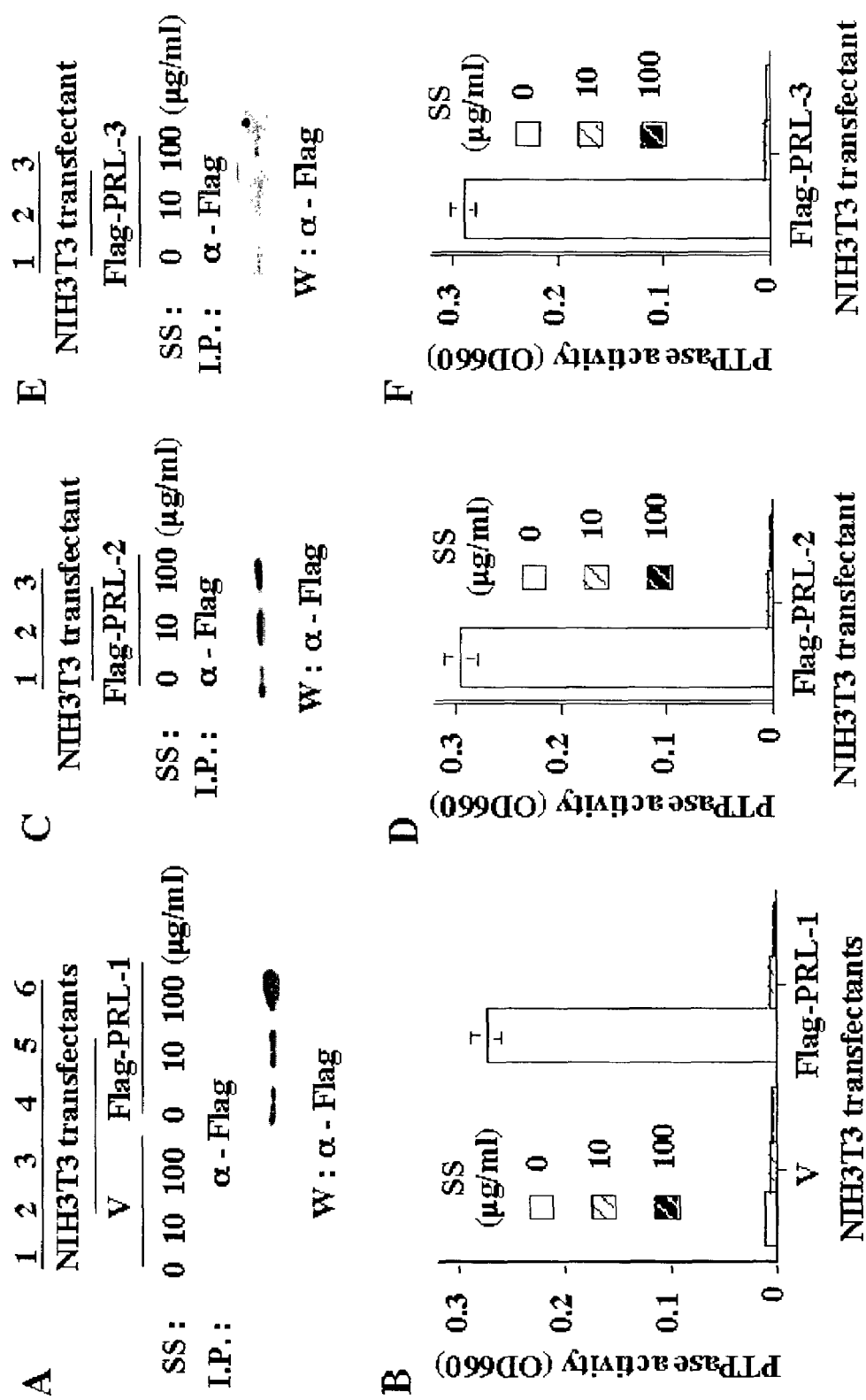
FIG. 6A. Sodium stibogluconate inactivates intracellullar PRLs in NIH3T3 transfectants. A. PTPase activities of anti-Flag immunocomplexes from untreated (0) or sodium stibogluconate-treated (5 min) NIH3T3 transfectants of the control vector (V) or Flag-PRL-1 expression construct in in vitro PTPase assays. B. Relative amounts of Flag-PRL-1 in the immunocomplexes as detected by SDS-PAGE/Western blotting. C. PTPase activities of anti-Flag immunocomplexes from untreated or sodium stibogluconate-treated NIH3T3 transfectants of Flag-PRL-2. D. Relative amounts of Flag-PRL-2 in the immunocomplexes as determined by SDS-PAGE/Western blotting. E. PTPase activities of anti-Flag immunocomplexes from untreated or sodium stibogluconate-treated NIH3T3 transfectants of Flag-PRL-3. F. Relative amounts of Flag-PRL-3 in the immunocomplexes as determined by SDS-PAGE/Western blotting.
Figure 6B:
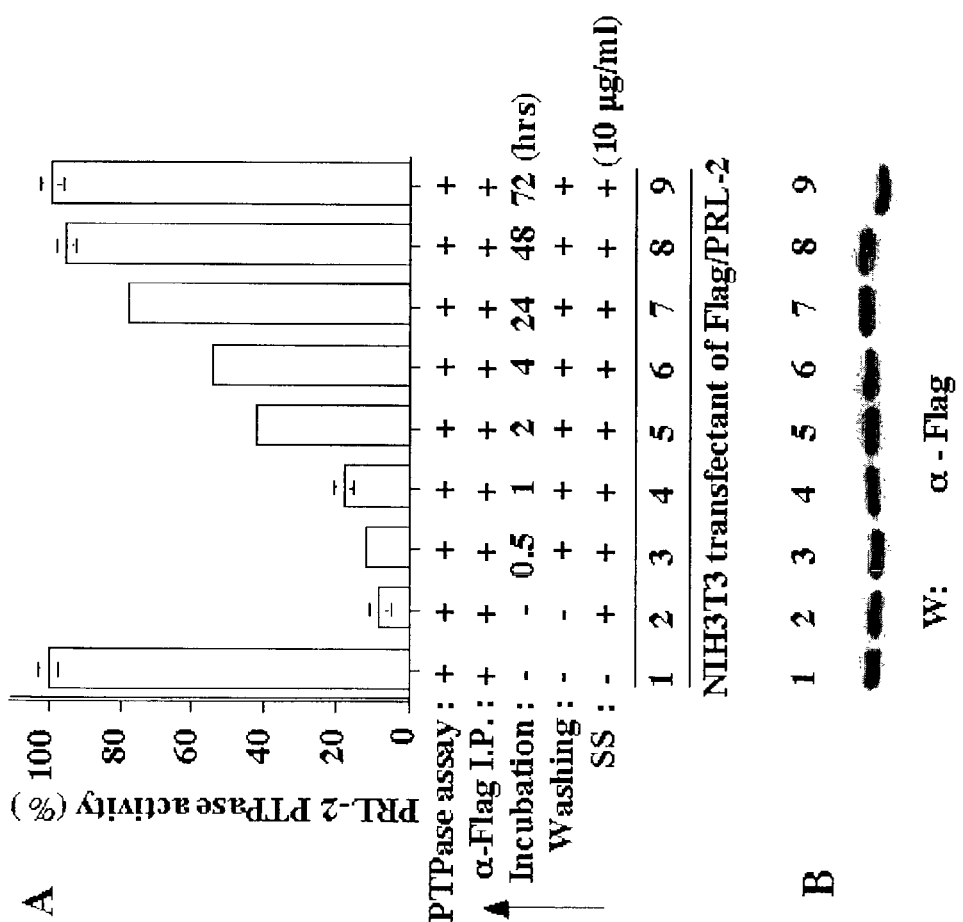
FIG. 6B. Duration of sodium stibogluconate-induced PRL-2 inactivation in NIH3T3 transfectants. A. Relative PTPase activity of anti-Flag immunocomplexes from Flag-PRL-2 transfectants untreated or treated with sodium stibogluconate for 5 min, washed to remove cell-free drug and then incubated for various times B. Relative amounts of Flag-PRL-2 in the immunocomplexes as determined by SDS-PAGE/Western blotting.
Figure 6C:
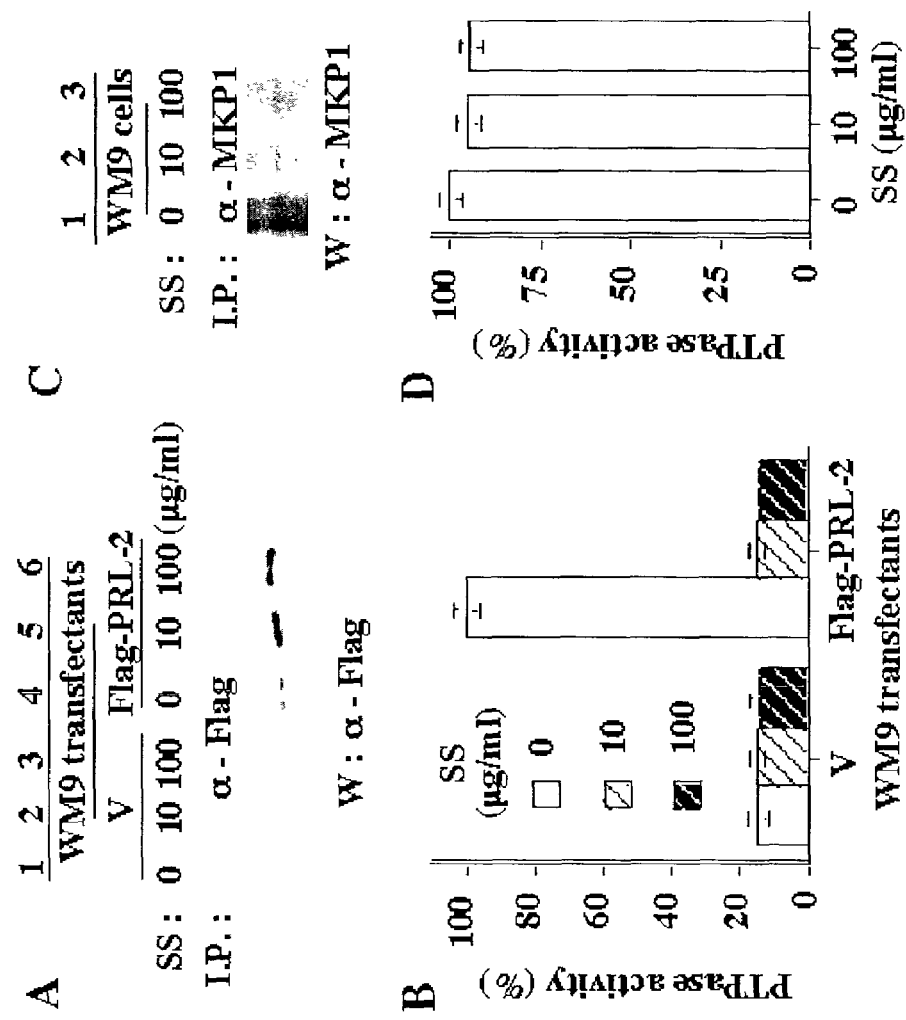
FIG. 6C. Sodium stibogluconate inactivates intracellular PRL-2 in WM9 human melanoma cells. A. Relative PTPase activities of anti-Flag immunocomplexes from WM9 cells transfected with the control vector (V) or Flag-PRL-2 expression construct and then treated with different amounts of sodium stibogluconate for 5 minutes B. Relative amounts of Flag-PRL-2 in the immunocomplexes as determined by SDS-PAGE/Western blotting. C. Relative PTPase activities of anti-MKP1 immunocomplexes from WM9 cells treated with different amounts of sodium stibogluconate for 5 minutes. Relative amounts of MKP1 in the immunocomplexes as determined by SDS-PAGE/Western blotting.
Figure 7:
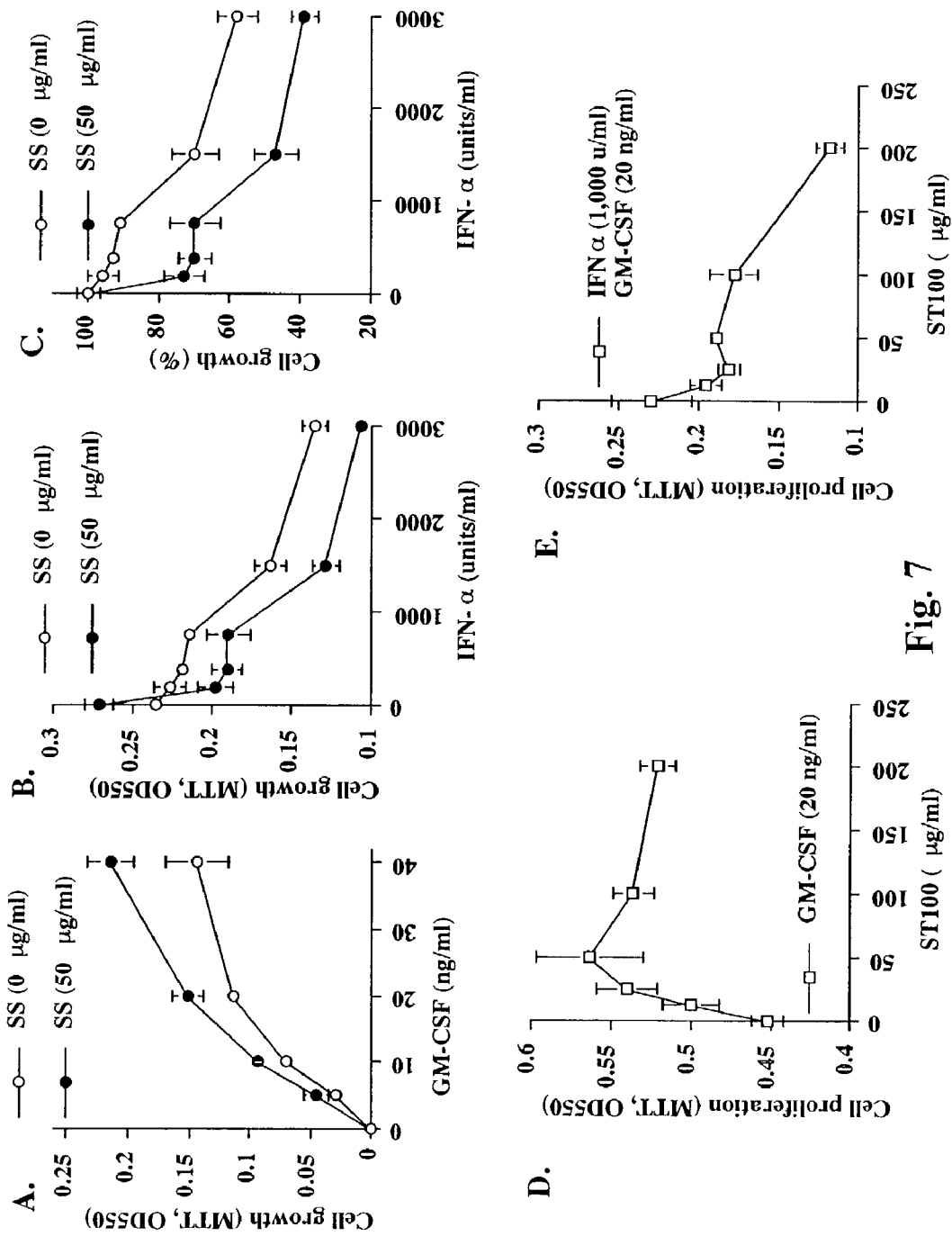
FIG. 7 illustrates that sodium stibogluconate augments the opposite effects of GM-CSF and IFNα on TF-1 cell growth: A. Proliferation of TF-1 cells cultured in the presence of various amounts of GM-CSF and with or without sodium stibogluconate for three days was measured by MTT assays; B. Proliferation of TF-1 cells cultured in the presence of GM-CSF (50 ng/ml) and various amounts of IFNα with or without sodium stibogluconate (50 µg/ml) for three days was measured by MTT assays; C. The results in B shown as percentage inhibition of cell growth; D. Proliferation of TF-1 cells in the presence of GM-CSF (20 ng/ml) and various amounts of sodium stibogluconate for 6 days was measured by MTT assays; E. Proliferation of TF-1 cells in the presence of GM-CSF (20 ng/ml)/IFNα (1,000 u/ml) and various amounts of sodium stibogluconate for 6 days was measured by MTT assays.
Figure 8:
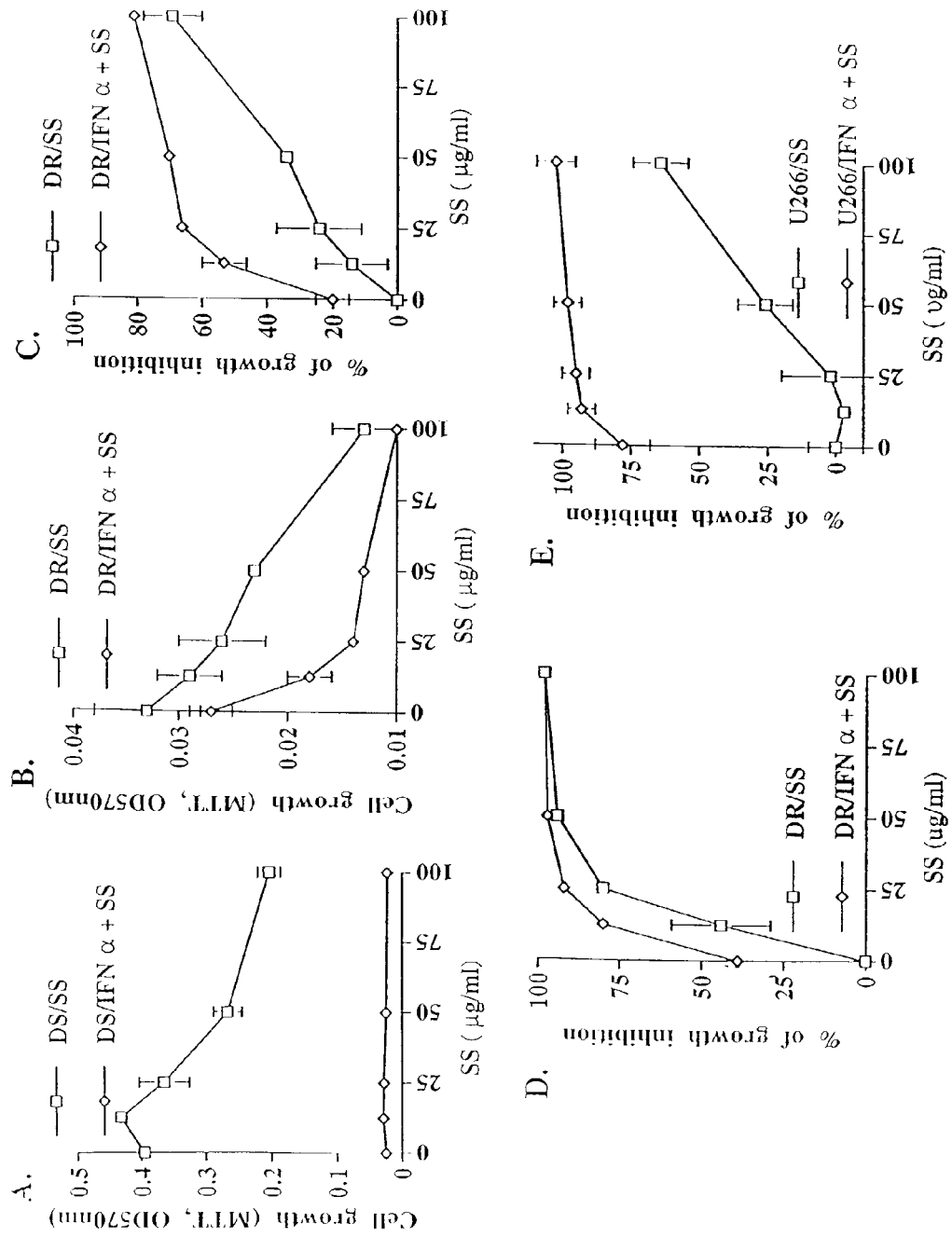
FIG. 8 illustrates growth inhibition of human cell lines of hematopoietic malignancies by sodium stibogluconate and/or IFNα: A and B. Growth of DS and DR cells cultured in the absence or presence of various amounts of sodium stibogluconate and/or IFNα (1,000 u/ml) for 3 days was measured by MTT assays; C. Percentage of growth inhibition of DR cells calculated from data in B; D. Percentage of growth inhibition of DR cells by IFNα (1,000 u/ml) and various amounts of sodium stibogluconate in day 6 cultures measured by MTT assays; E. Percentage of growth inhibition of U266 cells by IFNα (1,000 u/ml) and various amounts of sodium stibogluconate in day 6 cultures as measured by MTT assays.

An expression construct of Flag-tagged PRL-1 or control vector was transfected into NIH3T3 cells which were then treated without or with sodium stibogluconate and used for immunoprecipitation assays with a monoclonal anti-Flag antibody. The immunocomplexes were analyzed by SDS-PAGE/Western blotting and PTPase assays. A Flag-tagged protein with a molecular weight approximately 22 kDa as expected for Flag-PRL-1 was detected in the immunocomplexes from untreated or sodium stibogluconate -treated Flag-PRL-1 transfectants but not in those from the control cells (FIG. 6A). Immunocomplexes from untreated Flag-PRL-1 transfectants showed a markedly higher PTPase activity(~23 folds) over that of control transfectants (FIG. 6B). In contrast, immunocomplexes from sodium stibogluconate-treated Flag-PRL-1 transfectants had little PTPase activities that were at levels similar to those of the control cells (FIG. 6B). Such a lack of PTPase activity was also evident in the immunocomplexes from sodium stibogluconate -treated NIH3T3 transfectants of Flag-PRL-2 or Flag-PRL-3 although Flag-tagged PRLs were present at similar levels in the immunocomplexes from the untreated or sodium stibogluconate -treated cells (FIG. 6).

These results demonstrated that sodium stibogluconate treatment inactivated intracellular PRLs in the transfectants, indicating that sodium stibogluconate is an effective inhibitor of PRL phosphatases in vivo.

sodium stibogluconate induces prolonged PRL-2 inactivation in NIH3T3 transfectants.

In light of the observation that sodium stibogluconate inactivates intracellular PRLs, the issue of the duration of sodium stibogluconate -induced inactivation of PRLs was addressed. Since sodium stibogluconate was equally effective against each of the PRLs (FIG. 6A), the duration of sodium stibogluconate -induced inaction of a single PRL in NIH3T3 transfectants was determined.

Flag-PRL-2 transfectants were briefly treated with sodium stibogluconate for 5 minutes, washed to remove cell-free drug and then incubated for various times prior to termination by cell lysis. Anti-Flag immunocomplexes from the cells were analyzed by SDS-PAGE/Western blotting and PTPase assays. The amounts of Flag-PRL-2 proteins in the immunocomplexes were at similar levels as quantified by probing with an anti-Flag antibody. Immunocomplexes from cells treated with sodium stibogluconate showed a markedly reduced PTPase activity in comparison to that from the control, consistent with inactivation of PRL-2 by sodium stibogluconate treatment. Immunocomplexes from cells incubated for different times following sodium stibogluconate-treatment and cell washing showed a gradual increase of PTPase activity in a time-dependent manner above the level of sodium stibogluconate-treated cells. PTPase activity of the immunocomplexes from cells incubated for 24 hours was 78% of the untreated cells. Immunocomplexes from cells incubated for 4872 hours showed PTPase activities similar to that of the untreated cells.

These results demonstrated a prolonged inhibitory effect of the brief sodium stibogluconate treatment on intracellular PRL-2 activity that required at least 24 hours for its full removal in NIH3T3 transfectants.

Sodium stibogluconate inactivates intracellular PRL-2 but not MKP1 in WM9 human melanoma cells. Sodium stibogluconate showed striking activity against WM9 human melanoma cells in vitro and WM9 tumors in mice. These observation prompted us to further investigate whether sodium stibogluconate functions as a PTPase inhibitor in WM9 cells. For this, we determined the effects of sodium stibogluconate on the PTPase activity of Flag-PRL-2 phosphatase and MKP1 phosphatase in WM9 cells.

Flag-PRL-2 protein was detected in anti-Flag immunocomplexes from WM9 cells tranfected with an expression construct of Flag-PRL-2 but not in those from vector transfectants expected. Immunocomplexes from untreated Flag-PRL-2 transfectants showed significant PTPase activity in comparison to that of the control. However, immunocomplexes from sodium stibogluconate-treated Flag-PRL-2 transfectants had only low levels of PTPase activity similar to the background of the control, demonstrating inactivation of Flag-PRL-2 in sodium stibogluconate-treated WM9 cells. In contrast, MKP1 immunoprecipitated from untreated or sodium stibogluconate-treated WM9 cells showed similar PTPase activity, indicating that sodium stibogluconate had no marked effects on MKP1 PTPase activity in the cancer cells.

These results demonstrated that sodium stibogluconate functioned as a specific inhibitor against PRL-2 but not MKP1 in the human cancer cells. Given the oncogenic activity of PRLs, their inaction in cancer cells by sodium stibogluconate could be an important mechanism of sodium stibogluconate anti-cancer activity. The fact that MKP1 was not inactivated by sodium stibogluconate in the cancer cells provides evidence that sodium stibogluconate acts against only selective PTPase in vivo. It also demonstrates a correlation between sodium stibogluconate inhibitory activity in vitro and in vivo. PTPases (e.g., PRLs) sensitive to sodium stibogluconate inhibition in vitro are also sensitive to the inhibitor in vivo while the ones (e.g., MKP1) insensitive the sodium stibogluconate in vitro are not inhibited by the drug in vivo.

Sodium stibogluconate is of Sb-V form which transforms inside cells into Sb-III form that can affect leishmania growth. Therefore, the activity of potassium antimonyl tartrate (PSbT) of Sb-III form in inhibiting PTPases in vitro and in vivo was deformed. Unlike sodium stibogluconate, PSbT at 11,000 µg/ml showed no detectable inhibition of PTPases SHP-1 and PTP1B in vitro. It also failed to enhance IL-3-induced Stat5 phosphorylation or IL-3-induced proliferation of Baf3 cells, indicating its lack of inhibitory activity against PTPases in vivo. Interestingly, it showed marked toxicity against Baf3 cells. The results together indicate that only the Sb-V form acts as a PTPase inhibitor which is inactivated when transformed into the Sb-III form.

The presented data provide the first evidence that sodium stibogluconate is a potent inhibitor of protein tyrosine phosphatases in vitro and in vivo. Sodium stibogluconate inhibited the dephosphorylation of a synthetic phosphotyrosine peptide substrate by protein tyrosine phosphatases (SHP-1, SHP-2 and PTP1B) in in vitro PTPase assays. The dephosphorylation of pNPP (p-nitrophenyl phosphate, Sigma) by these PTPases in vitro was also similarly inhibited by the drug. The inhibitory activity of the drug against PTPases in vivo was indicated by the rapid induction of protein tyrosine phosphorylation of the two yet-unidentified cellular proteins of 56 and 32 kDa in Baf3 cells. Interestingly, proteins of similar molecular weights had been found to be hyperphosphorylated in SHP-1 deficient cells in previous studies. Induced cellular protein tyrosine phosphorylation was less dramatic with prolonged drug incubation, suggesting that the drug may be unstable under the experimental conditions or that the drug may sequentially inactivate PTPases with opposite effects on the phosphorylation of the cellular proteins. In this regard, it is interesting that PTPases were inhibited by the Sb-V form of sodium stibogluconate which is known to transform in cells to the Sb-III form that failed to show PTPase inhibitory activity. The intracellular transformation therefore could result in inactivation of the PTPase inhibitor and may account for the drug's modest and transient induction of tyrosine phosphorylation and modest effect on cell proliferation. This may have a beneficial side as it may be related to the lower toxicity of the drug in comparison to other PTPase inhibitors that allows its clinical application.

The inhibitory activity of sodium stibogluconate against PTPases in vivo was further indicated by the augmentation of IL-3-induced Jak2/Stat5 phosphorylation and IL-3-induced proliferation of Baf3 cells. It was previously shown that SHP-1 dephosphorylates the Jak family kinases to down regulate signaling initiated by cytokines. Among the Jak kinases, IL-3 specifically activates the Jak2 kinase which phosphorylates the Stat5 protein to regulate gene expression. The observation that sodium stibogluconate augmented IL-3-induced Jak2/Stat5 tyrosine phosphorylation and IL-3-induced proliferation of Baf3 cells is therefore consistent with inhibition of SHP-1 by the drug in vivo. However, it remains possible that the effect of the drug on IL-3-induced Jak2/Stat5 phosphorylation and cell proliferation involves additional PTPases (e.g., the CD45 PTPase) that participate in dephosphorylating the Jak kinases. Indeed, sodium stibogluconate augmented G-CSF-induced Tyk2/Stat3 tyrosine phosphorylation in SHP-1-deficient cells. The enhancement of IL-3-induced Jak2/Stat5 tyrosine phosphorylation by the drug was more dramatic in later time points post IL-3 stimulation, indicating induction of extended period of phosphorylation by the drug. Such an effect of the drug suggests its targeting of PTPases recruited to Jak2/Stat5 at the later time points post IL-3 stimulation to inactivate the signaling molecules.

Inhibition of PTPases in vivo by sodium stibogluconate was also consistent with the observation that the drug augmented the opposite effects of GM-CSF and IFNα on TF-1 cell proliferation. In particular, the observation suggested that the drug targeted PTPases which dephosphorylate shared signaling molecules (e.g., the Jak family kinases) utilized by both GM-CSF and IFNα. Such a putative mechanism would explain the cytokine-dependent effects of the drug: its inhibition of PTPases leads to amplification of both mitogenic and growth inhibitory signals initiated by GM-CSF and IFNα, respectively. It also suggests that drug may have broad activities in augmenting the signaling of various cytokines. It is worth noticing that SHP-1 has been shown in previous studies to down regulate the signaling of GM-CSF and IFNα. It was reported that macrophages from SHP-1-deficient mice show approximately 2 fold increase of GM-CSF-induced cell growth in comparison to controls. This level of growth increase is similar to the increase of GM-CSF-induced TF-1 cell growth in the presence of sodium stibogluconate, consistent with inhibition of SHP-1 by the drug. In light of the pathogenic effect of SHP-1-deficient monocytes/macrophages in the fatal motheaten phenotype, it is possible that the apparently modest effect of the drug on GM-CSF-induced cell growth could have significant biological consequences in vivo.

The results also suggest that inhibition of PTPases by sodium stibogluconate at therapeutic concentrations to increase Jak/Stat phosphorylation and cellular responses to cytokines may be a major factor responsible for the pharmacological effect of the drug in the treatment of leishmaniasis. Among the cytokines that depend on Jak/Stat pathways for signal transduction, IFN-γ plays an important role in eliminating intracellular leishmania. Moreover, impaired IFN-γ signaling was detected in leishmania-infected macrophages and was associated with activation of SHP-1 by the parasite. Therefore, it could be postulated that sodium stibogluconate may augment IFN-γ signaling in macrophages via inhibiting SHP-1 (and other PTPases) and contribute to the clearance of intracellular leishmania.

The mechanism through which the drug inhibits PTPases is likely by targeting the PTPase catalytic domain of the enzymes. The drug was effective in inhibiting both the wild type SHP-1 and the SHP-1 mutant containing the PTPase domain without the flanking N-terminal SH2 domains or the C-terminal region that regulate SHP-1 activity. This mechanism is also consistent with the observation that the drug inhibited PTP1 B which, except for its PTPase catalytic domain, has no apparent structure similarity with SHP-1 and SHP-2. In this regard, it is not unexpected that the drug showed no obvious activity against MKP1 since the amino acid sequence and structure of the catalytic domain of dual specificity phosphatases are substantially different from those of the tyrosine specific PTPases. Such a mechanism also suggests that the drug may have inhibitory activities against all tyrosine specific PTPases that have the conserved PTPase catalytic domain. Results of our studies provide novel insights into the anti-cancer mechanisms of sodium stibogluconate that involves inactivation of different PTPases in cancer cells. The ability of sodium stibogluconate to synergize with IFNs is likely mediated by inactivation of PTPases regulating the Jak/Stat pathway, resulting in augmentation of IFN signaling. sodium stibogluconate enhanced IFNα-induced Stat1 phosphorylation that coincided with its inhibition of intracellular SHP-1 and SHP-2 in cancer cells. Since both of the PTPases are known to be negative regulators of IFN signaling, their inhibition by sodium stibogluconate in cancer cells would result in augmentation of IFN-induced signaling and IFN anti-cancer activity. Such a mode of action is also consistent with the observation that sodium stibogluconate as a single agent inhibited the growth of 5637 bladder cancer cells but failed to interact with IFNα against these cells in which IFN signaling pathway has a defect down stream of Jak/Stat molecules. In contrast, the anti-cancer activity of sodium stibogluconate as a single agent functioned independently of IFNα signaling and its negative regulatory PTPases since sodium stibogluconate alone failed to induce Stat1 tyrosine phosphorylation. The ability of sodium stibogluconate as a single agent to increase cellular protein tyrosine phosphorylation in WM9 cells suggests that sodium stibogluconate might inactivate other PTPases that mediate its anti-cancer activity as a single agent. Further studies to characterize the sodium stibogluconate—inducible phosphotyrosine proteins will help to elucidate the mechanism.

Our finding that sodium stibogluconate is a potent and clinically usable inhibitor of PTPases with anti-cancer activity opens up potential new research areas for further mechanistic studies and for the development of more specific and effective PTPase inhibitors as targeted therapeutics. Sodium stibogluconate is a heterogeneous mixture of pentavalent antimony conjugated to carbohydrates from gluconic acid. The ability of antimony to form covalent bonds with sulfhydryl group and the existence of a conserved active site cysteine residue in catalytic pockets of all tyrosine phosphatases suggest involvement of modification of the cysteine residue by pentavalent antimony in sodium stibogluconate as an inactivation mechanism. Since only selective higher molecular weight compounds in sodium stibogluconate were effective as PTPase inhibitors (FIG. 6), it suggests that only antimony conjugated with carbohydrates in a specific configuration may gain assess to the PTPase catalytic pockets and allow optimal antimony/cysteine interaction, resulting in modification of the cysteine residue and PTPase inactivation. Such an inhibitory mechanism could provide a rational explanation for the differential sodium stibogluconate-sensitivities of PTPases, each of which possesses a catalytic pocket of unique geometry for specific interaction with its substrates. It might therefore be feasible to develop more specific and effective inhibitors as phosphatase-targeted anti-cancer therapeutics through screening of sodium stibogluconate-related chemical compounds comprised of antimony conjugated to different organic moieties. Consistent with this hypothesis, glucatime (pentavalent antimony conjugated to carbohydrates from methylglucamine) was found to have PTPase inhibitory activity that acted against a different spectrum of PTPases compared to sodium stibogluconate (our unpublished data). Sodium stibogluconate may therefore represent a new class of PTPase inhibitors that could be further developed as novel therapeutics and experimental tools.

Our observation that the PTPase inhibitory activity of sodium stibogluconate predominantly associated with a small fraction (<10%) of the total compounds in the drug and could be separated from most of the inactive ones based on its higher molecular weight is also significant in further development of sodium stibogluconate as a novel anti-cancer drug. Interestingly, some lots of sodium stibogluconate with diminished polymerization as indicated by higher osmolalities were reported to have markedly increased toxicity and poor clinical outcomes, suggesting that lower molecular weight compounds in sodium stibogluconate are mainly responsible for the drug's toxicity and possess little therapeutic activity. These observations together suggest that the higher molecular weight compounds purified from sodium stibogluconate might be less toxic and more potent as PTPase-targeted therapeutic for cancer treatment. The procedures developed in this study to separate sodium stibogluconate based differential molecular weights of the compounds provide a basis for further investigation in this regard.

Demonstrated differential sensitivities of PTPases to the drug in vitro suggest similar differential sensitivities of PTPases in vivo, which may explain the dose-dependent effect of the drug on IL-3-induced cell proliferation and the known clinical side effect of the drug at higher dosages. Sodium stibogluconate augmented IL-3-induced Baf3 proliferation at therapeutic concentrations and suppressed cell growth at higher dosages. Effects of the drug at higher dosages may be related to inhibition of PTPases that are only sensitive to the drug at higher concentrations.

Importantly, the finding that sodium stibogluconate was a potent inhibitor of PTPases and an enhancer of cytokine signaling suggest potential novel clinical applications for the drug in a variety of situations in which increased cytokine responses are beneficial. It is tempting to speculate co-administration of the drug with cytokines will improve the efficacy of existing cytokine therapies and reduce side effects and costs associated with cytokine therapies. Moreover, the drug by itself may have therapeutic effects through inhibiting PTPases to change the balance of intracellular tyrosine phosphorylation that controls cell proliferation, differentiation and functional activities. In this regard, it is worth noticing that suramin is presently being evaluated in clinical trials for the treatment of prostate cancer and other solid tumors. As sodium stibogluconate appeared to be a more efficient inhibitor of PTPases than suramin, it has the potential to become a better drug for effective treatment of these diseases.

PTPase inhibitor sodium stibogluconate induces differentiation of human myeloid leukemia cell lines in vitro. Acute myeloid leukemia (AML) is characterized by the accumulation of myeloid blast cells that are arrested at various differentiation stages and unable to terminally differentiate. Based on morphology, cytochemistry, immunological markers, and cytogenetics, AML can be divided into distinct subclasses according to the French-American-British (FAB) classification. Treatment for most subclasses of AML is unsatisfactory. It usually includes intensive chemotherapy administered as induction treatment to induce complete hematological remission and consolidation therapy to eradicate residual disease. Consolidation therapy with chemotherapy alone or in combination with autologous stem cell transplantation is associated with a relatively high risk of relapse and a longterm disease-free survival of less than 50%. Consolidation therapy with allotransplantation has a lower relapse risk but a higher treatment-related mortality.

Potential of differentiation induction therapy in AML treatment is highlighted by the recent success of all-trans-retinoic acid (ATRA) in the treatment of acute promyelocytic leukemia (APL, M3 subclass). All-trans-retinoic acid (ATRA), nitroblue tetrazolium (NBT), and 12-O-tetradecanoylphorbol-13-acetate (TPA) were purchased from Sigma (Sant Louis, Mo.). Sodium stibogluconate and recombinant human GM-CSF have been described previously. ATRA has been shown to induce complete remission and increased long term APL-free survival exceeding 75%. This therapeutic effect of ATRA derives from its activity in inducing terminal differentiation of APL cells through its binding to aberrantly generated chimeric proteins of retinoic acid receptor a (RARα) that results in degradation of the chimeric proteins and altered transcription regulation. As generation of chimeric proteins of RARα is restricted to APL cells, differentiation induction therapy with ATRA showed only limited benefit in the treatment of other AML subclasses. Moreover, ATRA differentiation induction therapy works well only in a subset of APL cases with translocation but showed little or no effect on those with translocation. Therapeutic use of ATRA is further compromised by serious systemic toxicity and induced ATRA resistance. Nevertheless, the marked success of ATRA in the subgroup of APL cases has provided evidence indicating the efficacy of differentiation induction therapy in AML treatment and prompted extensive efforts to identify other differentiation induction therapeutics. Several candidates were reported recently, including arsenic derivatives and histone deacetylase inhibitors. Although a number of hematopoietic growth factors and cytokines used alone or in combination with other reagents are known to promote mycloid differentiation, their clinic usage in AML treatment is controversial due to marked variations in the responses of AML cells to the ligands.

Several lines of evidence have indicated that AML cell differentiation is affected by cellular protein tyrosine phosphorylation regulated by the balance of protein tyrosine kinases (PTKs) and protein tyrosine phosphatases (PTPases). Granulocytic maturation of HL-60 promyelocytic leukemia cells was shown to produce a decrease in cellular protein tyrosine phosphorylation and increases in both tyrosine kinase and protein phosphotyrosine phosphatase activities. HePTP amplification and overexpression were found in AML cells and cell lines and may contribute to abnormal AML cell growth and arrest of differentiation. The involvement of hematopoictic cell phosphatase SHP-1 was indicated by its increased expression during HL-60 cell differentiation and its inhibition of Epo-induced differentiation of J2E leukemic cells. Interestingly, PTK inhibitor STI571 was shown to enhance ATRA-induced differentiation of APL cells although it alone had no differentiation induction activity. So far, induction of AML cell differentiation by PTPase inhibitors has not been reported.

Cell lines, cell culture, and cell proliferation assay. The NB4 cell line was a gift from Dr. Dan Lindner of CCF. HL60 and U937 cell lines were purchased from ATCC. These human AML cell lines were maintained in RPMI 1640 medium supplemented with 10% fetal calf serum (FCS). For cell proliferation assays, cells were cultured at 37° C. in 10% FCS medium containing various amounts of sodium stibogluconate for 6 days. The cell numbers in the cultures were determined by an MTT assay as described previously.

Differentiation of AML cell lines was assessed by their ability to produce superoxide as measured by reduction of NBT to formazan and by analysis of expression of CD11b surface marker by flow cytometry. For NBT reduction, each cell suspension was mixed with an equal volume of solution containing 1 mg/ml of NBT (Sigma) and 2.5 μg/ml of TPA for 30 minutes at 37° C. After incubation, cells containing the purple formazan deposits and cells devoid of NBT-reducing activity (white cells) in each sample were determined by counting 200 cells under microscope. We expressed the data as percentage of the following ratio: purple cells/purple+ white cells. For analysis of cell surface antigens, cells were exposed to phycoerythrin (PE)–conjugated murine anti-human CD11b (DAKO corp, Carpinteria, Calif.). Analysis of fluorescence was performed on a FACScan flow cytometer (Beckton Dickinson, Mountain View, Calif.). The cell cycle was analyzed by flow cytometry after 3 days of culture of NB4 cells in the absence or presence of sodium stibogluconate (250 μg/ml) or ATRA (1 μM). Briefly, the cells were fixed in cold ethanol and incubated for 30 minutes at 4° C. in the dark with a solution of 50 mg/ml propidium iodide, 1 mg/ml RNase and 0.1% NP-40. Analysis was performed immediately after staining using the CELLFIT program (Becton Dickinson, Mountain View, Calif.).

Detection of apoptotic cells by Annexin V/propidium iodide assay. Annexin V staining of exposed membrane phospholipid phosphatidylserine (PS) was done using the Annexin V assay kit (Pharmingen, San Diego, Calif.). Briefly, NB4 cells were cultured in the 10% FCS RPMI 1640 medium in the absence or presence of sodium stibogluconate (250 μg/ml) or ATRA (1 μM) for 3 days. Cells were then washed in PBS twice and stained in binding buffer (10 mM Hepes, pH 7.4; 140 mM NaCl; 2.5 mM CaCl2) containing Annexin V-FITC and propidium iodide for 15 min. The reaction was stopped by adding 10 volumes of binding buffer and analyzed by FACS (Becton Dickinson Facsvantage).

Sodium stibogluconate induces differentiation of AML cell line NB4 in a dose- and time-dependent manner. Sodium stibogluconate induced NB4 cell differentiation in dose- and time-dependent manner as indicated by the increase of NBT positive cells in the presence of the drug. Sodium stibogluconate-induced NB4 cell differentiation is associated with cell growth arrest at S phase and increased cell death. Proliferation of NB4 cells was markedly inhibited in the presence of sodium stibogluconate at all the dosages that were examined (12.5-400 μg/ml). Cell DNA content analysis showed a significant increase of cells at S phase in the NB4 cells treated with sodium stibogluconate (250 µg/ml) for 3 days. In contrast, NB4 cells cultured in the presence of ATRA (1 µM) for 3 days were arrested at G1 phase. These results demonstrated that sodium stibogluconate induced NB4 cell growth arrest at S phase and had a cytotoxic effect against the cells.

Our results suggest that sodium stibogluconate may be effective in inducing differentiation of AML cells of different FAB classes. This is indicated by its differentiation induction activity in the AML cell lines that represent M3 (NB4 and HL-60) and M5 (U937) subclasses. It is supported by its effect in inducing differentiation of human AML cell line AML-3, which represents the M2 subclass. Since sodium stibogluconate is a PTPase inhibitor, it is expected that sodium stibogluconate induces differentiation via directly targeting a PTPase or PTPases in AML cells. Such a mechanism apparently functions independently of the PML/RARα chimeric protein, a major target of ATRA that is degraded in ATRA-treated NB4 cells. This is evident as sodium stibogluconate had no detectable effect on the expression levels of PML/RARα chimeric protein in NB4 cells and did not synergize with ATRA in differentiation induction. This distinct mechanism of sodium stibogluconate in differentiation induction suggests that sodium stibogluconate may be particularly useful in AML cases unresponsive or developed resistance to ATRA treatment.

It is likely that the key sodium stibogluconate target in AML differentiation is among the PTPases that are relatively insensitive to the drug. This is based on the previous observation of differential sensitivities of PTPases to the inhibitor, with complete inhibition of sensitive PTPases (e.g., SHP-1) by sodium stibogluconate at 10 µg/ml and a similar inhibition of insensitive PTPases at more than 100 µg/ml. And it is supported by the data presented here that the optimal dosage of sodium stibogluconate in inducing AML cell differentiation is at levels more than 100 µg/ml. In this regard, the involvement of amplification and over expression of HePTP in AML is interesting and suggests the PTPase as a candidate target of the drug. Characterization of PTPase expression profiles of sodium stibogluconate-sensitive and sodium stibogluconate-resistant AML cell lines will help to identify the putative PTPase target in AML differentiation.

The optimal dosage of sodium stibogluconate for inducing differentiation of NB4 and HL-60IU937 cells is 250 82 g/ml and 400 µg/ml respectively. The standard dosage for leishmania treatment is 10-20 mg/kg/day resulting in 10 µg/ml or more serum levels. However, higher drug dosages may be clinically achievable and tolerated since doses as high as 80-143 mg/kg had been used in leishmania treatment. Nevertheless, even standard dosage of sodium stibogluconate may have certain therapeutic benefit as the drug at lower dosages (e.g., 10 µg/ml) showed differentiation induction activity in AML cells. Further studies using mouse models of AML are needed to verify the differentiation induction activity of the drug and to determine the toxicity of the drug at the optimal dosages in vivo.

The observation that GM-CSF augments sodium stibogluconate-induced differentiation of HL-60 and U937 suggest the potential clinical use of the two reagents in combination in AML treatment. Such an interaction between sodium stibogluconate and GM-CSF is not unexpected given the activity of the drug in augmenting GM-CSF signaling and the biological effect of the cytokine on mycloid cells. However, combination usage of sodium stibogluconate and GM-CSF may only benefit a subgroup of AML cases as a positive interaction between the two reagents in differentiation induction was not detected in NB4 cells, which were not responsive to the cytokine. Moreover, sodium stibogluconate may also interact with other cytokines in differentiation induction of AML cells. G-CSF and IFNs were reported to potentiate differentiation of AML cells. Like GM-CSF, the two cytokines signal through the Jak/Stat pathway that could be augmented by sodium stibogluconate.

The demonstrated activity of sodium stibogluconate in inducing differentiation of AML cells also suggests the potential of other PTPase inhibitors in inducing AML cell differentiation and in differentiation induction therapy for AML. While most of the known PTPase inhibitors (e.g., sodium vanadate and sodium iodo-acetic acid) are toxic and less appealing for clinical application, a number of newly identified PTPase inhibitor are promising. Suramin is a drug used in the treatment of trypanosomiasis and onchocerciasis and was shown recently to be a PTPase inhibitor. It was found to have anti-tumor activity against solid tumors in vitro and in vivo and is currently in clinical trials. Given the marked success of PTK inhibitor STI571 in the treatment of chronic myelogenous leukemia, it is tempting to speculate that PTPase inhibitors may emerge as novel therapeutics for malignant diseases in the near future.

PTPase inhibitor sodium stibogluconate inhibits the growth of human cancer cell lines in vitro in synergy with IFNα and IFNβ. It was demonstrated that the PTPase inhibitor could augment cell growth responses to hematopoietic growth factors, in part, by enhancing Jak/Stat tyrosine phosphorylation. This activity of the drug is consistent with its inhibition of SHP-1 or other PTPases that down-regulate Jak/Stat tyrosine phlosphorylation. Such a functional model of the PTPase inhibitor predicts that the drug may augment cellular responses to all cytokines signaling through the Jak/Stat pathways and is supported by our finding that the drug augments cell responses to IFNα in the hematopoietic cell line TF-1. It also suggested that augmenting signaling of cytokines (e.g., IFNγ) involved in the killing of the intracellular parasite may be an important pharmacological mechanism of the drug.

Importantly, potential novel clinical applications of the drug are suggested by this demonstrated effect of sodium stibogluconate in inhibiting SHP-1 and other PTPases and in augmenting cellular responses to hematopoietic growth factors and cytokines. Given the role of SHP-1 in the controlling threshold of antigen responses of T, B, and NK cells, the drug might be useful in augmenting immunity against cancers or infectious agents. The drug might also be effective in clinical situations where various hematopoietic growth factors are used. Among clinical applications of cytokines that may benefit from the drug are IFNα and IFNβ used in the treatment of various diseases, including malignancies. Currently, the effectiveness of IFNs in anti-cancer therapies is often limited by IFN-resistance of cancer cells. Drugs that augment IFN-responses of cancer cells may help to overcome such resistance, improve the efficacy of IFN therapies and expand the applications of cytokines in cancer treatment. In light of the pivotal role of PTPases in cell proliferation and viability, it is also possible that the PTPase inhibitor as a single agent may function as an anti-cancer drug by targeting PTPases essential for cancer cells.

To explore the potential of sodium stibogluconate as an anti-tumor drug, its effect on the growth of various human cancer cell lines in vitro was determined. The data demonstrate that the PTPase inhibitor, used alone or in combination with IFNα and IFNβ, was effective in inhibiting the in vitro growth of different human cell lines of lymphoma, multiple myeloma, leukemia, melanoma, prostate cancer, breast cancer, renal cancer and bladder cancer. Moreover, it is shown that this anti-cancer activity of the drug was related to the enhancement of tyrosine phosphorylation of specific cellular proteins and the induction of cell apoptosis. The effectiveness of the drug in overcoming IFN-resistance of cancer cells was indicated by the near complete killing by sodium stibogluconate alone or in combination with IFNα of cancer cell lines that showed only partial growth inhibition in response to the cytokine. The broad in vitro anti-cancer activity of the PTPase inhibitor indicates its potential as a novel anti-cancer drug as a single agent or in combination with IFNα/β. Moreover, the ability of the drug to augment Jak/Stat signaling via targeting Jak/Stat PTPase(s) suggests its effectiveness in other therapies of hematopoietic growth factors and cytokines that signal through the Jak/Stat pathway.

Drug Interaction Analysis. Median effect analysis, which provides the most general form of studying the interactions between drugs, was utilized to analyze the interaction between sodium stibogluconate and IFNα or IFNβ. Since details regarding the mode of IFN and sodium stibogluconate interaction are not fully understood, and whether or not they act in a mutually exclusive fashion, we chose the most general analysis available. Dose response curves were generated for each drug alone, and also the combinations. Median effect plots were generated, which determined m and $D_m$ values for IFN alone, sodium stibogluconate alone, and the combination. The combination index (CI) was determined and plotted vs. fraction affected (FA). Data were analyzed in both modes, mutually exclusive and mutually nonexclusive. The interaction between two mutually nonexclusive drugs is described by the Equation $CI=D_1/D_{x1}+D_2/D_{x2}+D_1D_2/D_{x1}D_{x2}$ where $D_{x1}$ and $D_{x2}$ are the doses of drug 1 and drug 2 that are required to inhibit growth x %. $D_1$ and $D_2$ in combination also inhibit growth x % (i.e. drug 1 and drug 2 are isoeffective). When CI<1, drugs are synergistic, when CI=1, drugs are additive, and when CI>1, drugs are antagonistic.

Detection of apoptotic cells by Annexin V/propidium iodide assay. Annexin V staining of exposed membrane phospholipid phosphatidylserine (PS) was done using the Annexin V assay kit (Pharmingen, San Diego, Calif.). Briefly, U266 or WM9 cells were cultured in the 10% FCS RPMI 1640 medium in the absence or presence of sodium stibogluconate, IFNα, or both for 3 days. Cells were then washed in PBS twice and stained in binding buffer (10 mM Hepes, pH 7.4; 140 mM NaCl; 2.5 mM CaCl2) containing Annexin V-FITC and propidium iodide for 15 min. The reaction was stopped by adding 10 volumes of binding buffer and analyzed by FACS (Becton Dickinson Facsvantage) or fluorescent microscopy.

Induction of Stat1 tyrosine phosphorylation by IFNα and/or sodium stibogluconate. For induction of Stat1 tyrosine phosphorylation by IFNα in the absence or presence of sodium stibogluconate, cells grown in 10% FCS RPMI 1640 medium at 37° C. were stimulated with IFNα (50 u/ml) for various time points and treated with or without sodium stibogluconate for 5 minutes prior to termination by lysing the cells in cold lysis buffer (1% NP-40; 50 mM Tris, pH 7.4; 100 mM NaCl; 1 mM EDTA, 10% glycerol, 10 mM sodium molybdic acid and 4 mM AEBSF).

Cell lysate preparation, SDS-PAGE, and Western blotting. Cell lysates were prepared by lysing cells in cold lysis buffer for 30 min and cleared by centrifuging at 14,000 rpm at 4° C. for 15 min. For SDS-PAGE, cell lysates were mixed with equal volume of 2×SDS-PAGE sample buffer, heated at 90° C. for 5 min and separated in 10% SDS-PAGE gels. Cellular proteins in SDS-PAGE gels were transferred to nitrocellulose membrane (Schleicher & Schuell), blocked in 5% milk, probed with antibodies and detected by using an enhanced chemiluminescence kit (ECL, Amersham).

Figure 18:
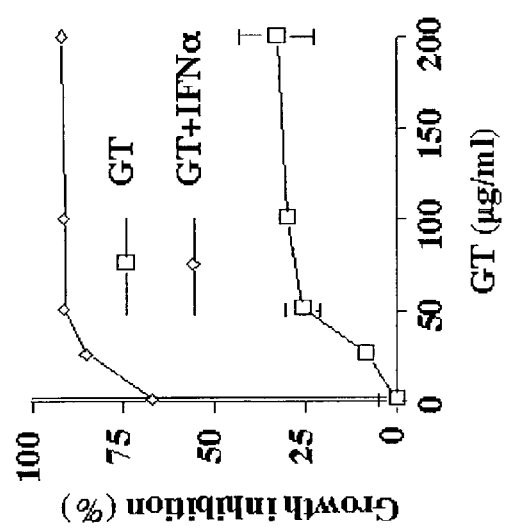
FIG. 18. Glucatime inhibits the growth of human cancer cell lines in culture and augments IFNα-induced growth inhibition. Growth of human cancer cell lines cultured in the absence or presence of glucatime and/or IFNα (500 U/ml) for 6 days were determined by MTT assays. Similar results were demonstrated in various cell lives including lung cancer (A549), lymphoma (DR), ovarian cancer (HEY), breast cancer (MDA231, or MDA), neuroblastoma (SK—N—SH, or SK) and melanoma (WM9).

Sodium stibogluconate inhibits the in vitro growth of human cell lines of hematopoietic malignancies and augments IFNα-induced cell growth inhibition. sodium stibogluconate markedly augmented IFNα-induced growth inhibition of the IFNα-resistant lymphoma cell line DR. DR and DS cell lines were derived from the parental human lymphoma cell line Daudi and were resistant or sensitive to IFNα, respectively. Consistent with their sensitivity to IFNα, DS cells cultured in the presence of IFNα (1,000 u/ml) were almost completely eliminated by day 3. In contrast, IFNα treatment resulted in only 19% growth inhibition of the DR cells. Importantly, this IFNα-induced DR cell growth inhibition was increased to 4669% in the presence of various amounts of sodium stibogluconate. Augmentation of IFNα-induced growth inhibition by sodium stibogluconate was also observed in prolonged culture of DR cells for 6 days (FIG. 18D), in which the 39% of IFNα-induced growth inhibition was increased to 80% and 92% in the presence of sodium stibogluconate at 12.5 µg/ml and 25 µg/ml respectively. Interestingly, the PTPase inhibitor by itself showed a marked activity against DR cells at higher dosages: it almost completely eliminated proliferation of DR cells (95-99%) in the day 6 culture at 50 µg/ml and 100 µg/ml as a single agent. sodium stibogluconate by itself showed a modest activity against the DS cells.

This initial observation of marked growth inhibition of DR cells by sodium stibogluconate alone or in combination with IFNα prompted the determination its effect against other cell lines of human hematopoietic malignancies. U266 is cell line of human multiple myeloma, a disease currently treated with IFNα. Again, augmentation of IFNα-induced cell growth inhibition of U266 cells was detected with a substantial growth inhibition activity of the drug by itself. Various degrees of augmentation of IFNα growth inhibition activity by sodium stibogluconate were also observed in other cell lines of T-lymphoma (H9) and T-ALL (Peer) (See Table 1).

Sodium stibogluconate inhibits the in vitro growth of human cell lines of non-hematopoietic malignancies and augments IFNα-induced growth inhibition. The effect of sodium stibogluconate in augmenting IFNα-induced growth inhibition and in causing growth inhibition by itself in cell lines of human hematopoietic malignancies suggested potential activity of the drug against nonhematopoietic cancer cells as the drug has inhibitory activity against PTPases (e.g., PTP1B and SHP-2) that express in various non-hematopoictic tissues.

Figure 19:
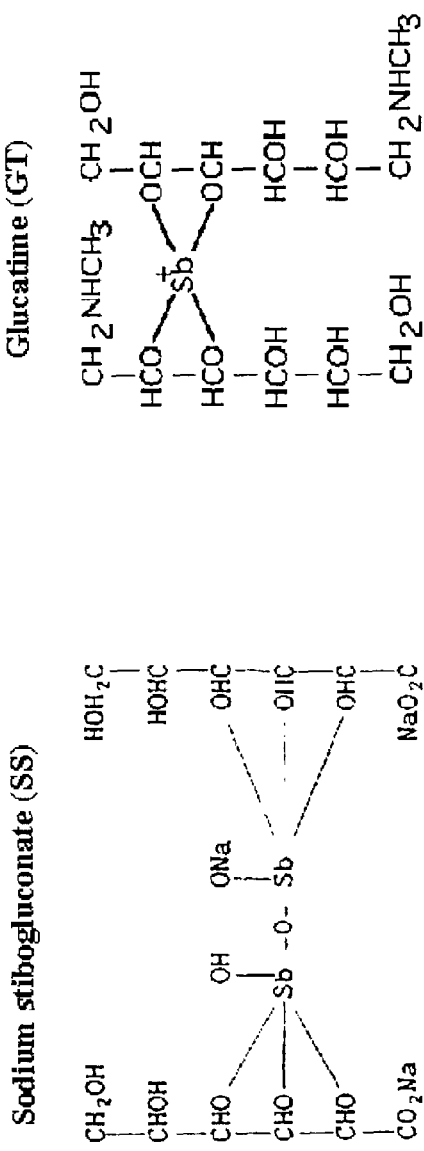
FIG. 19 illustrates the differential sensitivities of PTPPase to sodium stibogluconate in relationship to % inhibition in vitro of SHP-1, MKP1, and PRL-1.

Several solid tumor cell lines were found to be sensitive to the PTPase inhibitor alone or in combination with IFNα. IFNα-induced growth inhibition of WM9 (melanoma), DU145 (prostate cancer), and MDA231 (breast cancer) was augmented by sodium stibogluconate (FIGS. 19A, B, and C). Like the DR lymphoma cell line, these tumor cell lines were sensitive to the PTPase inhibitor as a single agent, which at 50 µg/ml and 100 µg/ml dosages killed all cells in day 6 culture. The Wilms tumor cell line WiT49-N1 was also sensitive to sodium stibogluconate although its growth inhibition activity was not enhanced by IFNα (FIG. 19D).

Further studies of the drug in additional cell lines demonstrated that sensitivity to sodium stibogluconate was not tumor type-specific but unique to individual cell lines. In contrast to the sensitive WM9 melanoma cell line, the WM35 melanoma cell line was minimally affected by sodium stibogluconate (Table 1). Unlike the DU145 prostate cancer cell line, the C42 prostate cancer cell line was highly resistant to the inhibitor (Table 1). Growth responses of several other human tumor cell lines to IFNα and/or sodium stibogluconate were also determined (Table 1).

Sodium stibogluconate augments IFNα- and IFNβ-induced growth inhibition of WM9 cells in a synergistic manner. To further investigate whether augmentation of IFNα-induced cell growth inhibition by sodium stibogluconate was unique to this drug combination, the effect of the drug on IFNα- or IFNβ-induced growth inhibition of the WM9 cell line of human melanoma, which is currently treated by the cytokines, was compared.

Figure 10:
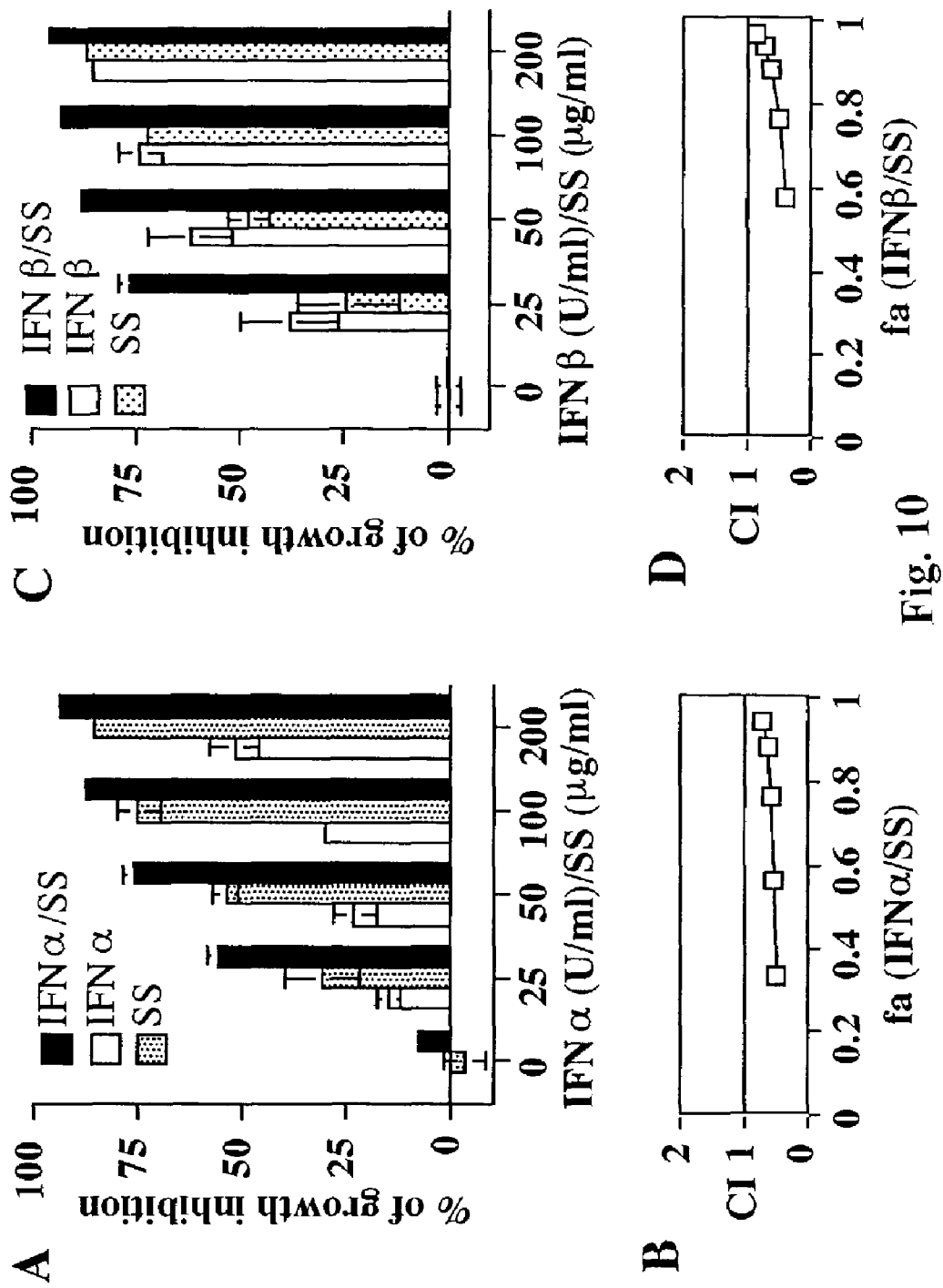
FIG. 10 illustrates sodium stibogluconate augments both IFNα- and IFNβ-induced growth inhibition of WM9 cells. Percentage of growth inhibition of WM9 cells in the absence or presence of various amounts of sodium stibogluconate, IFNα and IFNβ in day 6 cultures as measured by MTT assays. The data illustrates that sodium seems to interact with IFNα and IFNβ in a synergistic manner in growth inhibition of WM9 cells. Data from MTT antiproliferative assays was expressed as percent control growth (PCG) of treated cells, compared to untreated cells (100%). Median effect analysis (inset graphs), similar to isobol analysis, defined drug interaction in the IFNα+sodium stibogluconate and the IFNβ+ sodium stibogluconate combinations as synergistic at all doses tested, characterized by a combination index (CI) of less than 1. Additivity is indicated by CI=1, and antagonism occurs when CI>1. Fraction affected (fa)=(100−PCG)/100.

The growth of WM9 cells was suppressed by IFNα (FIG. 10A) and, more potently, by IFNβ (FIG. 10B). In the presence of sodium stibogluconate, IFNα- and IFNα-induced growth inhibition was greatly enhanced (FIG. 10). This augmentation of IFNα/β-induced growth inhibition by sodium stibogluconate was most dramatic at lower dosage levels of sodium stibogluconate (12.5-50 µg/ml) and the IFNs (12.5-50 u/ml) but was also detectable in the higher dosage range (FIG. 10). Thus, sodium stibogluconate was effective in augmenting the growth inhibition activity of IFNα and IFNβ against WM9 cells.

To determine the nature of the drug interaction in the IFNα/sodium stibogluconate and IFNβ/sodium stibogluconate combinations, data in FIG. 20 were subject to median effect analysis to derive combination index (CI) values that define drug interaction as synergy (CI<1), additivity (CI=1) or antagonism (CI>1). The results, calculated in both modes of mutually exclusive and nonexclusive, demonstrate that the drug interaction in the combinations of IFNα/sodium stibogluconate (FIG. 10B) and IFNβ/sodium stibogluconate (FIG. 10D) are synergistic at all doses tested, characterized by a CI value less than 1. Since the growth inhibition of DR, DU145, and MDA231 cells achieved by the combination of sodium stibogluconate and IFNα was similar to that of the WM9 cells (FIGS. 18 and 19), the results also suggested a synergistic interaction for the two agents in those cell lines.

The marked growth inhibition of tumor cell lines by sodium stibogluconate alone and/or in combination with IFNα indicated induction of cell death by the PTPase inhibitor. Therefore, the numbers of apoptotic cells of U266 and WM9 cell lines grown in the presence of sodium stibogluconate, IFNα, or both was determined.

Increased apoptosis of U266 cells was detected in the presence of sodium stibogluconate alone and, more dramatically, of the inhibitor and IFNα both. In the presence of sodium stibogluconate (100 µg/ml), the percentage of apoptotic cells was increased to 17% from 8% (control). IFNα (1000 u/ml) induced 16% apoptosis. When both sodium stibogluconate and IFNα were present, the number of apoptotic cells increased to 42%. Evaluated by fluorescent microscopy, WM9 cells in the presence of sodium stibogluconate, IFNα, or both were increased to 11%, 15%, or 31% respectively from 5% (control). Thus, growth inhibition of these tumor cell lines by sodium stibogluconate and IFNα was mediated at least in part by inducing apoptosis.

Figure 9:
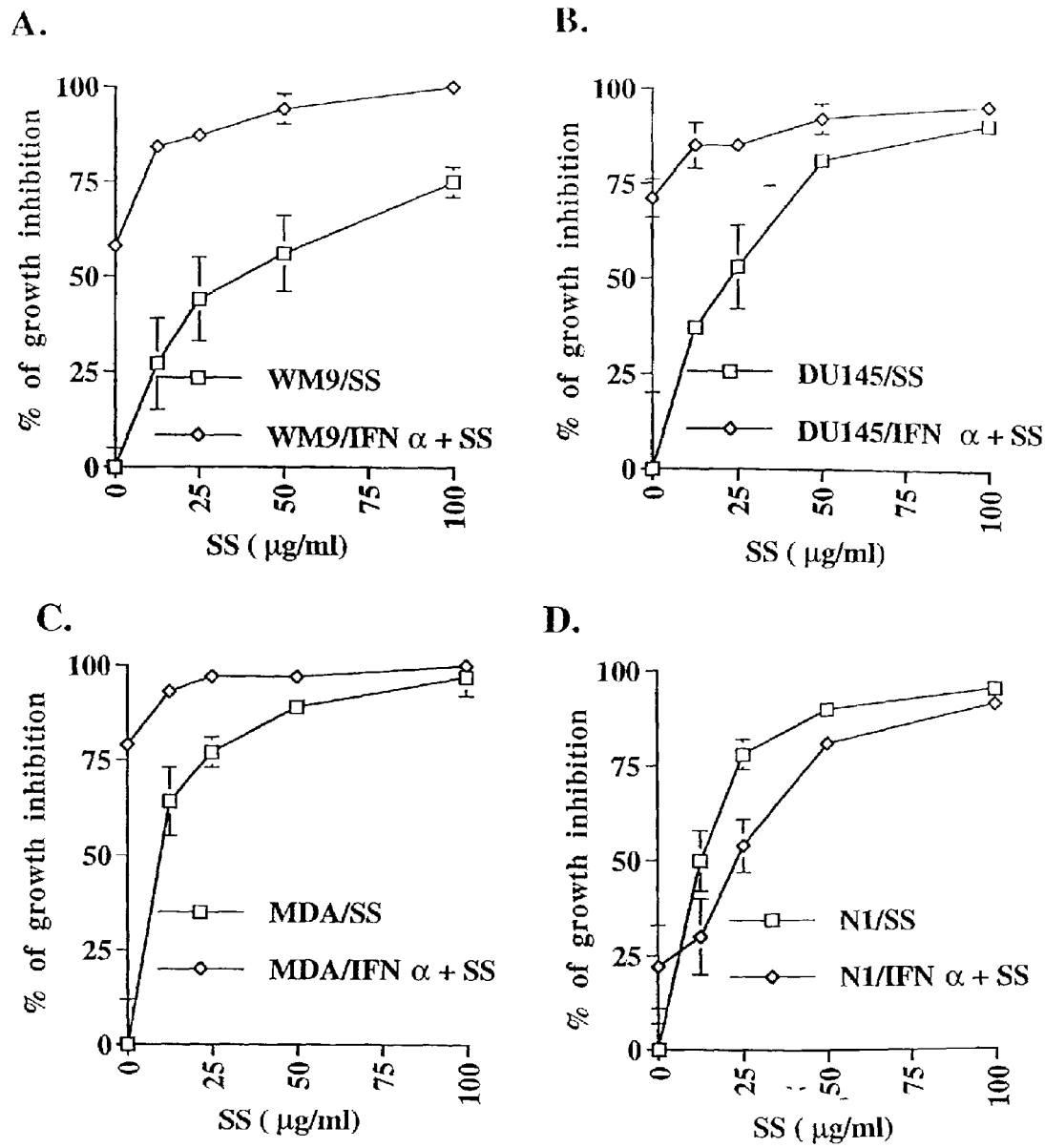
FIG. 9 illustrates growth inhibition of human cell lines of non-hematopoietic malignancies by sodium stibogluconate and/or IFNα. Percentage of growth inhibition of WM9 (A), DU145 (B), MDA231 (C) and WiT49-N1 (D) in the absence or presence of various amounts of sodium stibogluconate and/or IFNα (1,000 u/ml) in day 6 cultures as measured by MTT assays.

Augmentation of IFNα-induced cell growth inhibition by sodium stibogluconate correlates with enhanced Stat1 tyrosine phosphorylation. In the absence of sodium stibogluconate, Stat1 tyrosine phosphorylation in DR cells was induced by IFNα within 30 min and decreased by 5 hours post-stimulation. In the presence of sodium stibogluconate (10 µg/ml), Stat1 tyrosine phosphorylation at 30 min post-stimulation was approximately two folds greater than control and remained elevated for 5 hours. Enhanced Stat1 tyrosine phosphorylation at 5 hours post-stimulation by IFNα was also detected in WM9 and DU145 cell lines cultured in the presence of sodium stibogluconate. In contrast, sodium stibogluconate failed to enhance IFNα-induced Stat1 tyrosine phosphorylation in WM35 and WiT49-N1 cell lines in which no antiproliferative synergy between IFNα and sodium stibogluconate was detected (Table 1 and FIG. 9D). In the absence of IFNα, sodium stibogluconate failed to induced Stat1 tyrosine phosphorylation by itself in DR cells. IFNα-induced Stat1 tyrosine phosphorylation in WiT49-N1 cells was not increased in the presence of sodium stibogluconate.

Resistance of cancer cells to IFNα and IFNβ is a major problem that limits the clinical application of these cytokines in anti-cancer therapies. Although the mechanism of IFN-resistance of cancer cells is not fully understood, reduced IFN signaling is often detected in cancer cells and believed to be an important factor. Therapeutic reagents that augment IFN signaling may help to overcome such resistance in cancer cells but have not been reported yet.

Sodium stibogluconate, a drug used for leishmaniasis and a PTPase inhibitor, augments IFN signaling and can overcome IFN-resistance in various human cancer cell lines. Augmentation of IFNα signaling by the drug was clearly demonstrated by its enhancement of IFNα-induced Stat1 phosphorylation. This activity was detectable at its therapeutic concentration (10-20 µg/ml) that is clinically well tolerated. Moreover, the activity of the drug in augmenting of IFNα signaling was effective in overcoming IFN-resistance as it was accompanied by augmentation of IFNα-induced growth inhibition of various human cancer cell lines.

The drug at 25-100 µg/ml was extremely effective at overcoming IFN-resistance of cell lines that were only partially inhibited by IFNα as a single agent. This was well-illustrated by the complete elimination of WM-9 melanoma cells by the drug and IFNα in combination while the two agents individually achieved only 75% and 58% growth inhibition, respectively. Similarly, the drug at 25 µg/ml combined with IFNα achieved near complete elimination of MDA231 breast cancer cells compared to 65% and 79% growth inhibition by the two agents individually. This in vitro anti-cancer activity of the drug alone or in combination with IFNα was shown to involve induction of apoptosis in WM9 cell and U266 cells. Although the standard dosage for leishmania treatment is 1020 mg/kg/day resulting in 10 µg/ml or more serum levels, higher drug dosages may be clinically achievable and tolerated. Doses as high as 850 mg/kg/day have been used in leishmania treatment.

The finding that sodium stibogluconate also augmented IFNβ-induced growth inhibition suggests that the drug may improve the efficacy of IFNβ therapies in the treatment of cancer as well as several other diseases (e.g., hepatitis B and multiple sclerosis) that are currently treated with the cytokine. Moreover, it provided additional evidence that among the targets of the PTPase inhibitor are Jak/Stat PTPases which down regulate cytokine signaling by dephosphorylating Jak/Stat proteins, a hypothesis based on the previous finding of drug augmentation of cell responses to IL-3 and GM-CSF that signal through the Jak/Stat pathway like the IFNs. PTPase SHP-1 and CD45 are known to down-regulate Jak/Stat tyrosine phosphorylation in hematopoietic cells. As the expression of SHP-1 and CD45 was not detectable in WM9 cells in which IFNα-induced Stat1 phosphorylation was augmented by the drug, the results indicate the existence of other Stat1-regulatory PTPase(s) as the drug target in these cells. But the data does not exclude the involvement of SHP-1 or CD45 as drug targets in hematopoietic cells. This mechanism of the drug targeting Jak/Stat PTPase(s) predicts that the PTPase inhibitor will have a similar activity in augmenting the signaling of other cytokines signaling through the Jak/Stat pathway. Many cytokines signaling through Jak/Stat pathway (e.g., IL-2, IL-4, and IL-12) have been used in anti-cancer therapies, which may be improved in combination with the PTPase inhibitor.

The interaction of sodium stibogluconate with IFNα and IFNβ in growth inhibition of WM9 melanoma cells was clearly synergistic. Such a synergy between the drug and IFNs is consistent with the augmentation of IFN-induced Stat1 phosphorylation by the PTPase inhibitor. Although several other drugs have been shown to synergize with IFNs, sodium stibogluconate is one that works through targeting molecules in the IFN signaling pathway.

The results also provided the first evidence that the drug alone had marked growth inhibitory activity against human cancer cell lines in vitro. This activity was most dramatic at higher dosages (25-100 µg/ml) with a substantial activity detectable at therapeutic concentration. For instance, sodium stibogluconate at 100 µg/ml achieved complete or near complete killing of cells in day 6 culture of the DR, DU145, MDA231, and WiT49-N1 cell lines. Induction of cell apoptosis may play a role in the killing of the cancer cells as indicated by the increased apoptosis of WM9 and U266 cells in the presence of sodium stibogluconate at 100 µg/ml. Unlike the synergy of the drug at therapeutic concentration with IFNs that was mediated via targeting Jak/Stat PTPases to augment IFN-induced Jak/Stat phosphorylation and—signaling, this activity of drug is likely mediated by other PTPases independent of the Jak/Stat pathway as indicated by the failure of the drug alone to induce Stat1 phosphorylation at 10 µg/ml or at higher concentration (our unpublished data). More detailed analysis of sodium stibogluconate-sensitive cells to identify cellular proteins whose tyrosine phosphorylation are affected by the drug alone in drug-sensitive cells may help to elucidate the underlying mechanism.

The sensitivity of certain human cancer cell lines to the drug by itself suggests potential effectiveness of sodium stibogluconate as a single agent in cancer treatment. In this regard, the finding that drug sensitivity is unique to individual cancer cell lines instead of tumor type-specific underscores the importance of identification of markers of drug-sensitivity and—resistance in cancer cells. It is likely that drug-resistance may be due to the absence of target PTPases or PTPase substrates in drug-resistant cells which have adapted to grow without these molecules. In this regard, it is interesting that differential expression of PTPases in the sensitive WM9 and resistant WM35 melanoma cell lines was detected by gene expression profiling. Additional studies are clearly needed in this area and could have important clinical significance.

Sodium stibogluconate synergizes with IFNα to eradicate human melanoma WM9 tumors and markedly suppress human prostate carcinoma DV145 tumors in nude mice. Preliminary studies described above clearly demonstrate a marked activity of PTPase inhibitor sodium stibogluconate against various cancer cell lines in vitro. Next, the critical issue of whether the drug has anti-cancer activity in vivo at a dosage that is clinically achievable and tolerated was addressed. For this, the efficacy of sodium stibogluconate, as a single agent or in combination with IFNα, against human melanoma WM9 and human prostate carcinoma DLJ145 xenografts in nude mice was determined.

WM9 and DU145 cell lines were used for the study based on the following considerations: 1) the two cell lines were found in our preliminary study to be sensitive to sodium stibogluconate as a single agent or in combination with IFNα (FIG. 19A-B); 2) both cell lines are known to be tumorigenic in nude mice; 3) the cell lines represent human malignancies that are major health threats with no effective treatment; 4) IFNα is used in the treatment of melanoma and prostate cancer with modest outcome, which may be significantly improved by combinational therapy with sodium stibogluconate that synergize with the cytokine.

Nude mice bearing WM9 or DU145 xenografts were treated with IFNα (500,000 U, s.c., daily), sodium stibogluconate (12 mg Sb, s.c., daily), or both. The amount of IFNα used for the treatment is comparable to the dosages used in similar studies. The dosage of sodium stibogluconate corresponds to approximately 440 mg Sb/kg body weight (average mouse body weight 27 g), substantially higher than the standard therapeutic dose of 20 mg Sb/kg and the high dose (143 mg Sb/kg) that was clinically used by accident without serious toxicity. The dose of sodium stibogluconate used in the study was chosen based on the previous observation in a pilot study that mice could tolerate daily dose of 20 mg Sb (approximately 700-800 mg Sb/kg). The observation that the effect of sodium stibogluconate in inhibiting the growth of the cancer cell lines in vitro was dose-dependent with complete or near complete killing of the cancer cells at 100 pg Sb/ml (or 100 ug Sb/kg) was also considered. In light of the relatively rapid rate of clearance of the drug in vivo, 440 mg Sb/kg dosage was used to ensure the detection of the effectiveness of the drug for this initial study.

For each of the cell lines, each of 16 mice received subcutaneous injection at the chest area of $3 \times 10^6$ cells/site (WM9) or $2 \times 10^6$ cells/site (DU145), two sites/mouse, on day 0. Mice were separated into four groups of four to receive treatment, injected into the thigh area and starting on day 2. Tumor size was measured with a caliper to determine the two perpendicular diameters of each tumor. Tumor volume was calculated using the method of the NCI (length×width$^2$ in millimeters/2=volume in cubic millimeters).

Sodium stibogluconate as a single agent has a marked anti-tumor activity in vivo and synergizes with IFNα to eradicate xenografts of human melanoma WM9 in nude mice. To test the anti-tumor effects of sodium stibogluconate and its synergy with IFNα in vivo, the effect of sodium stibogluconate, IFNα, and their combination against xenografts of human WM9 melanoma in nude mice was determined. WM9 cells were inoculated into nude mice which were then subjected to no treatment (control) or treatment for 23 days with single agents or their combination starting on day 2 following inoculation. Tumor volume of WM9 xenografts in the mice was determined during the treatment course as indicators of efficacy of the treatment.

WM9 cells in nude mice formed tumors that showed continuous growth in a time dependent manner in the absence of any treatment. Treatment with alone significantly suppressed WM9 tumor growth in the mice and resulted in an average tumor volume approximately 40% of the control group by the end of the treatment. Interestingly, treatment with sodium stibogluconate alone caused a dramatic tumor growth suppression (tumor volume about 20% of the controls on day 25), superior to that of IFNα treatment under the experimental conditions. Most strikingly, treatment with the combination of sodium stibogluconate and IFN∀ led to a gradual shrinkage of WIND tumors which were visually invisible by day 18. This absence of visible tumor in this group of mice continued until the end of the treatment course by day 25. Two mice of this group were observed for additional 8 weeks without treatment. No visually visible tumor was detected in these mice at the inoculation sites during this additional observation period. Thus the combinational treatment eradicated the pre-formed WM9 tumors in the nude mice.

Sodium stibogluconate markedly suppresses the growth of xenografts of human prostate carcinoma DU145 in nude mice. As shown in FIG. 24B, inoculation of DU145 cells in nude mice resulted in formation of tumors that was not significantly suppressed by IFNα monotherapy during the most part of the treatment duration, consistent with a previous study. A modest anti-tumor activity of the cytokine was detected by the end of the treatment course with the average tumor volume approximately 70% of the control on day 25. In contrast, sodium stibogluconate as a single agent markedly suppressed DU145 tumor growth and resulted in an average tumor volume of approximately 30% of the control by day 25. This anti-tumor activity of sodium stibogluconate was further augmented when the drug was used in combination with IFNα (average tumor volume 18% of control on day 25). These results together demonstrated that sodium stibogluconate has a marked anti-tumor activity against DU145 xenografts in nude mice and that the drug interacts with IFNα to achieve a striking growth inhibition of DU145 xenografts in nude mice.

The effective dosage of sodium stibogluconate against WM9 and DU145 xenografts is well tolerated in nude mice. As discussed above, the dosage of sodium stibogluconate used for the treatment of nude mice was 12 mg Sb/mouse, s.c., daily (or approximately 440 mg/kg body weight). Thus dosage is much higher than the standard dose for Leishmaniasis (20 mg Sb/kg, daily). As an initial step to assess the toxicity of such a high dosage of sodium stibogluconate in nude mice, its effect on the viability and body weights of WM9 xenografts nude mice during the 25 day period of the study was determined.

All of the 16 mice inoculated with WM9 cells survived till the end of the study (day 25) regardless their treatment (control, sodium stibogluconate, IFNα, or both, 4 mice/group). The average body weight of the mice subjected to combinational treatment with sodium stibogluconate and IFNα showed no significant difference from that of the control group mice or those of the sodium stibogluconate- or IFNα-treatment group (data not shown) during the study period. In addition, no obvious difference was noticed among the 4 groups of mice in their general appearance, feeding, or activity. Dissection of two mice from each group of the mice revealed no apparent abnormality of the internal organs. Two mice of the combinational treatment group were observed for additional 8 weeks without treatment. They showed no visually obvious abnormality during the period, indicating that the treatment caused no serious longterm side effect.

In summary, these results demonstrate that sodium stibogluconate, as a single agent, showed a significant activity, higher than that of IFNα, against the two types of tumors in vivo. Moreover, sodium stibogluconate synergized with IFNα to eradicate the WM9 tumors in the nude mice with the combinational treatment for 16 days. It was also found that sodium stibogluconate synergized with IFNα to achieve striking growth inhibition of the DU-145 tumors superior to those of the two drugs used alone.

Additionally, the responses of the two tumor cell lines to sodium stibogluconate and/or IFNα in vivo correlated with their responses in vitro; the WM9 cell line was more sensitive to the combination treatment of sodium stibogluconate and IFNα in vivo than the DLT145 cell line, similar to our in vitro results. We also found that sodium stibogluconate at the dosage used in the study (12 mg Sb, daily of 440 mg Sb/kg daily) was well tolerated with no serious side effect.

The conclusions based on these results that: sodium stibogluconate has a marked and broad anti-tumor activity in vivo as a single agent at a dosage that may be clinically achievable and tolerated; the demonstrated synergy between sodium stibogluconate and cytokines, specifically IFNα in vivo indicates that combinational usage of sodium stibogluconate may significantly improve the current IFNα therapies in cancer treatment; since sodium stibogluconate targets PTPases and therefore functions via a mechanism distinct from those of current anticancer therapies, the drug may be useful as an alternative therapeutic for cancers non-responsive or resistant to conventional anti-cancer therapies; the correlation between in vitro and in vivo responses of cancer cell lines to sodium stibogluconate or sodium stibogluconate/IFNα indicates that other human cancer cell lines sensitive to these agents in vitro, as detected in preliminary studies, will be responsive to these agents in vivo as well; this further suggests that the human malignancies represented by the sensitive cell lines (e.g., human breast cancer cell line MDA231 and multiple myeloma cell line U266) may benefit from sodium stibogluconate/IFNα combinational therapies; since the nude mice study verified that the synergy between sodium stibogluconate and IFNα as detected in vitro also occurs in vivo, the in vitro synergy of sodium stibogluconate with other cytokines (e.g., IFNP) as detected in preliminary studies may similarly exist in vivo; therefore, sodium stibogluconate may be a useful adjuvant in IFNα therapy for viral or autoimmune diseases (e.g. hepatitis C and multiple sclerosis).

Importantly, it was demonstrated that sodium stibogluconate markedly enhances the anti-cancer activity of IFNα and has significant anti-cancer activity as a single agent against cell lines of various human malignancies in vitro and in vivo. The data showed that sodium stibogluconate, alone or in combination with IFNα, markedly suppresses the growth of human cancer cell lines in vitro. It was further demonstrated that combination treatment with sodium stibogluconate and IFNα for 16 days resulted in eradication of pre-formed tumors of advanced-stage human melanoma WM9 in nude mice with no apparent toxicity. The drug as a single agent also showed a marked anti-tumor activity superior to that of IFNα against WM9 xenografts. sodium stibogluconate alone or in combination with IFNα also showed striking activity against tumors of IFNα-refractory human prostate cancer DU145 in nude mice, suggesting a broad activity of the drug against different types of tumors in vivo. Given that not all cancer cells are sensitive to sodium stibogluconate, the finding that ketoconazole inhibits different PTPases in vitro and may therefore act against different cancer cells suggests its potential as an anti-cancer drug in sodium stibogluconate-resistant cases.

These results indicate these PTPase inhibitors as novel anti-cancer therapeutics warrant further investigation. As they are well-tolerated drugs already in clinical use, their novel mode of action and striking anti-cancer activity of sodium stibogluconate suggests their potential for rapid incorporation into current anti-cancer therapies. Although, not wishing to be bound by theory, the following hypotheses are proposed: a) the anti-cancer activity of sodium stibogluconate associates with a distinct sodium stibogluconate fraction more potent and less toxic than the parental drug, which is a mixture of molecules resulted from differential polymerization with poor activity and increased toxicity associated with degradation of the polymers; b) the mechanism of action of sodium stibogluconate to synergize with IFNα can be attributed to its effects on IFNα signaling molecules and ISGs (IFN-stimulated genes) via inactivation of PTPases through covalent modification of the enzymes; c) sodium stibogluconate, pentamidine and ketoconazole have differential anti-cancer activities via targeting different PTPases.

Like PTKs, PTPases show striking specificity in dephosphorylating unique protein substrates. This specificity is determined in part by the catalytic domain of individual PTPase, which recognizes its own set of substrates with particular structures that fit in the catalytic pocket of the enzyme. Such an interaction between a PTPase and its substrates has led to the development of trapping mutants of PTPases and the identification specific substrates. It also indicates the feasibility of developing inhibitors specific for individual PTPases through blocking such an interaction.

A cysteine residue conserved in the catalytic domain of all PTPases may play a critical role in dephosphorylation. This residue accepts the $PO_3$ moiety from phosphorylated amino acid in substrates and forms a phosphocysteine intermediate which is hydrolyzed to complete the dephosphorylation process. Substituting the cysteine residue in PTPases with a serine residue inactivates the enzymes. This cysteine residue is also the target of PTPase inhibitor pervanadate, which oxidizes the sulfhydryl group (—SH) of the residue to sulfonic acid (—$SO_3H$) thus blocking the formation of the phosphocysteine intermediate required for the dephosphorylation process.

Anti-cancer activity of sodium stibogluconate in synergy with IFNs: an inhibitor of PRL phosphatases. PRL family phosphatases have been proposed as targets for developing anti-cancer therapeutics as their over expression caused cell transformation in culture, promoted tumor growth in mice (PRL-1 or PRL-2) and associated with metastasis of colorectal cancer (PRL-3). To assess whether PRL phosphatases were potential sodium stibogluconate targets, the effect of sodium stibogluconate on the phosphatase activity of PRLs was assessed in vitro.

Recombinant GST fusion proteins of human PRL-1, 2 and 3 phosphatases were purified with glutathione beads from DH5α bacteria transformed by pGEX vectors containing cDNA fragments encoding the human PRLs which were generated by RT-PCR from H9 cells and confirmed by sequence analysis. Activities of the purified recombinant PRL proteins in dephosphorylating DiFMUP in the absence or presence of various inhibitors were measured following established procedure. Phosphatase activity of PRL-3 bound to glutathione beads and preincubated with sodium stibogluconate then subjecting no washing (Wash−) or a washing process (Wash+), which was shown to remove the inhibition of SHP-1 by reversible inhibitor suramin.

Relative expression levels of PRLs in peripheral blood mononuclear cells from two healthy volunteers and in cancer cells lines were generated by RT-PCR with specific primer pairs for individual PRLs or for GAPDH. RT-PCR products were separated in an agarose gel and visualized by ethidium bromide staining with their identities confirmed by restriction endonuclease mapping. The sequence of primer pairs are:

```
huPRL-3/5', TAGGATCCCGGGAGGCGCCATGGCTCGGATGA;
huPRL-3/3', GAGTCGACCATAACGCAGCACCGGGTCTTGTG;
huPRL-2/5', TAGGATCCCCATAATGAACCGTCCAGCCCCTGT;
huPRL-2/3', GAGTCGACCTGAACACAGCAATGCCCATTGGT;
huPRL-1/5', TAGGATCCCCAACATGGCTCGAATGAACCGCCC;
huPRL-1/3', GAGTCGACTTGAATGCAACAGTTGTTTCTATG.
```

Figure 11:
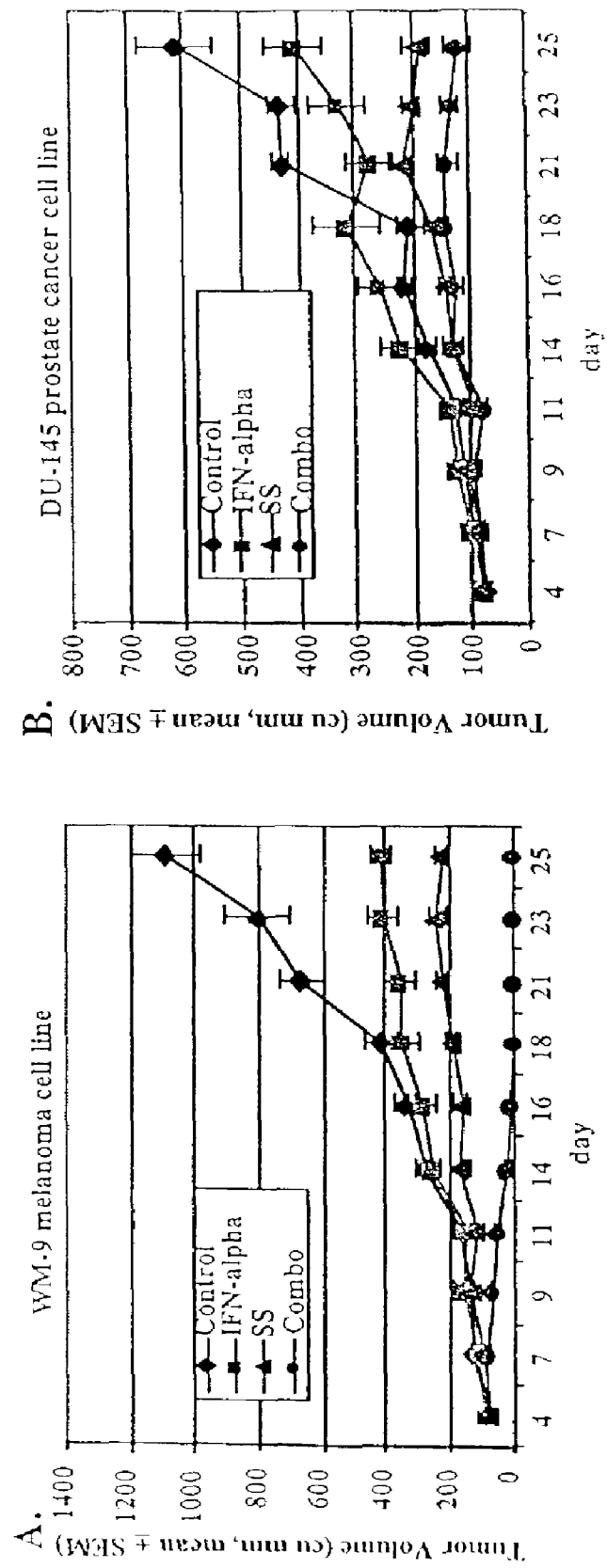
FIG. 11 illustrates that sodium stibogluconate appears to synergize with IFNα against WM9 human melanoma tumors in nude mice. IFNα or both on the growth of xenografts of human melanoma cell line WM9 and human prostate carcinoma cell line DU-145 in athymic nude mice. Nude mice of 4 weeks old were inoculated subcutaneously (s.c.) with WM9 human melanoma cells ($3 \times 10^6$ cells/site) (A) or DU-145 human prostate cancer cells ($2 \times 10^6$ cells/site) (B) on day 0. Starting on day 2, the mice were subjected to no treatment (Control) or treatment with IFNα (500,000 U, s.c., daily), sodium stibogluconate (12 mg, s.c., daily) or both (Combo). Tumor volume in the nude mice (4 mice/group, 2 tumors/mouse) was measured on the days as indicated. Tumor volume was calculated by the equation: (length×width$^2$)/2 to compare tumor growth rates. All mice survived by the end of the experiment.
Figure 11A:
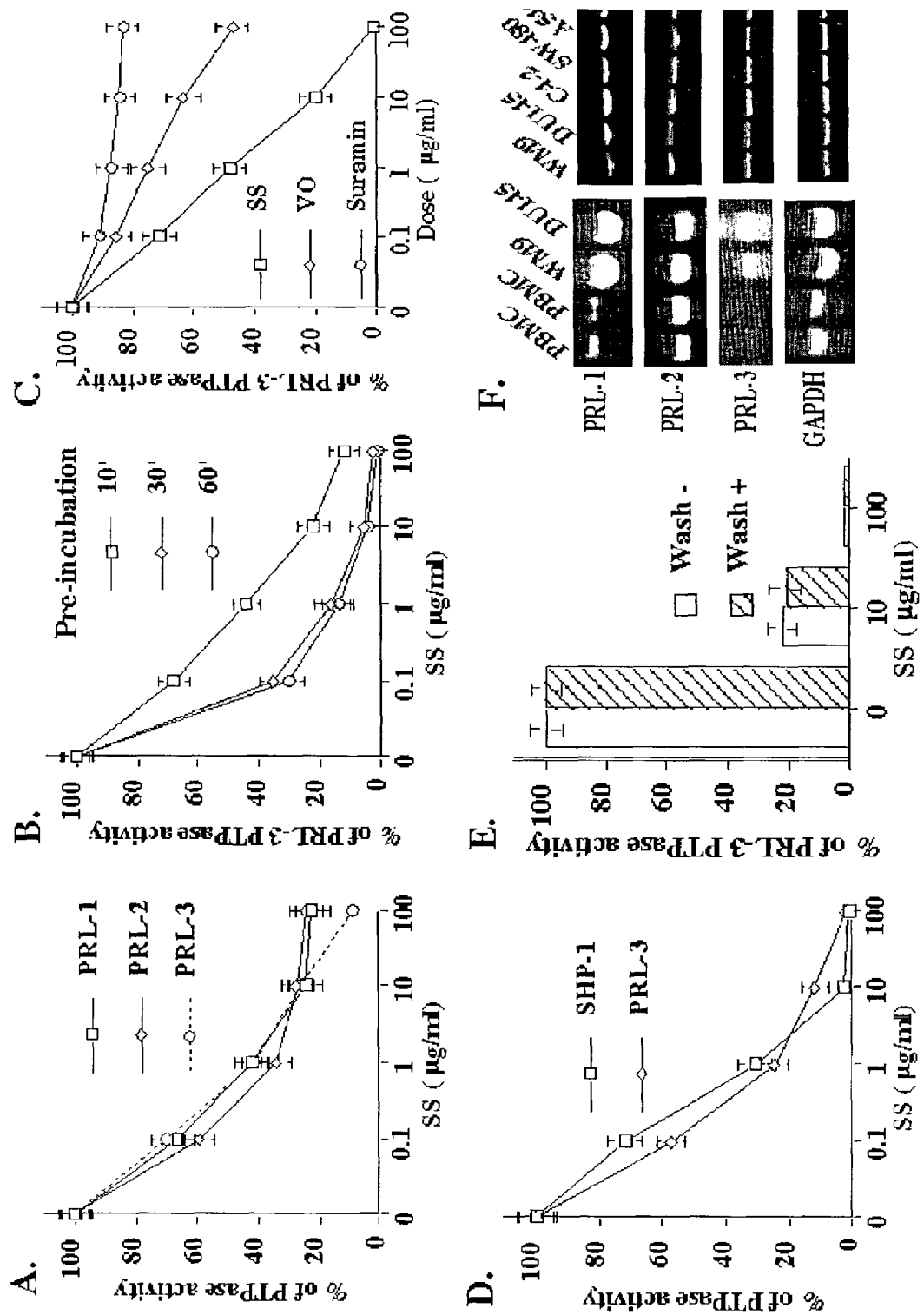
FIG. 11A illustrates that sodium stibogluconate in vitro inhibits oncogenic PRL phosphatases that are commonly expressed in human cancer cell lines. A. Relative activities of recombinant PRL phosphatases in dephosphorylating a synthetic phosphotyrosine peptide in vitro in the absence or presence of various amounts of sodium stibogluconate, which was pre-incubated with the phosphatases for 10 minutes prior to initiation of PTPase reaction. B. Effects of differential pre-incubation times of sodium stibogluconate with recombinant PRL-3 on PRL-3 activity in dephosphorylating the peptide substrate. C. Relative activities of recombinant PRL-3 in dephosphorylating DiFMUP substrate in the absence or presence of various amounts of sodium stibogluconate, sodium orthovanandate (VO) or suramin. D. Relative activities of recombinant SHP-1 and PRL-3 in dephosphorylating DiFMUP in the absence or presence of sodium stibogluconate. E. Relative activities of PRL-3 bound to glutathione beads and preincubated with sodium stibogluconate then subjected no washing (Wash−) or a washing process (Wash+), which was shown to remove the inhibition of SHP-1 by reversible inhibitor suramine. F. Expression levels of PRLs in human cancer cell lines and in PBMC of two healthy volunteers.

Sodium stibogluconate is a potent inhibitor of recombinant PRL-1, PRL-2 and PRL-3 in vitro. To assess whether sodium stibogluconate is an inhibitor of oncogenic PRL phosphatases, its effects on the PTPase activity of recombinant PRLs were evaluated by in vitro PTPase assays. PTPase activity of recombinant PRL-1, PRL-2 and PRL-3 in dephosphorylating a synthetic phosphotyrosine peptide substrate was decreased in the presence of sodium stibogluconate in a dose-dependent manner with sodium stibogluconate at 100 mg/ml resulted in 80-90% of inhibition of the PTPases (FIG. 11A). These effects of sodium stibogluconate were detected under the condition that the PRLs were pre-incubated with the drug for 10 minutes prior to the initiation of PTPase assays by addition of substrate to the reactions. Since the three phosphatases were inhibited in a similar manner by sodium stibogluconate, PRL-3 was selected to further investigate the effect of prolonged pre-incubation with sodium stibogluconate on its phosphatase activity. Pre-incubation of PRL-3 with sodium stibogluconate for 30 or 60 minutes resulted more dramatic inhibition with nearly complete inactivation of PRL-3 occurred at sodium stibogluconate concentration of 10 mg/ml (FIG. 11B). Inhibition of PRL-3 by sodium stibogluconate was also detected using an alternative substrate (DiFMUP) while the known phosphatase inhibitors sodium orthovanadate and suramin were less effective than sodium stibogluconate under comparable conditions (FIG. 11C). The percentages of inhibition of PRL-3 in the presence of various doses of sodium stibogluconate were similar to those of sodium stibogluconate-induced SHP-1 inactivation (FIG. 11D). sodium stibogluconate-induced PRL-3 inactivation was not relieved by a washing process (FIG. 11E) that was effective in removing the inhibition of SHP-1 by reversible inhibitor suramin.

These results demonstrated that sodium stibogluconate was a potent and irreversible inhibitor of recombinant PRL phosphatases in vitro.

PRLs are expressed in cell lines of various human malignancies.

As an inhibitor of oncogenic PRL phosphatases, sodium stibogluconate could be expected to be most effective against human malignancies in which these sodium stibogluconate-targeted molecules are present. To address this issue, we determined the expression of PRLs in cell lines of various malignancies by RT-PCR analysis which revealed the presence of the transcripts of the PRLs in the cell lines with PRL-1 and PRL-3 expression at levels higher than those in the PBMC of two healthy volunteers (FIG. 11F). These results suggests that expression of PRLs may be common in human malignancies which could benefit from sodium stibogluconate therapy.

Melanomas are currently treated with IFNα with moderate response rates (1520%) while the cytokine is effective in only 5% of prostate cancer patients. sodium stibogluconate may significantly improve the efficacy of IFN therapy for these malignancies. Moreover, the demonstrated in vitro effects of sodium stibogluconate in augmenting IFNα-induced growth inhibition of cell lines of other human malignances suggest the potential of sodium stibogluconate/IFN combination therapy for different types of cancer. Such combination therapy may be particularly useful in cancer that are nonresponsive to conventional chemotherapy or radiation therapy since sodium stibogluconate and IFNs modulate targets in cancer cells different from those of conventional therapies.

One of the most significant findings concerns the inhibitory activity of sodium stibogluconate against PRL phosphatases. Their inactivation is likely responsible at least in part for the anti-cancer effect of sodium stibogluconate as a single agent functioning independently of IFN signaling. The notion that PRLs are among sodium stibogluconate targets is also consistent with the known toxicity profile of the drug (modest cardiac toxicity and leukopenia) that correlates with the major physiologic expression sites of PRL-3 (cardiac muscle) and PRL-2 (peripheral blood mononuclear cells). Given the potentially pathogeneic role of overexpression of these enzymes and their elevated levels in cancer cells against which sodium stibogluconate showed striking activity, sodium stibogluconate anti-cancer activity might be mediated significantly by targeting the PRL phosphatases. In particular, their inactivation is likely responsible for the part of the anti-cancer effect of sodium stibogluconate as a single agent that apparently functions independently of IFN signaling as indicated by its lack of effect on Stat1 phosphorylation in the absence of IFNα. Moreover, sodium stibogluconate represents a group of related chemical compounds with variable activities and toxicity in leishmaniases. Identification of sodium stibogluconate as an inhibitor of PRL phosphatases provides a foundation for the development of more specific and effective PRL inhibitors as targeted anti-cancer therapeutics through screening sodium stibogluconate-related chemical compounds. In this regard, our finding that the PRL phosphatases showed differential sensitivities to sodium stibogluconate is significant as it indicates the feasibility of developing inhibitors targeting individual members of these closely related phosphatases. The proposed mechanism of PRL PTPases as potential targets of sodium stibogluconate anti-cancer activity is illustrated in the figures attached hereto.

The ability of antimony to form covalent bonds with sulfhydryl group and the existence of a conserved active site cysteine residue in catalytic pockets of all PTPases suggest involvement of modification of the cysteine residue by pentavalent antimony in sodium stibogluconate as an inactivation mechanism. This mode of action of sodium stibogluconate against PTPases is supported by our observation that sodium stibogluconate induces an increase in the molecular mass of PRL-2 phosphatase. Since selective higher molecular weight compounds in sodium stibogluconate were active against PTPases, it further suggests that antimony conjugated with carbohydrates in a specific configuration may gain assess to the PTPase catalytic pockets and allow optimal antimony/cysteine interaction, resulting in modification of the cysteine residue and PTPase inactivation. Such an inhibitory mechanism could provide a rational explanation for the differential sodium stibogluconate—sensitivities of PTPases, each of which possesses a catalytic pocket of unique geometry for specific interaction with its substrates. It might therefore be feasible to develop more specific and effective inhibitors against individual PTPases as novel therapeutics through screening of chemical compounds comprised of antimony conjugated to different organic moieties.

Glucatime (GT, or meglumine antimonate) is an anti-leishmania drug, consisted of pentavalent antimony conjugated to N-methyl-D-glucamine. Its mechanism of action is elusive despite of its long time clinical usage. Given its chemical composition, our hypothesis would predict that glucatime has PTPase inhibitory activity and may target PTPases different from that of sodium stibogluconate. Herein we demonstrate that glucatime is potent inhibitor of selective PTPases in vitro and inactivates its target PTPases inside cells. Moreover, our results showed that glucatime targets a spectrum of PTPases that overlaps with but is different from that affected by sodium stibogluconate. We also provide evidence of a growth inhibitory activity of glucatime against WM9 human melanoma cells in culture, which might be related to its inactivation of oncogenic PRL PTPases that are expressed in WM9 cells. These results together indicate that potential of glucatime as a novel anti-cancer therapeutic and provide strong evidence demonstrating the feasibility of developing inhibitors against individual PTPases as therapeutics based on pentavalent antimony conjugated to different organic moieties.

Figure 12:
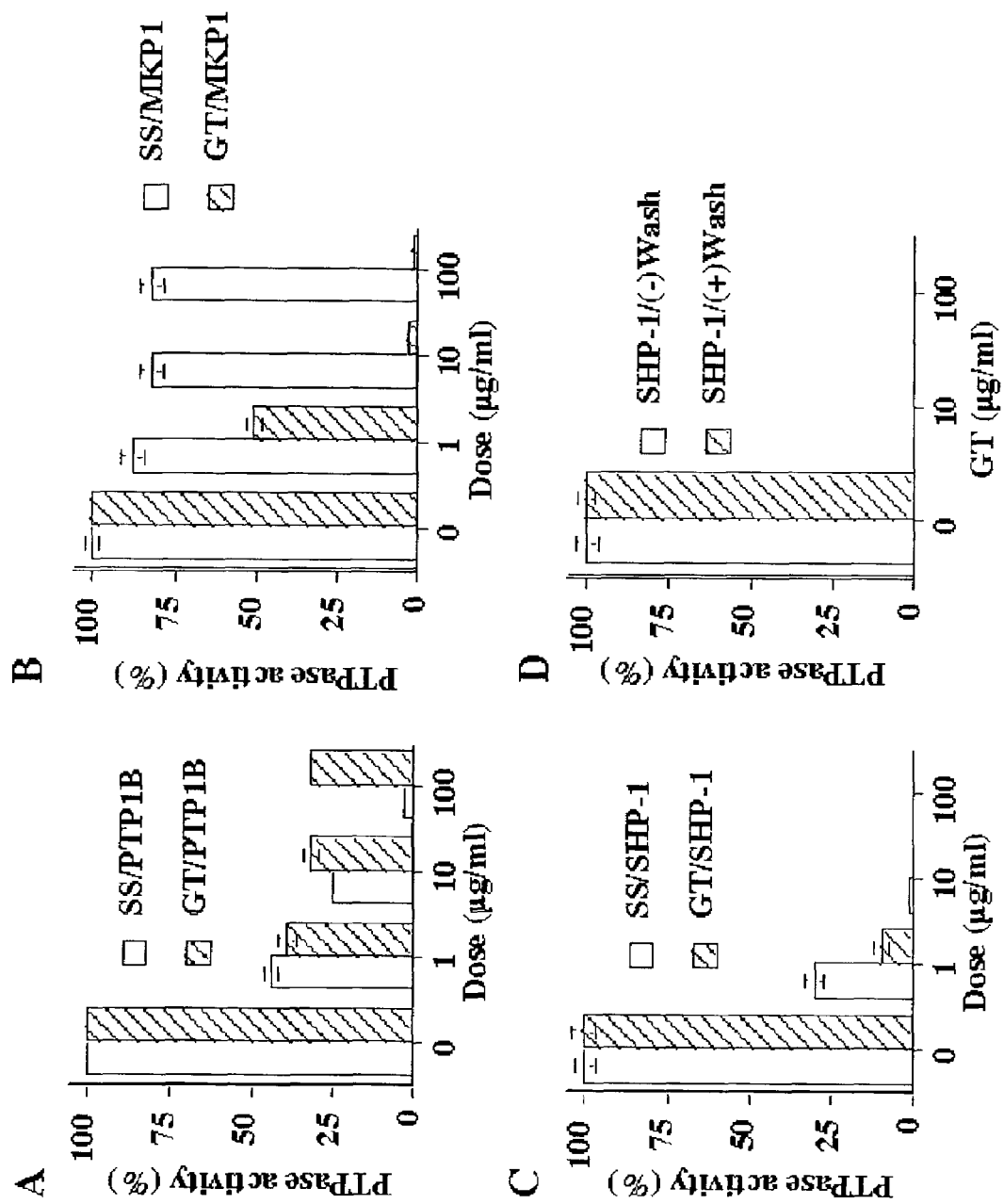
FIG. 12 illustrates that Glucatime has inhibitory activity against recombinant PTPases in vitro with its specificity different from that of sodium stibogluconate. Activities of recombinant PTP1B (A), MKP1 (B) and SHP-1 (C) in the absence or presence of glucatime or sodium stibogluconate in dephosphorylating a synthetic phosphotyrosine peptide in in vitro PTPase assays. Glucatime induced SHP-1 inactivation that was not removed by a washing process and thus was irreversible (D).

As shown in FIG. 12 glucatime has inhibitory activity against recombinant PTPases in vitro with its specificity different from that of sodium stibogluconate. Activities of recombinant PTP1B (A), MKP1 (B) and SHP-1 (C) in the absence or presence of glucatime or sodium stibogluconate in dephosphorylating a synthetic phosphotyrosine peptide in in vitro PTPase assays. Glucatime induced SHP-1 inactivation that was not removed by a washing process and thus was irreversible (D).

Figure 13:
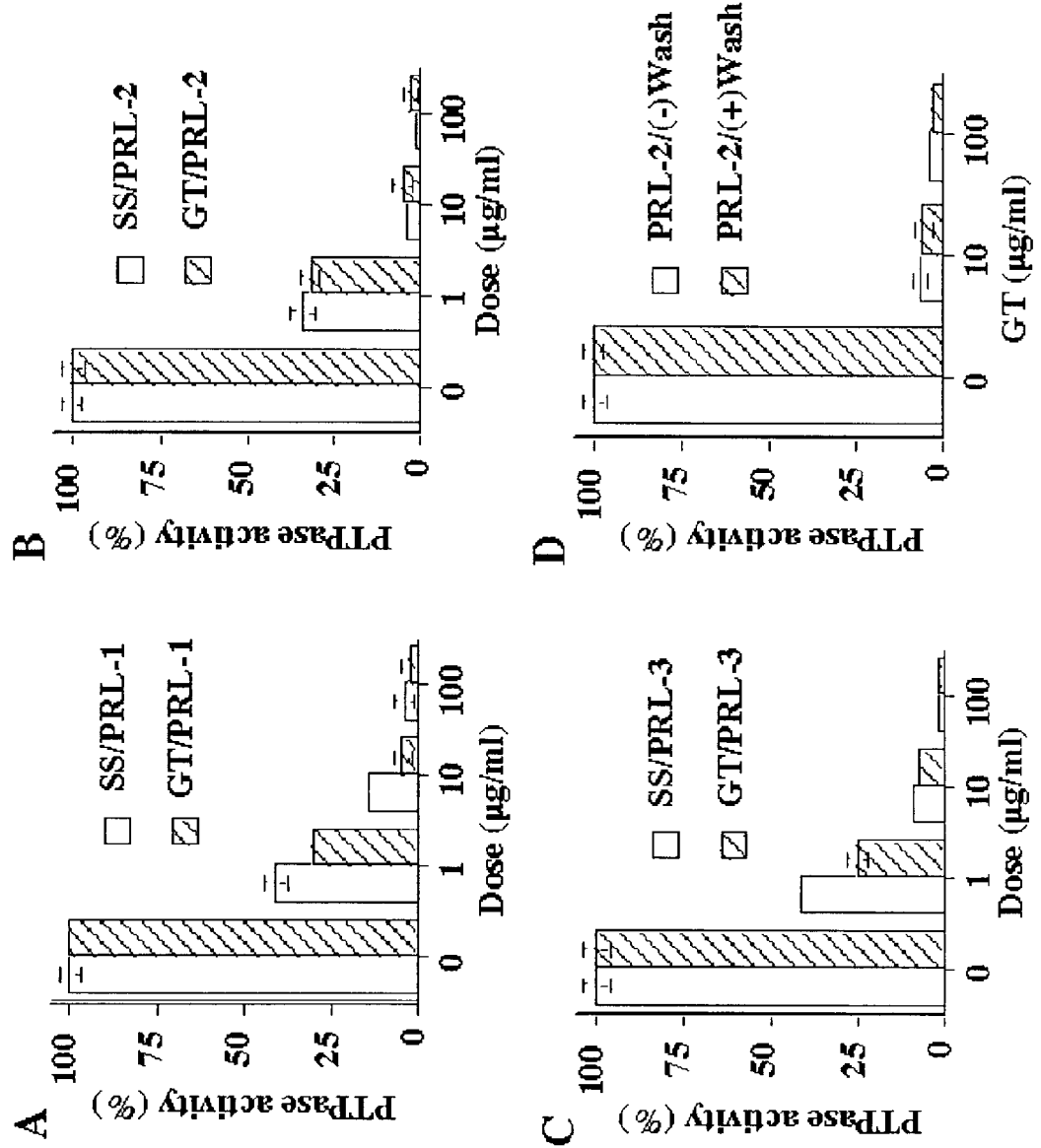
FIG. 13 illustrates that glucatime is a potent inhibitor of oncogenic PRL phosphatases in vitro. Activities of recombinant PRL-1 (A), PRL-2 (B) and PRL-3 (C) in the absence or presence of glucatime or sodium stibogluconate in dephosphorylating a synthetic phosphotyrosine peptide in in vitro PTPase assays. Glucatime induced PRL-2 inactivation that was not removed by a washing process and thus was irreversible (D).
Figure 14:
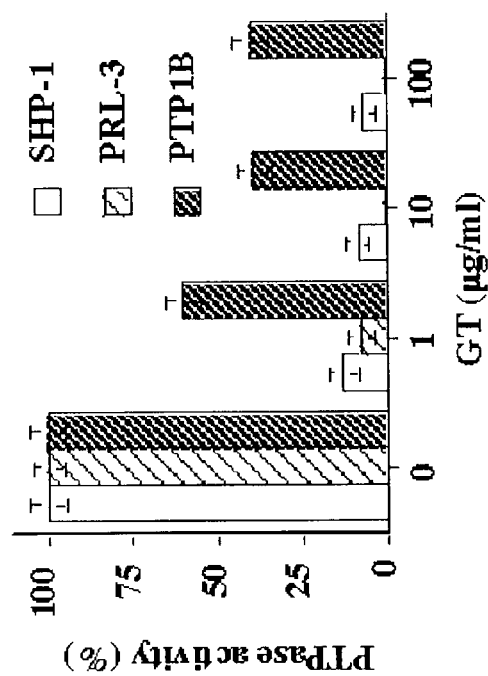
FIG. 14 illustrates detection of PTPase inhibitory activity of glucatime using an alternative PTPase substrate (DiFMUP) in in vitro PTPase assays. Activities of recombinant SHP-1, PRL-3 and PTP1B in the absence or presence of glucatime in dephosphorylating DiFMUP in PTPase assays.
Figure 15:
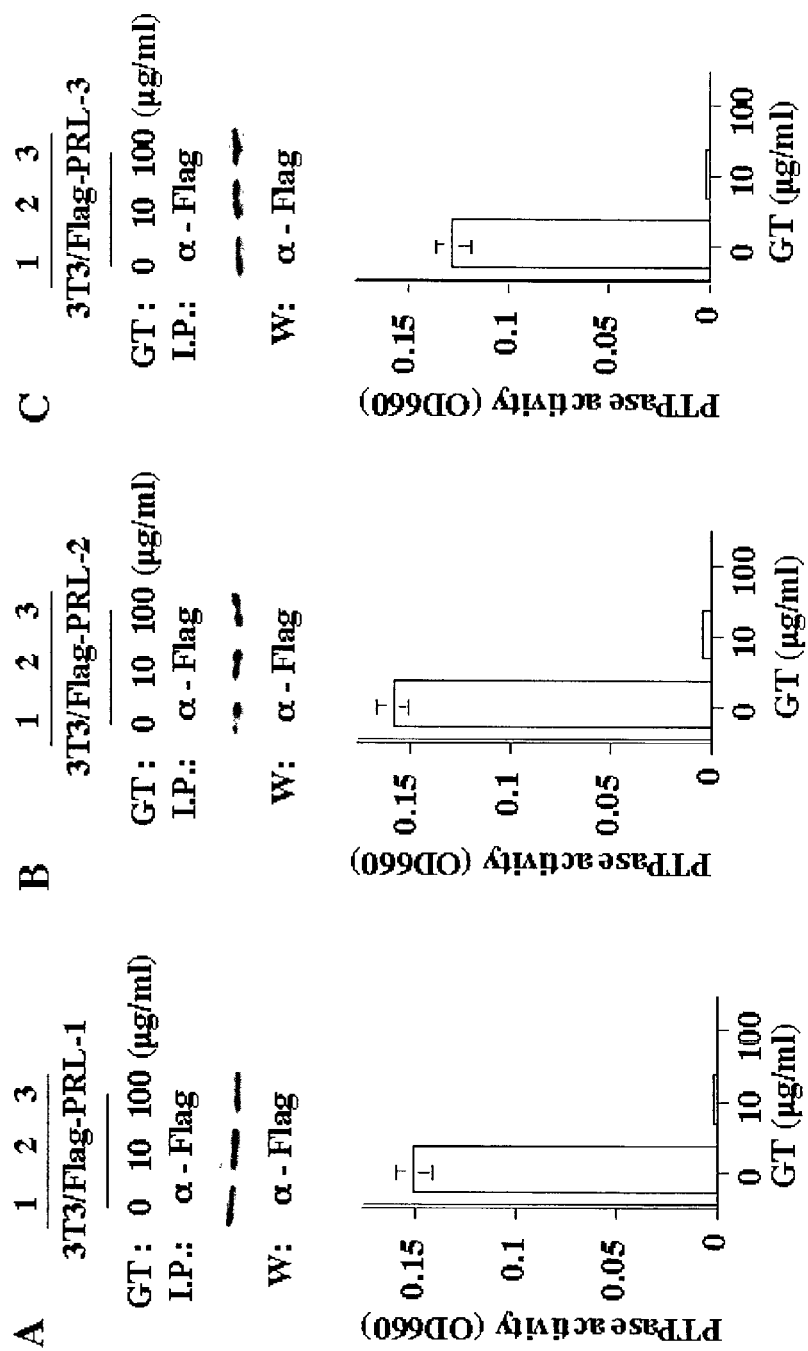
FIG. 15 illustrates that glucatime inactivates intracellular PRL phosphatases. NIH3T3 stable transfectants of Flag-tagged PRL-1 (A), PRL-2 (B) and PRL-3 (C) were untreated or treated with glucatime for 5 minutes and then washed to remove cell free drug. The Flag-tagged PRLs were immunoprecipitated from the cells using a monoclonal anti-Flag antibody. The amounts of Flag-tagged PRLs in the immunocomplexes were quantified by SDS-PAGE/Western blotting with the anti-Flag antibody (the top panel). Activities of the immunocomplexes in dephosphorylating a synthetic phosphotyrosine peptide were determined by in vitro PTPase assays (the low panel).
Figure 16:
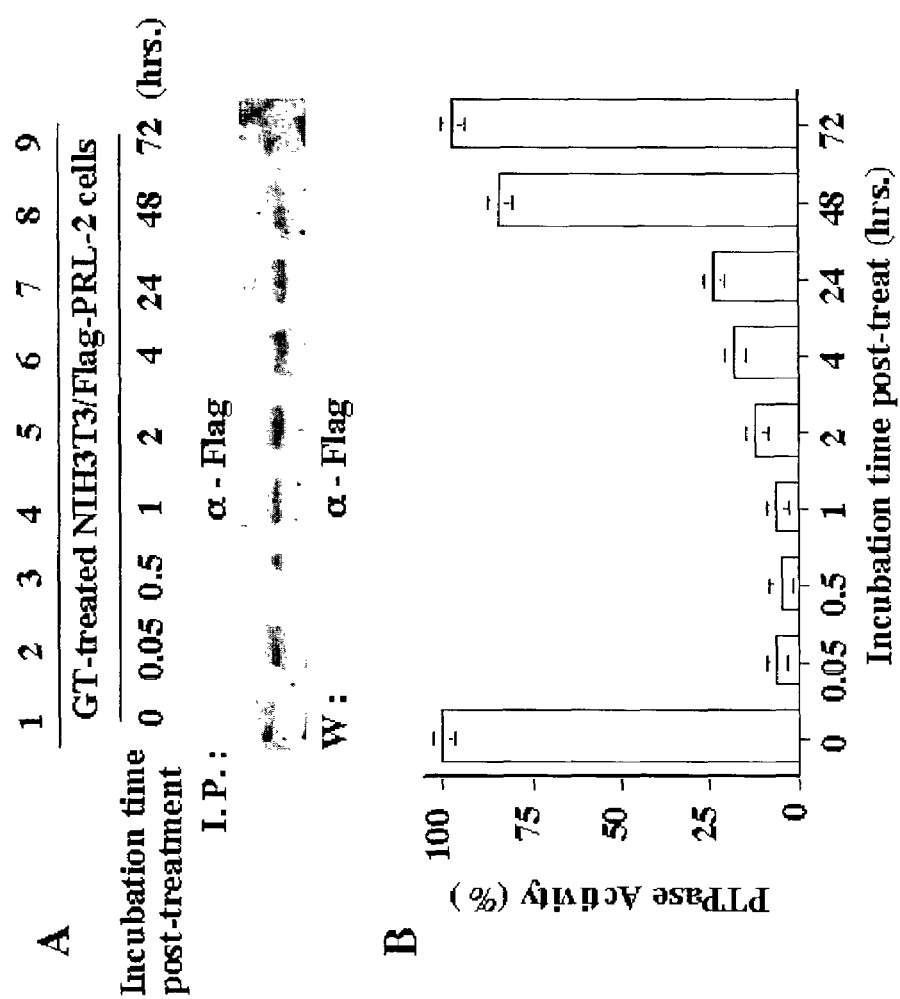
FIG. 16. Glucatime-induced inactivation of intracellular PRL-2 lasts more than 24 hours. NIH3T3 stable transfectant of Flag-tagged PRL-2 was treated with glucatime for 5 minutes, washed to remove cell free drug and then incubated for various times prior to termination by lysing the cells in lysis buffer. Flag-tagged PRL-2 was immunoprecipitated from the cell lysates using a monoclonal anti-Flag antibody. The amounts of Flag-tagged PRL-2 in the immunocomplexes were quantified by SDS-PAGE/Western blotting with the anti-Flag antibody (A). Activities of the immunocomplexes in dephosphorylating a synthetic phosphotyrosine peptide were determined by in vitro PTPase assays (B).
Figure 17:
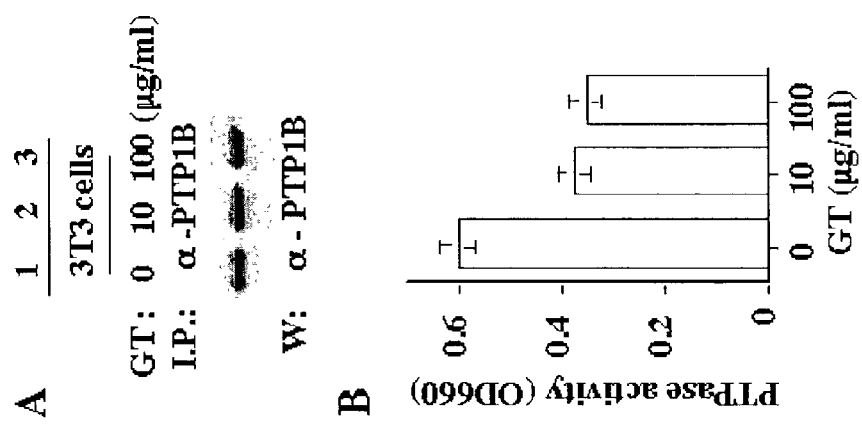
FIG. 17. Glucatime induces partial inhibition of intracellular PTP1B, similar to its partial inhibitory effect against recombinant PTP1B in vitro. NIH3T3 cells were untreated or treated with glucatime for 5 minutes. PTP1B protein was immunoprecipitated from the cells using an anti-PTP1B antibody. The amounts of PTP1B in the immunocomplexes were quantified by SDS-PAGE/Western blotting with the anti-PTP1B antibody (A). Activities of the immunocomplexes in dephosphorylating a synthetic phosphotyrosine peptide were determined by in vitro PTPase assays (B).

Glucatime is also a potent inhibitor of oncogenic PRL phosphatases in vitro. Activities of recombinant PRL-1 (A), PRL-2 (B) and PRL-3 (C) in the absence or presence (See FIG. 13) of glucatime or sodium stibogluconate in dephosphorylating a synthetic phosphotyrosine peptide in in vitro PTPase assays. Glucatime induced PRL-2 inactivation that was not removed by a washing process and thus was irreversible (D).

Detection of PTPase inhibitory activity of glucatime using an alternative PTPase substrate (DiFMUP) in in vitro PTPase assays. Activities of recombinant SHP-1, PRL-3 and PTP1B in the absence or presence of glucatime in dephosphorylating DiFMUP in PTPase assays.

Glucatime inactivates intracellular PRL phosphatases. NIH3T3 stable transfectants of Flag-tagged PRL-1 (A), PRL-2 (B) and PRL-3 (C) were untreated or treated with glucatime for 5 minutes and then washed to remove cell free drug. The Flag-tagged PRLs were immunoprecipitated from the cells using a monoclonal anti-Flag antibody. The amounts of Flag-tagged PRLs in the immunocomplexes were quantified by SDS-PAGE/Western blotting with the anti-Flag antibody (the top panel). Activities of the immunocomplexes in dephosphorylating a synthetic phosphotyrosine peptide were determined by in vitro PTPase assays (the low panel).

Glucatime-induced inactivation of intracellular PRL-2 lasts more than 24 hours. NIH3T3 stable transfectant of Flag-tagged PRL-2 was treated with glucatime for 5 minutes, washed to remove cell free drug and then incubated for various times prior to termination by lysing the cells in lysis buffer. Flag-tagged PRL-2 was immunoprecipitated from the cell lysates using a monoclonal anti-Flag antibody. The amounts of Flag-tagged PRL-2 in the immunocomplexes were quantified by SDS-PAGE/Western blotting with the anti-Flag antibody (A). Activities of the immunocomplexes in dephosphorylating a synthetic phosphotyrosine peptide were determined by in vitro PTPase assays (B).

Glucatime induces partial inhibition of intracellular PTP1B, similar to its partial inhibitory effect against recombinant PTP1B in vitro. NIH3T3 cells were untreated or treated with glucatime for 5 minutes. PTP1B protein was immunoprecipitated from the cells using an anti-PTP1B antibody. The amounts of PTP1B in the immunocomplexes were quantified by SDS-PAGE/Western blotting with the anti-PTP1B antibody (A). Activities of the immunocomplexes in dephosphorylating a synthetic phosphotyrosine peptide were determined by in vitro PTPase assays (B).

Glucatime inhibits the growth of human cancer cell lines in culture and augments IFNα-induced growth inhibition. Growth of human cancer cell lines cultured in the absence or presence of glucatime and/or IFNα (500 U/ml) for 6 days were determined by MTT assays. These cell lines were of different human malignancies, including lung cancer (A549), lymphoma (DR), ovarian cancer (HEY), breast cancer (MDA231, or MDA), neuroblastoma (SK-N-SH, or SK) and melanoma (WM9).

While this invention has been described with an emphasis upon preferred embodiments, it will be obvious to those of ordinary skill in the art that variations of the preferred compounds and methods may be used and that it is intended that the invention may be practiced otherwise than as specifically described herein.

TABLE 1

Growth inhibition of human tumor cell lines by sodium stibogluconate and IFNα.

| | | % of growth inhibition by day 6 (±s.d.) | | | | |
|---|---|---|---|---|---|---|
| | | (SS 12.5 μg/ml; IFNα 1,000 u/ml) | | | (SS 100 μg/ml; IFNα 1,000 u/ml) | |
| Cell line | Tumor type | SS | IFNα | SS + IFNα | SS | SS + IFNα |
| DR | Burkitt's Lymphoma | 45 (15) | 39 (2) | 80 (1) | 99 (1) | 99 (2) |
| U266 | Multiple myeloma | +3 (4) | 78 (10) | 93 (5) | 64 (10) | 100 (7) |
| H9 | T-lymphoma | 8 (16) | 86 (3) | 91 (3) | nd | 99 (3) |
| Peer | T-ALL | +3 (5) | 86 (4) | 91 (3) | nd | 98 (2) |
| WM9 | Melanoma | 27 (12) | 58 (2) | 84 (3) | 75 (4) | 100 (1) |
| WM35 | Melanoma | +8 (21) | 19 (3) | +3 (11) | 2 (19) | 29 (10) |
| DU145 | Prostate cancer | 36 (1) | 70 (5) | 85 (6) | 91 (2) | 96 (2) |
| C42 | Prostate cancer | 0 (18) | +19 (30) | 2 (18) | 15 (6) | 21 (7) |
| MDA231 | Breast cancer | 64 (9) | 79 (2) | 93 (2) | 97 (5) | 95 (4) |
| MDA435 | Breast cancer | 6 (2) | 29 (15) | 40 (39) | 97 (2) | 95 (3) |
| WiT49-N1 | Wilms tumor | 50 (8) | 22 (11) | 31 (10) | 97 (3) | 92 (0) |
| RC45 | Renal cell carcinoma | 18 (13) | 70 (15) | 79 (7) | 66 (13) | 85 (7) |
| 5637 | Blader carcinoma | 23 (7) | 28 (17) | 23 (6) | 74 (9) | 71 (7) |

Note:
"+" = positive effect on cell proliferation;
"nd" = not done.

What is claimed is:

1. A therapeutic composition comprising:
   (i) an effective amount of a pentavalent antimonial selected from the group consisting of glucantime and sodium stibogluconate, wherein said effective amount is from about 10 mg/kg to 140 mg/kg of said pentavalent antimonial; and
   (ii) further comprising an effective amount of IFN-α.

2. The therapeutic composition of claim 1, wherein said pentavalent antimonial is glucantime.

3. The therapeutic composition of claim 1, wherein said pentavalent antimonial is sodium stibogluconate.

4. The therapeutic composition of claim 1, wherein said effective amount of the pentavalent antimonial is effective in treating cancer.

5. The therapeutic composition of claim 4, wherein said cancer is selected from the group consisting of lymphoma, multiple myeloma, leukemia, melanoma, prostate cancer, breast cancer, renal cancer, and bladder cancer.

6. The therapeutic composition of claim 1, wherein said effective amount of the pentavalent antimonial is effective in enhancing cytokine activity.

7. The therapeutic composition of claim 1, wherein said effective amount of the cytokine is about 500 U/ml.

8. A therapeutic composition comprising an effective amount of a purified fraction of a pentavalent antimonial, selected from the group consisting of glucantime and sodium stibogluconate, wherein said effective amount is from about 20 mg/kg to 50 mg/kg of said pentavalent antimonial and further comprising an effective amount of IFN-α.

9. The therapeutic composition of claim 8, wherein said pentavalent antimonial is glucantime.

10. The therapeutic composition of claim 8, wherein said pentavalent antimonial is sodium stibogluconate.

11. The therapeutic composition of claim 8, wherein said effective amount of the pentavalent antimonial is effective in treating cancer.

12. The therapeutic composition of claim 11, wherein said cancer is selected from the group consisting of lymphoma, multiple myeloma, leukemia, melanoma, prostate cancer, breast cancer, renal cancer, and bladder cancer.

13. The therapeutic composition of claim 8, wherein said effective amount of pentavalent antimonial is effective in enhancing cytokine activity.

14. The therapeutic composition of claim 8, wherein said effective amount of the cytokine is about 500 U/ml.

15. The therapeutic composition of claim 1, further comprising a pharmaceutically acceptable carrier.

16. The therapeutic composition of claim 8, further comprising a pharmaceutically acceptable carrier.

17. The therapeutic composition of claim 8, wherein said effective amount of the cytokine is about 500,000 Units.

18. The therapeutic composition of claim 1, wherein said effective amount of the cytokine is about 500,000 Units.

* * * * *